United States Patent
Bhamra et al.

(10) Patent No.: US 10,202,375 B2
(45) Date of Patent: Feb. 12, 2019

(54) N-PYRIDINYL ACETAMIDE DERIVATIVES AS WNT SIGNALLING PATHWAY INHIBITORS

(71) Applicant: Redx Pharma PLC, Macclesfield (GB)

(72) Inventors: Inder Bhamra, Macclesfield (GB); Michael Mathieson, Macclesfield (GB); Craig Donoghue, Macclesfield (GB); Richard Testar, Macclesfield (GB)

(73) Assignee: Redx Pharma PLC, Macclesfield (GB)

( * ) Notice: Subject to any disclaimer, the term of this patent is extended or adjusted under 35 U.S.C. 154(b) by 0 days.

(21) Appl. No.: 15/514,061

(22) PCT Filed: Oct. 8, 2015

(86) PCT No.: PCT/GB2015/052943
§ 371 (c)(1),
(2) Date: Mar. 24, 2017

(87) PCT Pub. No.: WO2016/055790
PCT Pub. Date: Apr. 14, 2016

(65) Prior Publication Data
US 2017/0298062 A1 Oct. 19, 2017

(30) Foreign Application Priority Data

Oct. 8, 2014 (GB) .................................. 1417832.1
Jul. 14, 2015 (GB) .................................. 1512279.9

(51) Int. Cl.
| C07D 471/04 | (2006.01) |
| C07D 487/04 | (2006.01) |
| A61K 31/497 | (2006.01) |
| A61K 31/519 | (2006.01) |
| A61K 45/06 | (2006.01) |

(52) U.S. Cl.
CPC .......... *C07D 471/04* (2013.01); *A61K 31/497* (2013.01); *A61K 31/519* (2013.01); *A61K 45/06* (2013.01); *C07D 487/04* (2013.01)

(58) Field of Classification Search
CPC .. C07D 471/04; C07D 487/04; C07D 473/00; A61K 31/497
See application file for complete search history.

(56) References Cited

FOREIGN PATENT DOCUMENTS

| GB | 2513403 A | 10/2014 |
| WO | WO-2004052880 A1 | 6/2004 |
| WO | WO-2009075874 A1 | 6/2009 |
| WO | WO-2010101849 A1 | 9/2010 |
| WO | WO-2011042798 A1 | 4/2011 |
| WO | WO-2012003189 A1 | 1/2012 |

OTHER PUBLICATIONS

International Search Report and Written Opinion dated Dec. 21, 2015, from corresponding International Application No. PCT/GB2015/052943.
Liu et al., "Targeting Wnt-driven cancer through the inhibition of Porcupine by LGK974," Proc Natl Acad Sci U S A, 110(50):20224-20229 (2013).
Search Report issued by Intellectual Property Office in corresponding Application No. GB1417832.1, dated Jun. 12, 2015.

*Primary Examiner* — Joseph R Kosack
*Assistant Examiner* — Karen Cheng
(74) *Attorney, Agent, or Firm* — Dana M. Gordon; Foley Hoag LLP

(57) ABSTRACT

Disclosed are compounds useful as inhibitors of the Wnt signalling pathway. Specifically, inhibitors of Porcupine (Porcn) are contemplated by the invention. In addition, the invention contemplates processes to prepare the compounds and uses of the compounds. The compounds of the invention may therefore be used in treating conditions mediated by the Wnt signalling pathway, for example, in treating cancer, sarcoma, melanoma, skin cancer, haematological tumors, lymphoma, carcinoma, and leukemia; or enhancing the effectiveness of an anti-cancer treatment.

24 Claims, No Drawings

N-PYRIDINYL ACETAMIDE DERIVATIVES AS WNT SIGNALLING PATHWAY INHIBITORS

RELATED APPLICATIONS

This application is a § 371 national stage application based on Patent Cooperation Treaty Application serial number PCT/GB2015/052943, filed Oct. 8, 2015; which claims the benefit of priority to GB 1417832.1, filed Oct. 8, 2014; and GB 1512279.9, filed Jul. 14, 2015.

This invention relates to compounds. More specifically, the invention relates to compounds useful as inhibitors of the Wnt signalling pathway. Specifically, inhibitors of Porcupine (Porcn) are contemplated by the invention. In addition the invention contemplates processes to prepare the compounds and uses of the compounds.

The compounds of the invention may therefore be used in treating conditions mediated by the Wnt signalling pathway, for example secreted Wnt ligand mediated diseases which may be treated by inhibition of porcupine; treating cancer, sarcoma, melanoma, skin cancer, haematological tumors, lymphoma, carcinoma, and leukemia; or enhancing the effectiveness of an anti-cancer treatment.

BACKGROUND

The Wnt genes encode a large and highly conserved family of secreted growth factors. During normal development, transcription of Wnt family genes is tightly regulated both temporally and spatially. To date, 19 Wnt proteins have been discovered in humans. All of the Wnt proteins are 38- to 43-kDa cysteine-rich glycoproteins. Wnts have a range of roles during development, governing cell fate, migration, proliferation and death. These include body axis formation in zebrafish and xenopus, wing and eye development in drosophila and brain development in mice (Parr, et al. (1994) Curr. Opinion Genetics & Devel. 4:523-528, McMahon A P, Bradley A (1990) Cell 62: 1073-1085). In adults the role of Wnts is thought to be linked to maintaining tissue homeostasis with aberrant signalling implicated in a variety of cancers.

Wnt-mediated signalling occurs through binding of Wnt ligand to frizzled (Fzd) proteins, seven-transmembrane receptors. These receptors contain an N-terminal cysteine rich domain (CRD) which serves as the Wnt binding domain. Binding is stabilised by low-density-lipoprotein receptor-related proteins 5 and 6 (Lrp5 and Lrp6) (He, et al. (2004) Dev April; 131(8):1663-77). Fizzled ligation by Wnt is known to activate at least three different signalling pathways including the "canonical" β-catenin pathway, "non-canonical" planar cell polarity (PCP) and calcium pathways. Wnt signalling is further regulated by alternative receptors, including Ror2, secreted antagonists, such as WIF-1 (Hsieh, et al. (1999) Nature April 1; 398(6726):431-6) and alternative Wnt receptors, such as Dickkopf (DKK) (Niehrs C (2006) Oncogene December 4; 25(57):7469-81).

When inactive, β-Catenin is rapidly turned over by a conglomeration of several proteins known as the "destruction complex". The complex consists of Axin, adenomatous polyposis coli (APC), casein kinase (CK)-1a and glycogen synthasekinase (GSK)-3β (Hamada, et al. (1999) Science 12; 283(5408):1739-42). In this state, β-catenin is phosphorylated on serine-threonine on the amino terminus leading to ubiquitination (Behrens, et al. (1998) Science 280: 596-599). In the canonical pathway of Wnt activation, Wnt-ligated Fzd binds to and activates cytoplasmic Dishevelled (Dvl) (Chen, et al. (2003) Science 301:1391-94). Wnt-ligated Lrp5 and Lrp6 directly bind to cytoplasmic Axin, inhibiting its function as a destruction complex stabiliser (Zeng, et al. (2008) Dev. 135, 367-375). These associations lead to a destabilisation of the destruction complex and cytosolic accumulation of β-catenin. Stabilisation and accumulation of β-catenin leads to nuclear translocation where it complexes with T cell factor/lymphoid enhancer factor (TCF/LEF) high mobility group transcription factors and promotes transcription of target genes such as Cyclin D1, p21 and cMyc.

Oncogenic mutations in the β-catenin gene CTNNb1 exclusively affect specific serine and threonine and surrounding residues vital for targeted degradation by APC (Hart, et al. (1999) Curr. Biol. 9:207-210). This interaction is especially apparent in colorectal cancer, where the majority of tumours present with APC mutations and an increased proportion of the remainder express CTNNb1 mutations (Iwao, et al. (1998) Cancer Res Mar. 1, 1998 58; 1021).

Many recent studies have investigated compounds targeting β-catenin or other downstream Wnt pathway proteins. Recent research suggests that modulating Wnt-Wnt receptor interaction at the cell surface is effective in reducing cell oncogenicity. This has been shown in systems with tumourgenicity driven by Wnt ligand overexpression (Liu, et al. (2013) PNAS 10; 110(50):20224-9) and where Wnt expression is driven by downstream pathway activation (Vincan et al., Differentiation 2005; 73: 142-153). Vincan et al transfected non-functional Frd7 receptor into a SK-CO-1 cell line with a homozygous APC mutation driving Wnt pathway activation. These cells demonstrated modulated morphology and reduced tumour-forming efficiency compared to parental cells in a xenograft model. This data suggests that modulating Wnt ligand-mediated signalling may have a beneficial effect even in malignancies with downstream Wnt pathway mutations.

The described invention is proposed to inhibit Wnt-mediated signalling. This includes paracrine signalling in the tissues surrounding tumours and autocrine and paracrine signalling in cancer cells.

Wnt proteins undergo post-translational modification, shown in several mutation experiments to be vital for effective protein trafficking and secretion (Tang, et al. (2012) Dev. Biol 364, 32-41, Takada, R. et al (2006) Dev. Cell 11, 791-801). Palmitoylation of Wnt proteins occurs at several conserved amino acids (C77, S209) and is performed by porcupine, an O-acetyltransferase, in the endoplasmic reticulum. Mutations in porcupine have been shown to be the cause of developmental disorders, including focal dermal hypoplasia, through impaired Wnt pathway signalling (Grzeschik, et al. (2007) Nat. Genet, 39 pp. 833-835). The dependence of Wnt ligand signalling on porcupine and the body of evidence linking Wnt pathway signalling to cancer has led to porcupine being identified as a potential anti-cancer target.

US 2014/0038922 discloses compounds that inhibit the Wnt signalling pathway and the use of these compounds in the treatment of Wnt signalling-related diseases. Similarly, WO 2012/003189 and WO 2010/101849 disclose compounds and methods for modulating Wnt signalling pathway.

An aim of the present invention is to provide alternative or improved Wnt signalling modulators. For example, an aim of the present invention is to provide alternative or improved Wnt signalling inhibitors, optionally inhibitors of porcupine.

Furthermore, it is an aim of certain embodiments of this invention to provide new compounds for use in: Wnt mediated diseases, such as secreted Wnt ligand mediated diseases which may be treated by inhibition of porcupine; treating cancer, sarcoma, melanoma, skin cancer, haematological tumors, lymphoma, carcinoma, and leukemia; or enhancing the effectiveness of an anti-cancer treatment.

It is an aim of certain embodiments of this invention to provide new cancer treatments. In particular, it is an aim of certain embodiments of this invention to provide compounds which have comparable activity to existing treatments, ideally they should have better activity. Certain embodiments of the invention also aim to provide improved solubility compared to prior art compounds and existing therapies. It is particularly attractive for certain compounds of the invention to provide better activity and better solubility over known compounds.

It is an aim of certain embodiments of this invention to provide compounds which exhibit reduced cytotoxicity relative to prior art compounds and existing therapies.

Another aim of certain embodiments of this invention is to provide compounds having a convenient pharmacokinetic profile and a suitable duration of action following dosing. A further aim of certain embodiments of this invention is to provide compounds in which the metabolised fragment or fragments of the drug after absorption are GRAS (Generally Regarded As Safe).

Certain embodiments of the present invention satisfy some or all of the above aims.

BRIEF SUMMARY OF THE DISCLOSURE

In accordance with the present invention there is provided a compound of formula (I):

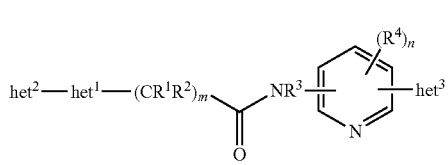

(I)

wherein
$het^1$ represents a 8 or 9 membered bicyclic heterocyclic ring system comprising a 5 membered ring and 1, 2, 3 or 4 heteroatoms selected from N, O or S, wherein the 8 or 9 membered bicyclic heterocyclic ring system is unsubstituted or substituted, and when substituted the ring system is substituted with 1, 2, or 3 groups independently selected at each occurrence from: halo, $C_{1-4}$ alkyl, $C_{1-4}$ haloalkyl, $-OR^{A2}$, $-NR^{A2}R^{B2}$, $-CN$, $-SO_2R^{A2}$, and $C_{3-6}$ cycloalkyl;
$het^2$ is a 5 or 6 membered heterocyclic ring which may be unsubstituted or substituted, and when substituted the ring is substituted with 1, 2 or 3 groups independently selected at each occurrence from: halo, $C_{1-4}$ alkyl, $C_{1-4}$ haloalkyl, $-OR^{A1}$, $-NR^{A1}R^{B1}$, $-CN$, $-NO_2$, $-NR^{A1}C(O)R^{B1}$, $-C(O)NR^{A1}R^{B1}$, $-NR^{A1}SO_2R^{B1}$, $-SO_2NR^{A1}R^{B1}$, $-SO_2R^{A1}$, $-C(O)R^{A1}$, $-C(O)OR^{A1}$ and $C_{3-6}$ cycloalkyl;
$het^3$ is a 6 membered heterocyclic ring which may be unsubstituted or substituted, and when substituted the ring is substituted with 1, 2 or 3 groups independently selected at each occurrence from: halo, $C_{1-4}$ alkyl, $C_{1-4}$ haloalkyl, $-OR^{A1}$, $-NR^{A1}R^{B1}$, $-CN$, $-NO_2$, $-NR^{A1}C(O)R^{B1}$, $-C(O)NR^{A1}R^{B1}$, $-NR^{A1}SO_2R^{B1}$, $-SO_2NR^{A1}R^{B1}$, $-SO_2R^{A1}$, $-C(O)R^{A1}$, $-C(O)OR^{A1}$ and $C_{3-6}$ cycloalkyl;
$R^1$ and $R^2$ are independently selected at each occurrence from: H, halo, $C_{1-4}$ alkyl, $C_{1-4}$ haloalkyl, $-OR^{A3}$, $-NR^{A3}R^{B3}$ and $C_{3-6}$ cycloalkyl;
$R^3$ is selected from: H, $C_{1-4}$ alkyl, $C_{1-4}$ haloalkyl, and $C_{3-6}$ cycloalkyl;
$R^4$ is independently selected at each occurrence from: halo, $C_{1-4}$ alkyl, $C_{1-4}$ haloalkyl, $-CN$, $-OR^{A4}$, $-NR^{A4}R^{B4}$, $-SO_2R^{A4}$, $C_{3-6}$ cycloalkyl and $C_{3-6}$ halocycloalkyl;
m is selected from, 1, 2 or 3;
n is selected from 0, 1 or 2; and
$R^{A1}$, $R^{B1}$, $R^{A2}$, $R^{B2}$, $R^{A3}$, $R^{B3}$, $R^{A4}$ and $R^{B4}$ are at each occurrence independently selected from: H, $C_{1-4}$ alkyl, $C_{1-4}$ haloalkyl.

The invention also provides pharmaceutically acceptable salts of compounds of the invention. Accordingly, there is provided compounds of formula (I) and pharmaceutically acceptable salts thereof.

In an embodiment the compound according to formula (I) is a compound according to formulae (IIa) or (IIb):

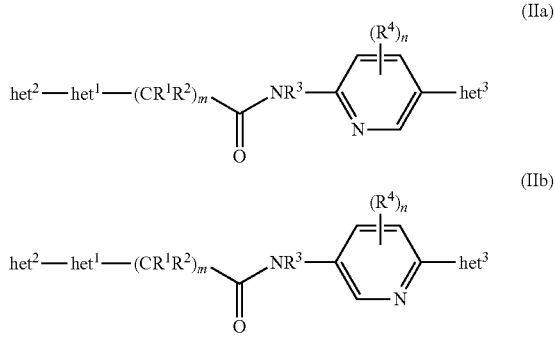

$Het^2$ may be represented by an aromatic, saturated or unsaturated 5 or 6 membered heterocyclic ring which is unsubstituted or substituted.

$Het^2$ may be represented by a ring selected from unsubstituted or substituted: pyrazole, imidazole, pyridine, pyrazine, pyrimidine, pyridazine, pyran, tetrahydropyran, dihydropyran, piperidine, piperazine, morpholine, thiomorpholine, oxazine, dioxine, dioxane, thiazine, oxathiane and dithiane.

Preferably, $het^2$ may be represented by unsubstituted or substituted: pyrazole, imidazole, pyridine, tetrahydropyran, dihydropyran, piperidine, piperazine and morpholine.

Optionally, $het^2$ is represented by an unsubstituted or substituted pyridine.

$Het^2$ may be unsubstituted or substituted with 1, 2, or 3 groups selected from: halo, $C_{1-4}$ alkyl, $C_{1-4}$ haloalkyl, $-OR^{A1}$, $-NR^{A1}R^{B1}$, $-CN$, and $C_{3-6}$ cycloalkyl. Preferably, $het^2$ may be unsubstituted or substituted with 1, 2, or 3 groups selected from: halo, $C_{1-4}$ alkyl, $-OR^{A1}$, and $C_{1-4}$ haloalkyl, wherein $R^{A1}$ is H, methyl, or trifluoromethyl.

In a preferred embodiment $het^2$ is unsubstituted or substituted with 1 or 2 groups selected from: fluoro, chloro, methyl, ethyl, trifluoromethyl, trifluoroethyl, $-CN$ and $-OCF_3$. In a particularly preferred embodiment $het^2$ is unsubstituted or substituted with 1 or 2 groups selected from methyl and trifluoromethyl.

Preferably, $het^2$ is unsubstituted or substituted with 1 or 2 groups. More preferably, $het^2$ is unsubstituted or substituted with 1 group.

Het² may be unsubstituted pyridine, unsubstituted pyrazole, unsubstituted tetrahydropyran, unsubstituted dihydropyran, unsubstituted piperidine, unsubstituted piperazine and unsubstituted morpholine, methylpyridine, dimethylpyridine, ethylpyridine, iso-propylpyridine, tert-butylpyridine, trifluoromethylpyridine, methoxypyridine, ethyoxypyridine, aminopyridine, N-methyl-aminopyridine, N,N-dimethyl-aminopyridine, nitropyridine, cyanopyridine, methyltetrahydropyran, dimethyltetrahydropyran, ethyltetrahydropyran, iso-propyltetrahydropyran, tert-butyltetrahydropyran, trifluoromethyltetrahydropyran, methoxytetrahydropyran, ethyoxytetrahydropyran, aminotetrahydropyran, N-methyl-aminotetrahydropyran, N,N-dimethyl-aminotetrahydropyran, nitrotetrahydropyran, cyanotetrahydropyran, methyldihydropyran, dimethyldihydropyran, ethyldihydropyran, iso-propyldihydropyran, tert-butyldihydropyran, trifluoromethyldihydropyran, methoxydihydropyran, ethyoxydihydropyran, aminodihydropyran, N-methyl-aminodihydropyran, N,N-dimethyl-aminodihydropyran, nitrodihydropyran, cyanodihydropyran, methylpiperidine, dimethylpiperidine, ethylpiperidine, iso-propylpiperidine, tert-butylpiperidine, trifluoromethylpiperidine, methoxypiperidine, ethyoxypiperidine, aminopiperidine, N-methyl-aminopiperidine, N,N-dimethyl-aminopiperidine, nitropiperidine, cyanopiperidine, methylpiperazine, dimethylpiperazine, ethylpiperazine, iso-propylpiperazine, tert-butylpiperazine, trifluoromethylpiperazine, methoxypiperazine, ethyoxypiperazine, aminopiperazine, N-methyl-aminopiperazine, N,N-dimethyl-aminopiperazine, nitropiperazine, cyanopiperazine, methylmorpholine, dimethylmorpholine, ethylmorpholine, iso-propylmorpholine, tert-butylmorpholine, trifluoromethylmorpholine, methoxymorpholine, ethyoxymorpholine, aminomorpholine, N-methyl-aminomorpholine, N,N-dimethyl-aminomorpholine, nitromorpholine, cyanomorpholine, methylpyrazole, dimethylpyrazole, ethylpyrazole, iso-propylpyrazole, tert-butylpyrazole, trifluoromethylpyrazole, methoxypyrazole, ethyoxypyrazole, aminopyrazole, N-methyl-aminopyrazole, N,N-dimethyl-aminopyrazole, nitropyrazole, or cyanopyrazole.

Het³ may be represented by an aromatic, saturated or unsaturated 6 membered heterocyclic ring which is unsubstituted or substituted and comprises at least one nitrogen atom. Preferably the ring is aromatic or saturated. Optionally, het³ is not pyridine.

Het³ may be represented by an aromatic, saturated or unsaturated 6 membered heterocyclic ring which is unsubstituted or substituted and comprises 2 heteroatoms, preferably the ring is aromatic or saturated. In a preferred embodiment het³ is represented by an aromatic, saturated or unsaturated 6 membered heterocyclic ring which is unsubstituted or substituted and comprises 2 nitrogen atoms, preferably the ring is aromatic or saturated.

Het³ may be represented by a ring selected from unsubstituted or substituted: pyrimidine, pyrazine, pyridazine, piperazine, dioxine, dioxane, morpholine and thiomorpholine.

Preferably, het³ may be represented by a ring selected from pyrimidine, pyrazine, pyridazine or piperazine.

Preferably, het³ may be represented by a ring selected from pyrimidine, pyrazine or pyridazine.

Optionally, het³ is represented by a ring selected from unsubstituted or substituted: pyrimidine and pyrazine. Preferably, het³ is represented by a ring selected from unsubstituted or substituted pyrazine.

Het³ may be unsubstituted or substituted with 1, 2, or 3 groups selected from: halo, $C_{1-4}$ alkyl, $C_{1-4}$ haloalkyl, —OR$^{A1}$, —NR$^{A1}$R$^{B1}$, —CN, —C(O)R$^{A1}$, —C(O)OR$^{A1}$ and $C_{3-6}$ cycloalkyl. Preferably, het³ may be unsubstituted or substituted with 1, 2, or 3 groups selected from: halo, $C_{1-4}$ alkyl, $C_{1-4}$ haloalkyl, —OR$^{A1}$, —C(O)R$^{A1}$ and —C(O)OR$^{A1}$, wherein R$^{A1}$ is H, methyl, tert-butyl or trifluoromethyl.

In a particular preferred embodiment het³ is unsubstituted or substituted with 1 or 2 groups selected from: fluoro, chloro, methyl, ethyl, trifluoromethyl, trifluoroethyl, —OCF$_3$, —C(O)Me, —C(O)OMe, —C(O)Et and —C(O)O$^t$Bu.

Preferably, het³ is unsubstituted or substituted with 1 or 2 groups. More preferably, het³ is unsubstituted or substituted with 1 group.

In an embodiment het² is represented by an aromatic, saturated or unsaturated 6 membered heterocyclic ring which is unsubstituted or substituted, and het³ is represented by an aromatic, saturated or unsaturated 6 membered heterocyclic ring which is unsubstituted or substituted and comprises 2 heteroatoms.

In an embodiment het² is represented by a ring selected from unsubstituted or substituted: pyridine, pyrazole, imidazole, pyrazine, pyrimidine, pyridazine, pyran, tetrahydropyran, dihydropyran, piperidine, piperazine, morpholine, thiomorpholine, oxazine, dioxine, dioxane, thiazine, oxathiane and dithiane; and het³ is represented by a ring selected from unsubstituted or substituted: pyrimidine, pyrazine, pyridazine, piperazine, dioxine, dioxane, morpholine and thiomorpholine.

Preferably, het² is represented by a ring selected from unsubstituted or substituted: pyridine, pyrazole, imidazole, tetrahydropyran, dihydropyran, piperidine, piperazine and morpholine; and het³ is represented by a ring selected from unsubstituted or substituted: pyrimidine, pyrazine, pyridazine and piperazine.

Het¹ represents a substituted or unsubstituted 8 or 9 membered bicyclic heteroaryl group comprising a 5 membered ring and comprising 1, 2, 3 or 4 heteroatoms selected from N, O or S. Het¹ represents a substituted or unsubstituted 9 membered bicyclic heteroaryl group comprising a 5 membered ring and a 6 membered ring, wherein the 5 membered ring comprises 1 or 2 N atoms and the 6-membered ring comprises 1 or 2 N atoms.

Het¹ may represent a group selected from unsubstituted or substituted: indolizine, indole, isoindole, benzofuran, isobenzofuran, benzothiophene, isobenzothiophene, benzothiazole, benzoxazole, benzisothiazole, benzisoxazole, imidazopyridine, imidazopyrimidine, indazole, azaindazole, purine, azaindole, and azaisoindole.

Het¹ may represent a group selected from unsubstituted or substituted: indolizine, indole, isoindole, benzofuran, isobenzofuran, benzothiophene, isobenzothiophene, benzothiazole, benzoxazole, benzisothiazole, benzisoxazole, imidazopyridine, imidazopyrimidine, indazole, azaindazole, purine, pyrrolopyrimidine, pyrazolopyrimidine, pyrazolopyridine, azaindole, and azaisoindole.

Het¹ represents a group selected from unsubstituted or substituted: indolizine, indole, isoindole, benzofuran, isobenzofuran, benzothiophene, isobenzothiophene, benzothiazole, benzoxazole, benzisothiazole, benzisoxazole, purine, pyrrolopyrimidine, pyrazolopyrimidine, pyrazolopyridine, azaindole, and azaisoindole.

Het¹ may represent a group selected from unsubstituted or substituted: imidazopyridine, imidazopyrimidine, azaindazole, purine, pyrrolopyrimidine, pyrazolopyrimidine, pyrazolopyridine, azaindole, and azaisoindole.

Optionally, het¹ may represent a group selected from unsubstituted or substituted: indolizine Preferably het¹ represents an unsubstituted or substituted pyrrolopyrimidine or azaindole. Preferably het¹ represents an unsubstituted or substituted azaindole.

When het¹ represents azaindole, the azaindole may be 5-azaindole, 6-azaindole or 7-azaindole, preferably 7-azaindole.

Het¹ may be unsubstituted or substituted with 1, 2, or 3 groups (preferably 1 or 2) selected from: halo, $C_{1-4}$ alkyl, $C_{1-4}$ haloalkyl, —$OR^{A2}$, —$NR^{A2}R^{B2}$ and —CN. Het¹ may be unsubstituted or substituted with 1 or 2 groups selected from: chloro, fluoro, methyl, ethyl, trifluoromethyl, trifluoroethyl, —$OCF_3$, —OH, —OMe, —OEt, —$NH_2$, —NHMe, —$NMe_2$ and —CN. Preferably, Het¹ may be unsubstituted or substituted with 1 or 2 methyl groups.

In an embodiment het¹ represents a group selected from unsubstituted or substituted: indolizine, indole, isoindole, benzofuran, isobenzofuran, benzothiophene, isobenzothiophene, benzothiazole, benzoxazole, benzisothiazole, benzisoxazole, imidazopyridine, imidazopyrimidine, indazole, azaindazole, purine, azaindole, and azaisoindole; het² is represented by an aromatic, saturated or unsaturated 6 membered heterocyclic ring which is unsubstituted or substituted; and het³ is represented by an aromatic, saturated or unsaturated 6 membered heterocyclic ring which is unsubstituted or substituted and comprises 2 heteroatoms.

In an embodiment het¹ represents a group selected from unsubstituted or substituted: indolizine, indole, isoindole, benzofuran, isobenzofuran, benzothiophene, isobenzothiophene, benzothiazole, benzoxazole, benzisothiazole, benzisoxazole, imidazopyridine, imidazopyrimidine, indazole, azaindazole, purine, pyrrolopyrimidine, pyrazolopyrimidine, azaindole, and azaisoindole; het² is represented by an aromatic, saturated or unsaturated 6 membered heterocyclic ring which is unsubstituted or substituted; and het³ is represented by an aromatic, saturated or unsaturated 6 membered heterocyclic ring which is unsubstituted or substituted and comprises 2 heteroatoms.

In an embodiment het¹ represents a group selected from unsubstituted or substituted: indolizine, indole, isoindole, benzofuran, isobenzofuran, benzothiophene, isobenzothiophene, benzothiazole, benzoxazole, benzisothiazole, benzisoxazole, imidazopyridine, imidazopyrimidine, indazole, azaindazole, purine, azaindole, and azaisoindole; het² is represented by a ring selected from unsubstituted or substituted: pyrazole, imidazole, pyridine, pyrazine, pyrimidine, pyridazine, pyran, tetrahydropyran, dihydropyran, piperidine, piperazine, morpholine, thiomorpholine, oxazine, dioxine, dioxane, thiazine, oxathiane and dithiane; het² is represented by unsubstituted or substituted pyridine; and het³ is represented by a ring selected from unsubstituted or substituted: pyrimidine, pyrazine, pyridazine, piperazine, dioxine, dioxane, morpholine and thiomorpholine.

In an embodiment het¹ represents a group selected from unsubstituted or substituted: indolizine, indole, isoindole, benzofuran, isobenzofuran, benzothiophene, isobenzothiophene, benzothiazole, benzoxazole, benzisothiazole, benzisoxazole, imidazopyridine, imidazopyrimidine, indazole, azaindazole, purine, pyrrolopyrimidine, pyrazolopyrimidine, azaindole, and azaisoindole; het² is represented by a ring selected from unsubstituted or substituted: pyrazole, imidazole, pyridine, pyrazine, pyrimidine, pyridazine, pyran, tetrahydropyran, dihydropyran, piperidine, piperazine, morpholine, thiomorpholine, oxazine, dioxine, dioxane, thiazine, oxathiane and dithiane; het² is represented by unsubstituted or substituted pyridine; and het³ is represented by a ring selected from unsubstituted or substituted: pyrimidine, pyrazine, pyridazine, piperazine, dioxine, dioxane, morpholine and thiomorpholine.

Optionally, het¹ represents a group selected from unsubstituted or substituted: indolizine, indole, isoindole, benzofuran, isobenzofuran, benzothiophene, isobenzothiophene, benzothiazole, benzoxazole, benzisothiazole, benzisoxazole, imidazopyridine, imidazopyrimidine, indazole, azaindazole, purine, azaindole, and azaisoindole; het² is represented by a ring selected from unsubstituted or substituted: pyrazole, imidazole, pyridine, tetrahydropyran, dihydropyran, piperidine, piperazine and morpholine; and het³ is represented by a ring selected from unsubstituted or substituted: pyrimidine, pyrazine, pyridazine and piperazine.

Optionally, het¹ represents a group selected from unsubstituted or substituted: indolizine, indole, isoindole, benzofuran, isobenzofuran, benzothiophene, isobenzothiophene, benzothiazole, benzoxazole, benzisothiazole, benzisoxazole, imidazopyridine, imidazopyrimidine, indazole, azaindazole, purine, pyrrolopyrimidine, pyrazolopyrimidine, azaindole, and azaisoindole; het² is represented by a ring selected from unsubstituted or substituted: pyrazole, imidazole, pyridine, tetrahydropyran, dihydropyran, piperidine, piperazine and morpholine; and het³ is represented by a ring selected from unsubstituted or substituted: pyrimidine, pyrazine, pyridazine and piperazine.

In an embodiment m is 1 or 2. In a preferred embodiment m is 1.

In an embodiment the compound according to formula (I) is a compound according to formula (III):

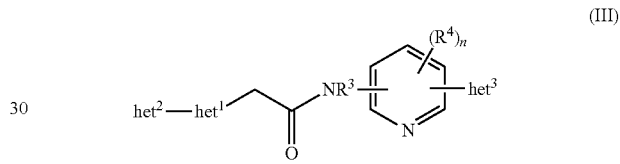

(III)

In an embodiment the compound according to formula (I) is a compound according to formulae (IIIa) or (IIIb):

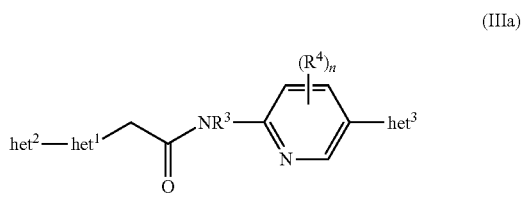

(IIIa)

(IIIb)

In an embodiment the compound according to formula (I) is a compound according to formulae (IVa) or (IVb):

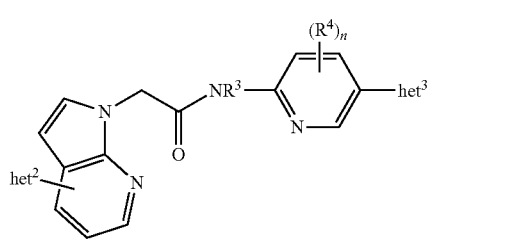

(IVa)

-continued

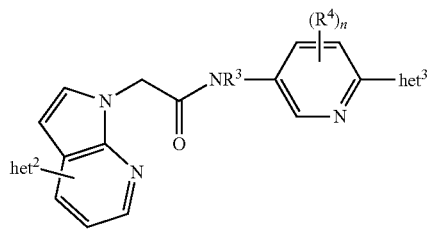

(IVb)

In an embodiment the compound according to formula (I) is a compound according to formulae (Va) or (Vb):

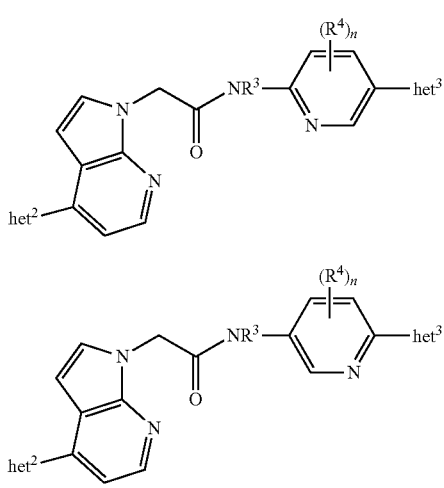

In an embodiment het¹ represents an unsubstituted or substituted azaindole; het² is represented by an aromatic, saturated or unsaturated 6 membered heterocyclic ring which is unsubstituted or substituted, and het³ is represented by an aromatic, saturated or unsaturated 6 membered heterocyclic ring which is unsubstituted or substituted and comprises 2 heteroatoms.

In an embodiment het¹ represents an unsubstituted or substituted azaindole; het² is represented by a ring selected from unsubstituted or substituted: pyrazole, imidazole, pyridine, pyrazine, pyrimidine, pyridazine, pyran, tetrahydropyran, dihydropyran, piperidine, piperazine, morpholine, thiomorpholine, oxazine, dioxine, dioxane, thiazine, oxathiane and dithiane; and het³ is represented by a ring selected from unsubstituted or substituted: pyrimidine, pyrazine, pyridazine, piperazine, dioxine, dioxane, morpholine and thiomorpholine.

Optionally, het¹ represents an unsubstituted or substituted azaindole; het² is represented by a ring selected from unsubstituted or substituted: pyrazole, imidazole, pyridine, tetrahydropyran, dihydropyran, piperidine, piperazine and morpholine; and het³ is represented by a ring selected from unsubstituted or substituted: pyrimidine, pyrazine, pyridazine and piperazine.

In a preferred embodiment het¹ represents an unsubstituted or substituted: azaindole; het² is represented by an unsubstituted or substituted pyridine; and het³ is represented by a ring selected from unsubstituted or substituted: pyrimidine, and pyrazine.

In an embodiment the compound according to formula (I) is a compound according to formula (VI):

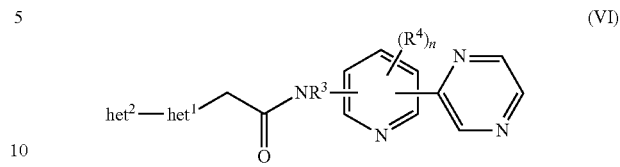

In an embodiment the compound according to formula (I) is a compound according to formulae (VIa) or (VIb):

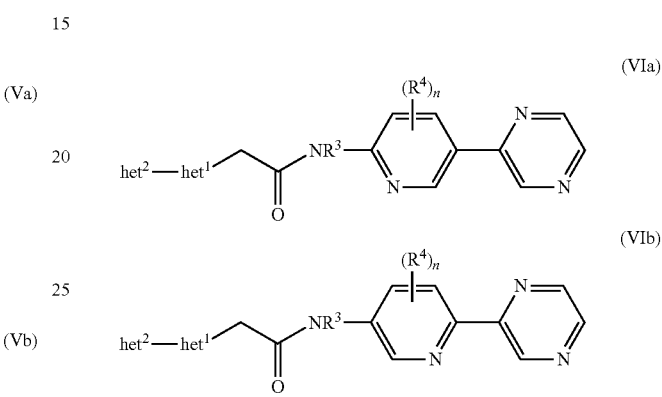

$R^1$ and $R^2$ may be independently selected at each occurrence from: H, halo, $C_{1-4}$ alkyl, $C_{1-4}$ haloalkyl, —$OR^{A3}$ and —$NR^{A3}R^{B3}$. $R^1$ and $R^2$ may be independently selected at each occurrence from: H, chloro, fluoro, methyl, ethyl, trifluoromethyl, trifluoroethyl, —$OCF_3$, —OH, —OMe, —OEt, —$NH_2$, —NHMe, and —$NMe_2$. Preferably, $R^1$ and $R^2$ are H.

In an embodiment m is 1 and $R^1$ and $R^2$ are H. In an alternative embodiment m is 2 and $R^1$ and $R^2$ are H. In an alternative embodiment m is 1 and $R^1$ is Me $R^2$ are H.

$R^3$ is optionally H or methyl.

$R^4$ is optionally selected at each occurrence from: halo, $C_{1-4}$ alkyl, $C_{1-4}$ haloalkyl, —CN, —$OR^{A4}$ and —$NR^{A4}R^{B4}$. $R^4$ may be independently selected at each occurrence from: H, chloro, fluoro, methyl, ethyl, trifluoromethyl, trifluoroethyl, —$OCF_3$, —OH, —OMe, —OEt, —$NH_2$, —NHMe, and —$NMe_2$.

$R^{A1}$, $R^{B1}$, $R^{A2}$, $R^{B2}$, $R^{A3}$, $R^{B3}$, $R^{A4}$ and $R^{B4}$ are at each occurrence independently selected from: H, methyl, ethyl and —$OCF_3$.

In a preferred embodiment the compound of formula (I) is a compound according to formulae (IIa), (IIIa), (IVa), (Va) or (VIa).

In a preferred embodiment n is 0.

The compound according to the invention may be selected from a group consisting of:

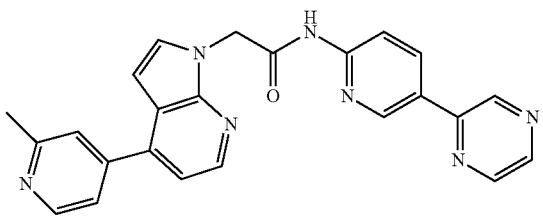 [SMILES: Cc1cc(-c2ccnc3c2ccn3CC(=O)Nc2ccc(-c3cnccn3)cn2)ccn1]

The compound according to the invention may also be selected from a group consisting of:
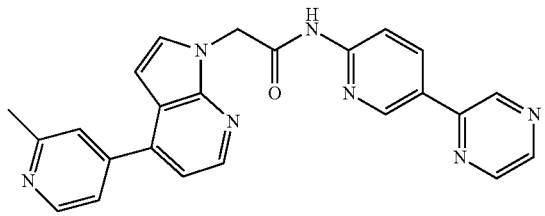
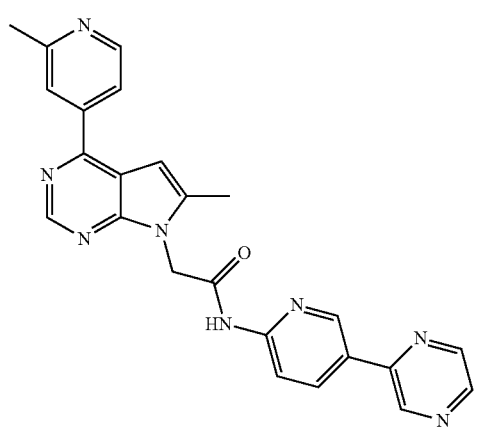
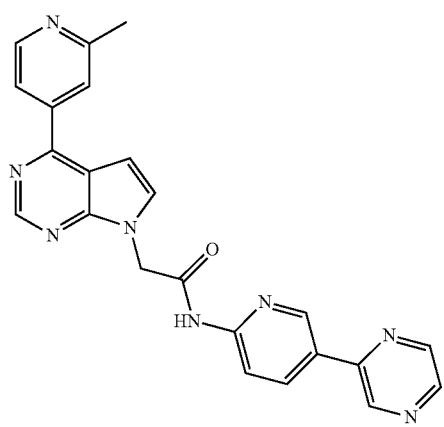
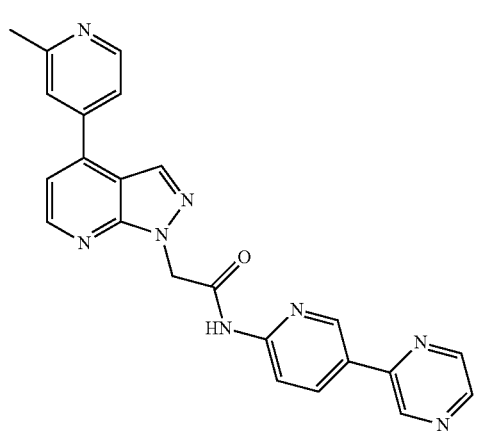
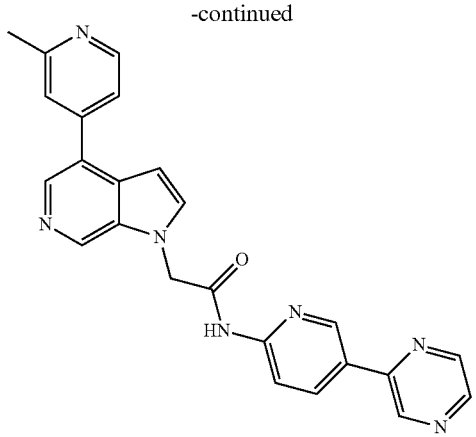
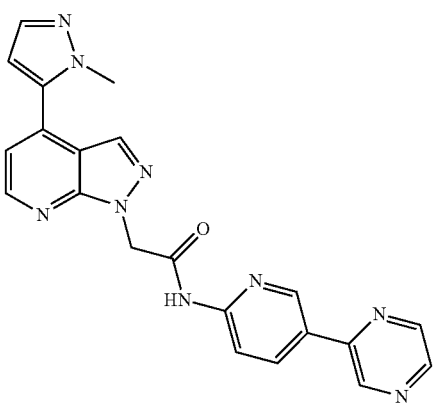
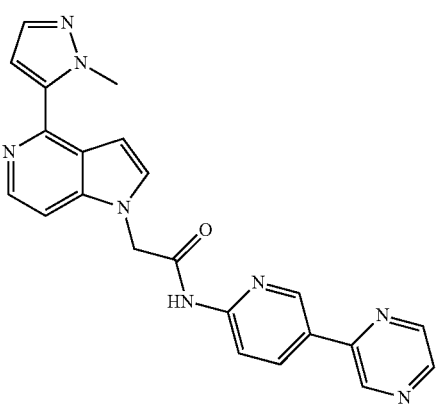
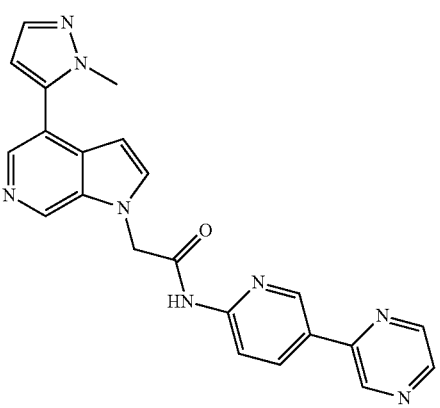

-continued
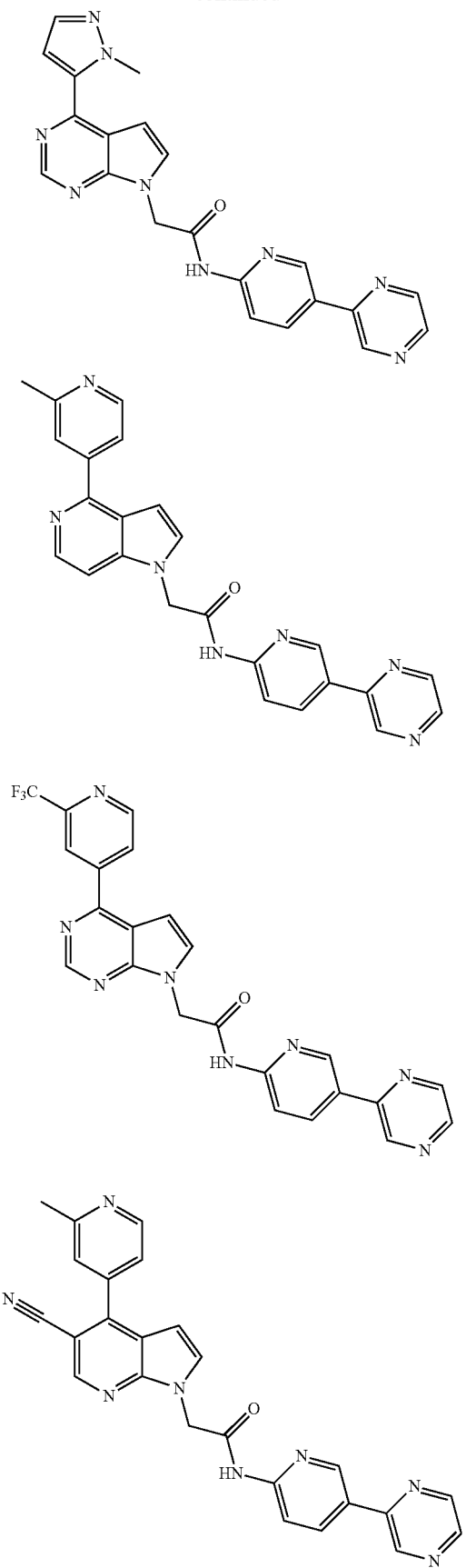
-continued
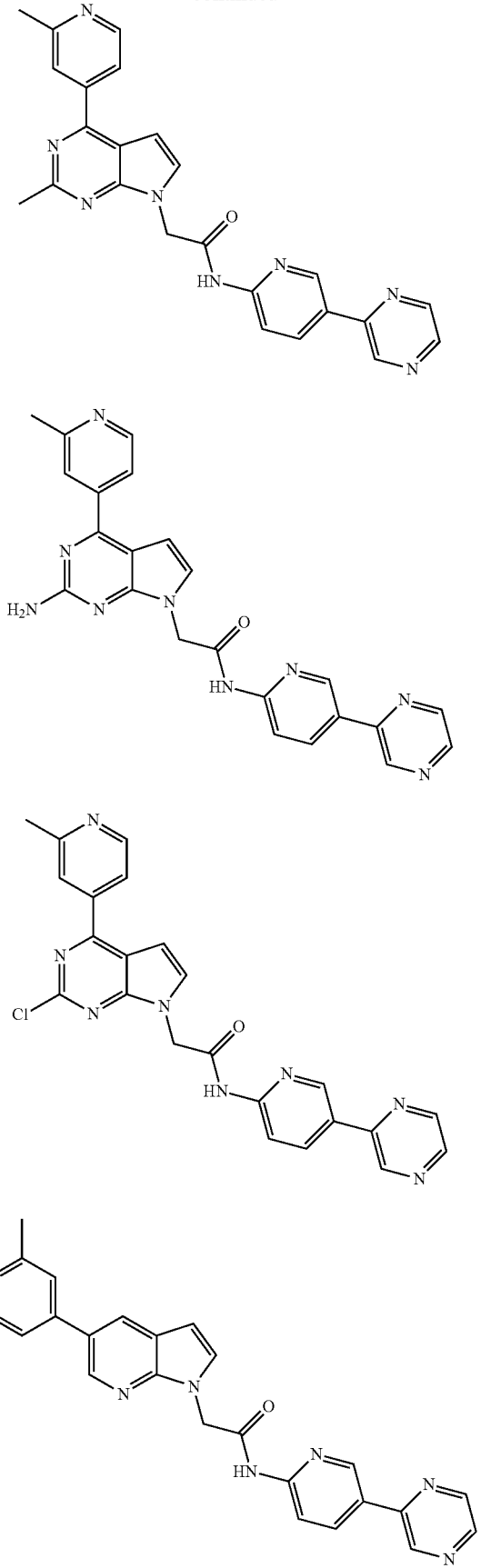

-continued
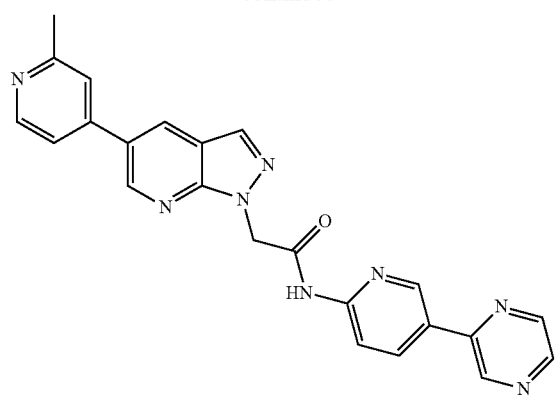
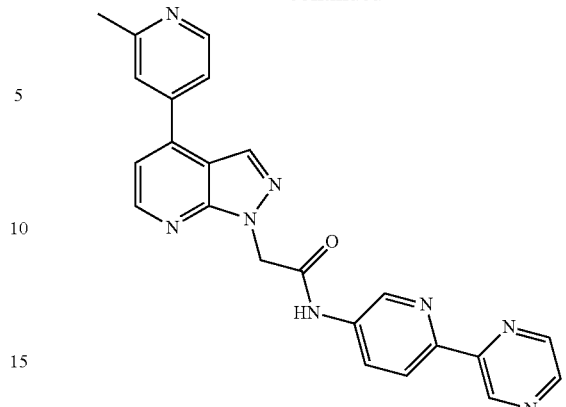
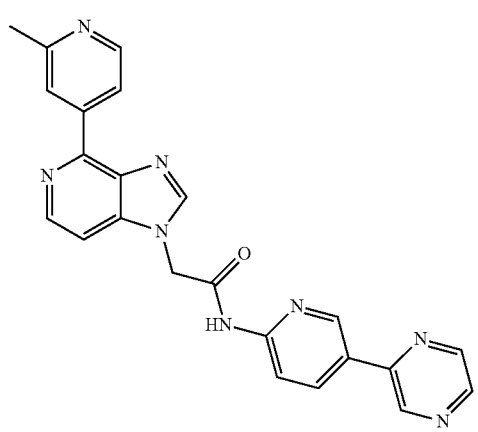
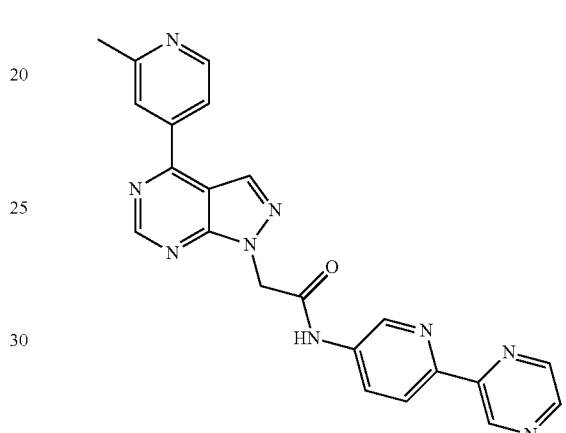
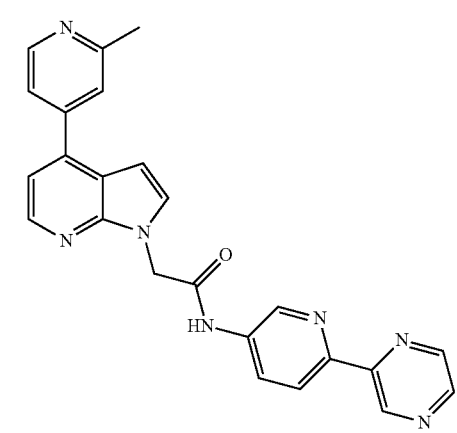
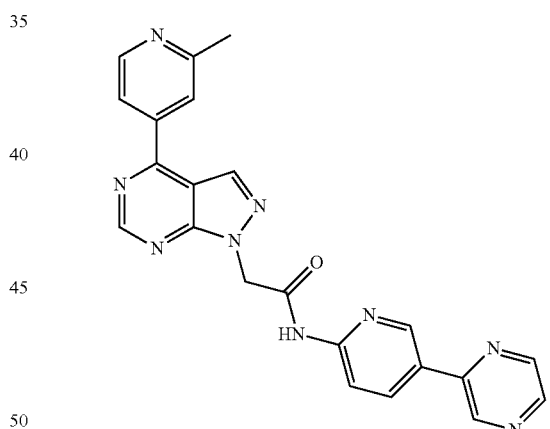
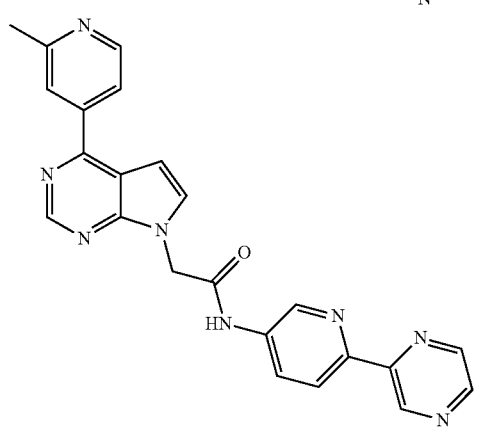
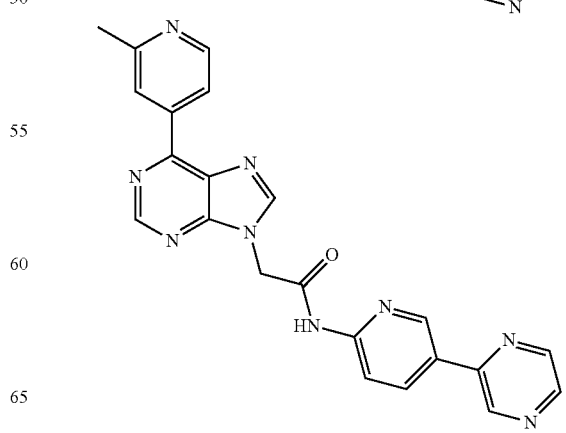

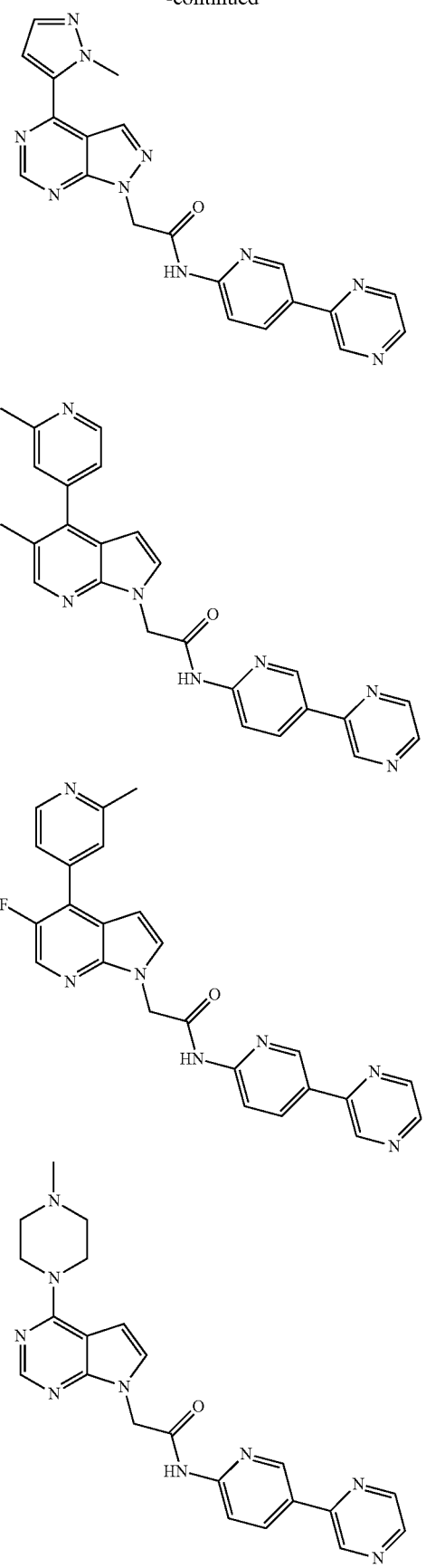
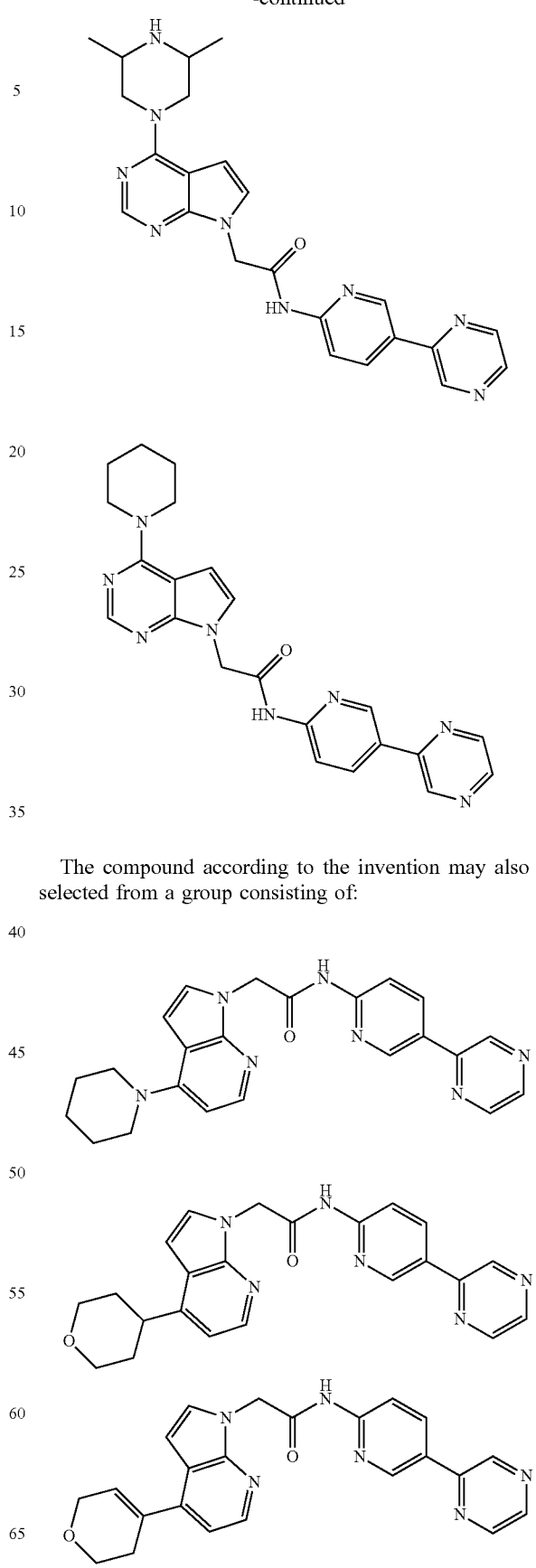
The compound according to the invention may also be selected from a group consisting of:

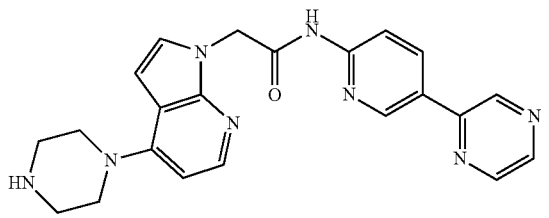
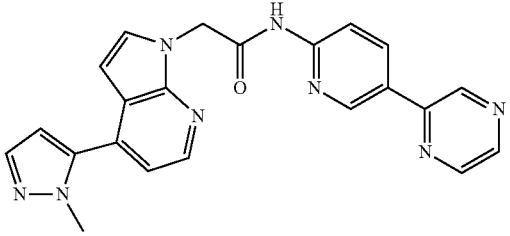
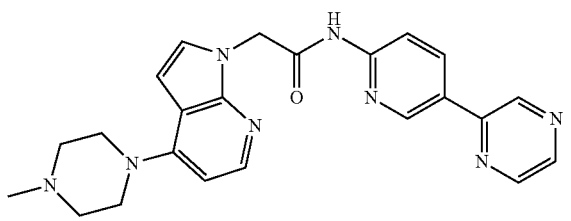
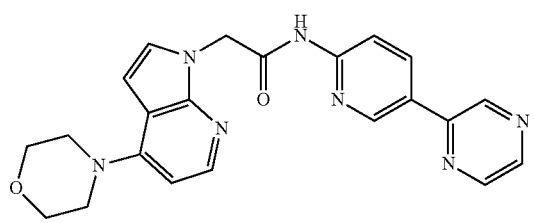
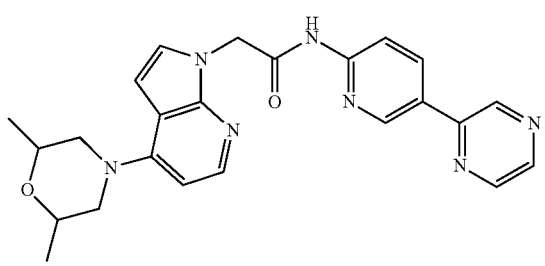
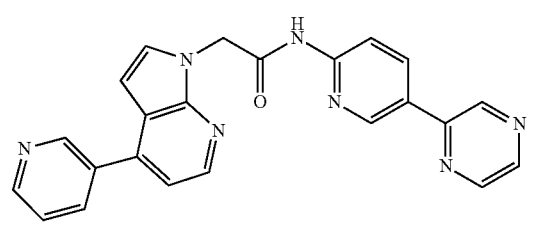
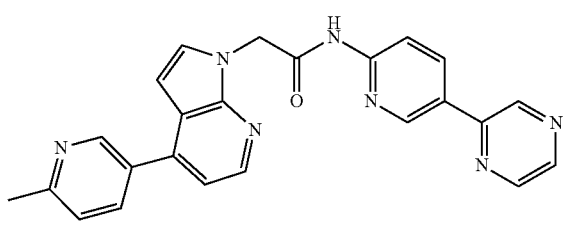
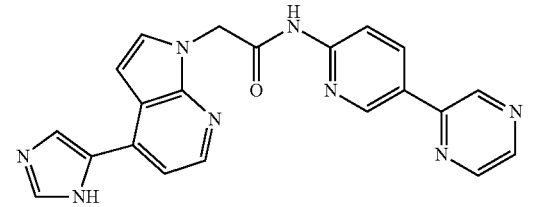

In accordance with another aspect, the present invention provides a compound of the present invention for use as a medicament.

In accordance with another aspect, the present invention provides a pharmaceutical formulation comprising a compound of the present invention and a pharmaceutically acceptable excipient.

In an embodiment the pharmaceutical composition may be a combination product comprising an additional pharmaceutically active agent. The additional pharmaceutically active agent may be an anti-tumor agent described below.

In accordance with another aspect, there is provided a compound of the present invention for use in the modulation of Wnt signalling. Optionally, the Wnt signalling is modulated by the inhibition of porcupine (Porcn). Modulation of Wnt signalling may include inhibition of paracrine signalling in the tissues surrounding tumours and autocrine and paracrine signalling in cancer cells In accordance with another aspect, there is provided a compound of the present invention for use in the treatment of a condition which can be modulated by inhibition of Porcn using a compound of the present invention. A compound of formula (I) may be for use in the treatment of a condition treatable by the inhibition of Porcn.

Porcn inhibition is relevant for the treatment of many different diseases associated with increased Wnt signalling. In embodiments the condition treatable by the modulation of Wnt signalling or the inhibition of Porcn may be selected from: cancer, sarcoma, melanoma, skin cancer, haematological tumors, lymphoma, carcinoma, and leukemia. Specific cancers, sarcomas, melanomas, skin cancers, haematological tumors, lymphoma, carcinoma and leukemia treatable by the modulation of Wnt signalling or the inhibition of Porcn may be selected from: esophageal squamous cell carcinoma, gastric cancer, glioblastomas, astrocytomas; retinoblastoma, osteosarcoma, chondosarcoma, Ewing's sarcoma, rabdomysarcoma, Wilm's tumor, basal cell carcinoma, non-small cell lung cancer, brain tumour, hormone refractory prostate cancer, prostate cancer, metastatic breast cancer, breast cancer, metastatic pancreatic cancer, pancreatic cancer, colorectal cancer, cervical cancer, head and neck squamous cell carcinoma and cancer of the head and neck.

Porcn inhibition is also relevant for the treatment of a condition treatable by the inhibition of Wnt ligand secretion selected from: skin fibrosis, idiopathic pulmonary fibrosis, renal interstitial fibrosis, liver fibrosis, proteinuria, kidney graft rejection, osteoarthritis, Parkinsons's disease, cystoid macular edema, uveitis associated cystoid macular edema, retinopathy, diabetic retinopathy and retinopathy of prematurity.

The invention contemplates methods of treating the above mentioned conditions and contemplates compounds of the invention for use in a method of treatment of the above mentioned conditions.

In an aspect of the invention, a compound of the invention may be for use in the treatment of a condition selected from: cancer, sarcoma, melanoma, skin cancer, haematological tumors, lymphoma, carcinoma, and leukemia. Specific cancer, sarcoma, melanoma, skin cancer, haematological tumors, lymphoma, carcinoma, and leukemia that may be treated by the compound of the invention may be selected from: esophageal squamous cell carcinoma, gastric cancer, glioblastomas, astrocytomas; retinoblastoma, osteosarcoma, chondosarcoma, Ewing's sarcoma, rabdomysarcoma, Wilm's tumor, basal cell carcinoma, non-small cell lung cancer, brain tumour, hormone refractory prostate cancer, prostate cancer, metastatic breast cancer, breast cancer, metastatic pancreatic cancer, pancreatic cancer, colorectal cancer, cervical cancer, head and neck squamous cell carcinoma and cancer of the head and neck.

The compound of the invention also may be for use in the treatment of a condition selected from: skin fibrosis, idiopathic pulmonary fibrosis, renal interstitial fibrosis, liver fibrosis, proteinuria, kidney graft rejection, osteoarthritis, Parkinsons's disease, cystoid macular edema, uveitis associated cystoid macular edema, retinopathy, diabetic retinopathy and retinopathy of prematurity.

In an aspect of the invention there is provided a method of treatment of a condition which is modulated by Wnt signalling, wherein the method comprises administering a therapeutic amount of a compound of the invention, to a patient in need thereof. In an embodiment of the invention there is provided a method of treatment of a condition which is modulated by Porcn.

The method of treatment may be a method of treating a condition treatable by the modulation of Wnt signalling or Porcn. These conditions are described above in relation to conditions treatable by the inhibition of Porcn.

In an aspect of the invention there is provided a method of treatment of a condition selected from: cancer, sarcoma, melanoma, skin cancer, haematological tumors, lymphoma, carcinoma, and leukemia, wherein the method comprises administering a therapeutic amount of a compound of the invention, to a patient in need thereof. Specific cancer, sarcoma, melanoma, skin cancer, haematological tumors, lymphoma, carcinoma, and leukemia that may be treated by the method of treatment may be selected from: esophageal squamous cell carcinoma, gastric cancer, glioblastomas, astrocytomas; retinoblastoma, osteosarcoma, chondosarcoma, Ewing's sarcoma, rabdomysarcoma, Wilm's tumor, basal cell carcinoma, non-small cell lung cancer, brain tumour, hormone refractory prostate cancer, prostate cancer, metastatic breast cancer, breast cancer, metastatic pancreatic cancer, pancreatic cancer, colorectal cancer, cervical cancer, head and neck squamous cell carcinoma and cancer of the head and neck.

The method of treatment also may be the treatment of a condition selected from: skin fibrosis, idiopathic pulmonary fibrosis, renal interstitial fibrosis, liver fibrosis, proteinuria, kidney graft rejection, osteoarthritis, Parkinson's disease, cystoid macular edema, uveitis associated cystoid macular edema, retinopathy, diabetic retinopathy and retinopathy of prematurity.

In an aspect of the invention there is provided a use of a compound of the invention in the manufacture of a medicament for the treatment of a condition which is modulated by Porcn. The condition may be any of the conditions mentioned above.

Aberrant Wnt signalling may be associated with a condition selected from: non small cell lung cancer (NSCLC); chronic lymphocytic leukemia (CLL); gastric cancer; head and neck squamous cell carcinoma (HNSCC); colorectal cancer; ovarian cancer; basal cell carcinoma (BCC); breast cancer; bladder cancer; mesothelioma colorectal; prostate cancer; non-small cell lung cancer; lung cancer; osteosarcoma; Frz overexpression; has been associated with cancers such as prostate; colorectal; ovarian cancer; gastric; overexpression of Wnt signaling pathway components such as dishevelled; prostate cancer; breast cancer; mesothelioma; cervical; Frat-1 overexpression; pancreatic cancer; esophageal cancer; cervical cancer; breast cancer; and gastric cancer; Axin loss of function (LOF); hepatocellular cancer; medulloblastoma; gastric cancer; colorectal cancer; intestinal carcinoid; ovarian cancer; pulmonary adenocarcinoma; endometrial cancer; hepatocellular; hepatoblastoma; medulloblastoma; pancreatic cancer; thyroid cancer; prostate cancer; melanoma; pilomatricoma; Wilms' tumor; pancreatoblastomas; liposarcomas; juvenile nasopharyngeal angiofibromas; desmoid; synovial sarcoma; melanoma; leukemia; multiple myeloma; brain tumors, such as gliomas, astrocytomas, meningiomas, schwannomas, pituitary tumors, primitive neuroectodermal tumors (PNET), medulloblastomas, craniopharyngioma, pineal region tumors, and non cancerous neurofibromatoses;

Inhibition of Wnt signaling with the Wnt antagonists of the present invention may be therapeutic in the treatment of disorders resulting from dysfunctional hematopoieses, such as leukemias and various blood related cancers, such as acute, chronic, lymphoid and myelogenous leukemias, myelodysplastic syndrome and myeloproliferative disorders. These include myeloma, lymphoma (e.g., Hodgkin's and non-Hodgkin's) chronic and nonprogressive anemia, progressive and symptomatic blood cell deficiencies, polycythemia vera, essential or primary thrombocythemia, idiopathic myelofibrosis, chronic myelomonocytic leukemia (CMML), mantle cell lymphoma, cutaneous T-cell lymphoma, and Waldenstrom macro globinemia.

Other disorders associated with aberrant Wnt signaling, include but are not limited to osteoporosis, osteoarthritis, polycystic kidney disease, diabetes, schizophrenia, vascular disease, cardiac disease, non-oncogenic proliferative diseases, and neurodegenerative diseases such as Alzheimer's disease.

Aberrant Wnt signalling may be associated with a cancer selected from: brain; lung; colon; epidermoid; squamous cell; bladder; gastric; pancreatic; breast; head and neck; renal; kidney; liver; ovarian; prostate; uterine; oesophageal; testicular; gynaecological; thyroid; melanoma; acute myeloid leukemia; chronic myelogenous leukemia; MCL Kaposi's sarcoma;

Aberrant Wnt signalling may be associated with an inflammatory disease selected from: multiple sclerosis; rheumatoid arthritis; systemic lupus; inflammatory bowel disease; osteoarthritis; Alzheimer's;

DETAILED DESCRIPTION

Given below are definitions of terms used in this application. Any term not defined herein takes the normal meaning as the skilled person would understand the term.

The term "halo" refers to one of the halogens, group 17 of the periodic table. In particular the term refers to fluorine, chlorine, bromine and iodine. Preferably, the term refers to fluorine or chlorine.

The term "$C_{1-4}$ alkyl" refers to a linear or branched hydrocarbon chain containing 1, 2, 3, 4, 5 or 6 carbon atoms, for example methyl, ethyl, n-propyl, iso-propyl, n-butyl, sec-butyl, tert-butyl, n-pentyl and n-hexyl. Alkylene groups may likewise be linear or branched and may have two places of attachment to the remainder of the molecule. Furthermore, an alkylene group may, for example, correspond to one of those alkyl groups listed in this paragraph. The alkyl and alkylene groups may be unsubstituted or substituted by one or more substituents. Possible substituents are described below. Substituents for the alkyl group may be halogen, e.g. fluorine, chlorine, bromine and iodine, OH, $C_{1-6}$ alkoxy.

The term "$C_{1-4}$ alkoxy" refers to an alkyl group which is attached to a molecule via oxygen. This includes moieties where the alkyl part may be linear or branched and may contain 1, 2, 3, 4, 5 or 6 carbon atoms, for example methyl, ethyl, n-propyl, iso-propyl, n-butyl, sec-butyl, tert-butyl, n-pentyl and n-hexyl. Therefore, the alkoxy group may be methoxy, ethoxy, n-propoxy, iso-propoxy, n-butoxy, sec-butoxy, tert-butoxy, n-pentoxy and n-hexoxy. The alkyl part of the alkoxy group may be unsubstituted or substituted by one or more substituents. Possible substituents are described below. Substituents for the alkyl group may be halogen, e.g. fluorine, chlorine, bromine and iodine, OH, $C_{1-6}$ alkoxy.

The term "$C_{1-4}$ haloalkyl" refers to a hydrocarbon chain substituted with at least one halogen atom independently chosen at each occurrence, for example fluorine, chlorine, bromine and iodine. The halogen atom may be present at any position on the hydrocarbon chain. For example, $C_{1-6}$ haloalkyl may refer to chloromethyl, fluoromethyl, trifluoromethyl, chloroethyl e.g. 1-chloromethyl and 2-chloroethyl, trichloroethyl e.g. 1,2,2-trichloroethyl, 2,2,2-trichloroethyl, fluoroethyl e.g. 1-fluoromethyl and 2-fluoroethyl, trifluoroethyl e.g. 1,2,2-trifluoroethyl and 2,2,2-trifluoroethyl, chloropropyl, trichloropropyl, fluoropropyl, trifluoropropyl.

The term "$C_{2-6}$ alkenyl" refers to a branched or linear hydrocarbon chain containing at least one double bond and having 2, 3, 4, 5 or 6 carbon atoms. The double bond(s) may be present as the E or Z isomer. The double bond may be at any possible position of the hydrocarbon chain. For example, the "$C_{2-6}$ alkenyl" may be ethenyl, propenyl, butenyl, butadienyl, pentenyl, pentadienyl, hexenyl and hexadienyl.

The term "$C_{2-6}$ alkynyl" refers to a branched or linear hydrocarbon chain containing at least one triple bond and having 2, 3, 4, 5 or 6 carbon atoms. The triple bond may be at any possible position of the hydrocarbon chain. For example, the "$C_{2-6}$ alkynyl" may be ethynyl, propynyl, butynyl, pentynyl and hexynyl.

The term "$C_{1-6}$ heteroalkyl" refers to a branched or linear hydrocarbon chain containing 1, 2, 3, 4, 5, or 6 carbon atoms and at least one heteroatom selected from N, O and S positioned between any carbon in the chain or at an end of the chain. For example, the hydrocarbon chain may contain one or two heteroatoms. The $C_{1-6}$ heteroalkyl may be bonded to the rest of the molecule through a carbon or a heteroatom. For example, the "$C_{1-6}$ heteroalkyl" may be $C_{1-6}$ N-alkyl, $C_{1-6}$ N,N-alkyl, or $C_{1-6}$ O-alkyl.

The term "carbocyclic" refers to a saturated or unsaturated carbon containing ring system. A "carbocyclic" system may be monocyclic or a fused polycyclic ring system, for example, bicyclic or tricyclic. A "carbocyclic" moiety may contain from 3 to 14 carbon atoms, for example, 3 to 8 carbon atoms in a monocyclic system and 7 to 14 carbon atoms in a polycyclic system. "Carbocyclic" encompasses cycloalkyl moieties, cycloalkenyl moieties, aryl ring systems and fused ring systems including an aromatic portion.

The term "heterocyclic" refers to a saturated or unsaturated ring system containing at least one heteroatom selected from N, O or S. A "heterocyclic" system may contain 1, 2, 3 or 4 heteroatoms, for example 1 or 2. A "heterocyclic" system may be monocyclic or a fused polycyclic ring system, for example, bicyclic or tricyclic. A "heterocyclic" moiety may contain from 3 to 14 carbon atoms, for example, 3 to 8 carbon atoms in a monocyclic system and 7 to 14 carbon atoms in a polycyclic system. "Heterocyclic" encompasses heterocycloalkyl moieties, heterocycloalkenyl moieties and heteroaromatic moieties. For example, the heterocyclic group may be: oxirane, aziridine, azetidine, oxetane, tetrahydrofuran, pyrrolidine, imidazolidine, succinimide, pyrazolidine, oxazolidine, isoxazolidine, thiazolidine, isothiazolidine, piperidine, morpholine, thiomorpholine, piperazine, and tetrahydropyran.

The term "$C_{3-6}$ cycloalkyl" refers to a saturated hydrocarbon ring system containing 3, 4, 5, 6, 7 or 8 carbon atoms. For example, the "$C_{3-6}$ cycloalkyl" may be cyclopropyl, cyclobutyl, cyclopentyl, cyclohexyl, cycloheptyl and cyclooctyl.

The term "$C_{3-6}$ cycloalkenyl" refers to an unsaturated hydrocarbon ring system containing 3, 4, 5, 6, 7 or 8 carbon atoms that is not aromatic. The ring may contain more than one double bond provided that the ring system is not aromatic. For example, the "$C_{3-6}$ cycloalkyl" may be cyclopropenyl, cyclobutenyl, cyclopentenyl, cyclopentadienyl, cyclohexenyl, cyclohexadienly, cycloheptenyl, cycloheptadiene, cyclooctenyl and cycloatadienyl.

The term "$C_{3-6}$ heterocycloalkyl" refers to a saturated hydrocarbon ring system containing 3, 4, 5, 6, 7 or 8 carbon atoms and at least one heteroatom within the ring selected from N, O and S. For example there may be 1, 2 or 3 heteroatoms, optionally 1 or 2. The "$C_{3-6}$ heterocycloalkyl" may be bonded to the rest of the molecule through any carbon atom or heteroatom. The "$C_{3-6}$ heterocycloalkyl" may have one or more, e.g. one or two, bonds to the rest of the molecule: these bonds may be through any of the atoms in the ring. For example, the "$C_{3-6}$ heterocycloalkyl" may be oxirane, aziridine, azetidine, oxetane, tetrahydrofuran, pyrrolidine, imidazolidine, succinimide, pyrazolidine, oxazolidine, isoxazolidine, thiazolidine, isothiazolidine, piperidine, morpholine, thiomorpholine, piperazine, and tetrahydropyran.

The term "$C_{3-6}$ heterocycloalkenyl" refers to an unsaturated hydrocarbon ring system, that is not aromatic, containing 3, 4, 5, 6, 7 or 8 carbon atoms and at least one heteroatom within the ring selected from N, O and S. For example there may be 1, 2 or 3 heteroatoms, optionally 1 or 2. The "$C_{3-6}$ heterocycloalkenyl" may be bonded to the rest of the molecule through any carbon atom or heteroatom. The "$C_{3-6}$ heterocycloalkenyl" may have one or more, e.g. one or two, bonds to the rest of the molecule: these bonds may be through any of the atoms in the ring. For example, the "$C_{3-6}$ heterocycloalkyl" may be tetrahydropyridine, dihydropyran, dihydrofuran, pyrroline.

The term "aromatic" when applied to a substituent as a whole means a single ring or polycyclic ring system with 4n+2 electrons in a conjugated τ system within the ring or ring system where all atoms contributing to the conjugated τ system are in the same plane.

The term "aryl" refers to an aromatic hydrocarbon ring system. The ring system has 4n+2 electrons in a conjugated τ system within a ring where all atoms contributing to the conjugated τ system are in the same plane. For example, the "aryl" may be phenyl and naphthyl. The aryl system itself may be substituted with other groups.

The term "heteroaryl" refers to an aromatic hydrocarbon ring system with at least one heteroatom within a single ring or within a fused ring system, selected from O, N and S. The ring or ring system has 4n+2 electrons in a conjugated π system where all atoms contributing to the conjugated π system are in the same plane. For example, the "heteroaryl" may be imidazole, thiene, furane, thianthrene, pyrrol, benzimidazole, pyrazole, pyrazine, pyridine, pyrimidine and indole.

The term "alkaryl" refers to an aryl group, as defined above, bonded to a $C_{1-4}$ alkyl, where the $C_{1-4}$ alkyl group provides attachment to the remainder of the molecule.

The term "alkheteroaryl" refers to a heteroaryl group, as defined above, bonded to a $C_{1-4}$ alkyl, where the alkyl group provides attachment to the remainder of the molecule.

The term "halogen" herein includes reference to F, Cl, Br and I. Halogen may be Cl. Halogen may be F.

A bond terminating in a "⌇" represents that the bond is connected to another atom that is not shown in the structure. A bond terminating inside a cyclic structure and not terminating at an atom of the ring structure represents that the bond may be connected to any of the atoms in the ring structure where allowed by valency.

Where a moiety is substituted, it may be substituted at any point on the moiety where chemically possible and consistent with atomic valency requirements. The moiety may be substituted by one or more substituents, e.g. 1, 2, 3 or 4 substituents; optionally there are 1 or 2 substituents on a group. Where there are two or more substituents, the substituents may be the same or different. The substituent(s) may be selected from: OH, NHR, amidino, guanidino, hydroxyguanidino, formamidino, isothioureido, ureido, mercapto, C(O)H, acyl, acyloxy, carboxy, sulfo, sulfamoyl, carbamoyl, cyano, azo, nitro, halo, $C_{1-6}$ alkyl, $C_{1-6}$ alkoxy, $C_{1-6}$ haloalkyl, $C_{3-8}$ cycloalkyl, $C_{2-6}$ alkenyl, $C_{2-6}$ alkynyl, aryl, heteroaryl or alkaryl. Where the group to be substituted is an alkyl group the substituent may be =O. R may be selected from H, $C_{1-6}$ alkyl, $C_{3-8}$ cycloalkyl, phenyl, benzyl or phenethyl group, e.g. R is H or $C_{1-3}$ alkyl. Where the moiety is substituted with two or more substituents and two of the substituents are adjacent the adjacent substituents may form a $C_{4-8}$ ring along with the atoms of the moiety on which the substituents are substituted, wherein the $C_{4-8}$ ring is a saturated or unsaturated hydrocarbon ring with 4, 5, 6, 7, or 8 carbon atoms or a saturated or unsaturated hydrocarbon ring with 4, 5, 6, 7, or 8 carbon atoms and 1, 2 or 3 heteroatoms.

Substituents are only present at positions where they are chemically possible, the person skilled in the art being able to decide (either experimentally or theoretically) without inappropriate effort which substitutions are chemically possible and which are not.

Ortho, meta and para substitution are well understood terms in the art. For the absence of doubt, "ortho" substitution is a substitution pattern where adjacent carbons possess a substituent, whether a simple group, for example the fluoro group in the example below, or other portions of the molecule, as indicated by the bond ending in "⌇".

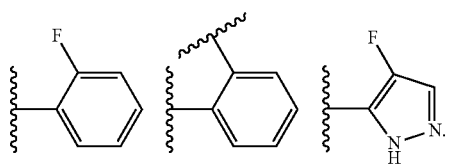

"Meta" substitution is a substitution pattern where two substituents are on carbons one carbon removed from each other, i.e with a single carbon atom between the substituted carbons. In other words there is a substituent on the second atom away from the atom with another substituent. For example the groups below are meta substituted.

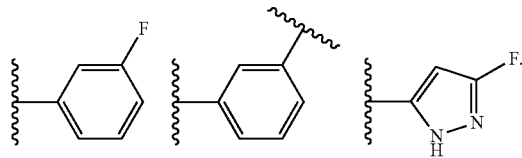

"Para" substitution is a substitution pattern where two substituents are on carbons two carbons removed from each other, i.e with two carbon atoms between the substituted carbons. In other words there is a substituent on the third atom away from the atom with another substituent. For example the groups below are para substituted.

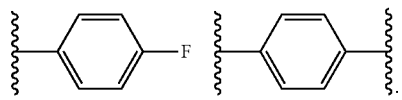

By "acyl" is meant an organic radical derived from, for example, an organic acid by the removal of the hydroxyl group, e.g. a radical having the formula R—C(O)—, where R may be selected from H, $C_{1-6}$ alkyl, $C_{3-8}$ cycloalkyl, phenyl, benzyl or phenethyl group, eg R is H or $C_{1-3}$ alkyl. In one embodiment acyl is alkyl-carbonyl. Examples of acyl groups include, but are not limited to, formyl, acetyl, propionyl and butyryl. A particular acyl group is acetyl.

Throughout the description the disclosure of a compound also encompasses pharmaceutically acceptable salts, solvates and stereoisomers thereof. Where a compound has a stereocentre, both (R) and (S) stereoisomers are contemplated by the invention, equally mixtures of stereoisomers or a racemic mixture are completed by the present application. Where a compound of the invention has two or more stereocentres any combination of (R) and (S) stereoisomers is contemplated. The combination of (R) and (S) stereoisomers may result in a diastereomeric mixture or a single diastereoisomer. The compounds of the invention may be present as a single stereoisomer or may be mixtures of stereoisomers, for example racemic mixtures and other enantiomeric mixtures, and diasteroemeric mixtures. Where the mixture is a mixture of enantiomers the enantiomeric excess may be any of those disclosed above. Where the compound is a single stereoisomer the compounds may still contain other diastereoisomers or enantiomers as impurities. Hence a single stereoisomer does not necessarily have an enantiomeric excess (e.e.) or diastereomeric excess (d.e.) of 100% but could have an e.e. or d.e. of about at least 85%

The invention contemplates pharmaceutically acceptable salts of the compounds of the invention. These may include the acid addition and base salts of the compounds. These may be acid addition and base salts of the compounds. In addition the invention contemplates solvates of the compounds. These may be hydrates or other solvated forms of the compound.

Suitable acid addition salts are formed from acids which form non-toxic salts. Examples include the acetate, aspartate, benzoate, besylate, bicarbonate/carbonate, bisulfate/sulfate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulfate, naphthylate, 1,5-naphthalenedisulfonate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts.

Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts. Hemisalts of acids and bases may also be formed, for example, hemisulfate and hemicalcium salts. For a review on suitable salts, see "Handbook of Pharmaceutical Salts: Properties, Selection, and Use" by Stahl and Wermuth (Wiley-VCH, Weinheim, Germany, 2002).

Pharmaceutically acceptable salts of compounds of formula (I) may be prepared by one or more of three methods:
(i) by reacting the compound of the invention with the desired acid or base;
(ii) by removing an acid- or base-labile protecting group from a suitable precursor of the compound of the invention or by ring-opening a suitable cyclic precursor, for example, a lactone or lactam, using the desired acid or base; or
(iii) by converting one salt of the compound of the invention to another by reaction with an appropriate acid or base or by means of a suitable ion exchange column.

All three reactions are typically carried out in solution. The resulting salt may precipitate out and be collected by filtration or may be recovered by evaporation of the solvent. The degree of ionisation in the resulting salt may vary from completely ionised to almost non-ionised.

The compounds of the invention may exist in both unsolvated and solvated forms. The term 'solvate' is used herein to describe a molecular complex comprising the compound of the invention and a stoichiometric amount of one or more pharmaceutically acceptable solvent molecules, for example, ethanol. The term 'hydrate' is employed when said solvent is water.

Included within the scope of the invention are complexes such as clathrates, drug-host inclusion complexes wherein, in contrast to the aforementioned solvates, the drug and host are present in stoichiometric or non-stoichiometric amounts. Also included are complexes of the drug containing two or more organic and/or inorganic components which may be in stoichiometric or non-stoichiometric amounts. The resulting complexes may be ionised, partially ionised, or non-ionised. For a review of such complexes, see J Pharm Sci, 64 (8), 1269-1288 by Haleblian (August 1975).

Hereinafter all references to compounds of any formula include references to salts, solvates and complexes thereof and to solvates and complexes of salts thereof.

The compounds of the invention include compounds of a number of formula as herein defined, including all polymorphs and crystal habits thereof, prodrugs and isomers thereof (including optical, geometric and tautomeric isomers) as hereinafter defined and isotopically-labelled compounds of the invention.

The present invention also includes all pharmaceutically acceptable isotopically-labelled compounds of the invention wherein one or more atoms are replaced by atoms having the same atomic number, but an atomic mass or mass number different from the atomic mass or mass number most commonly found in nature.

Examples of isotopes suitable for inclusion in the compounds of the invention include isotopes of hydrogen, such as $^{2}H$ and $^{3}H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulphur, such as $^{35}S$.

Certain isotopically-labelled compounds, for example, those incorporating a radioactive isotope, are useful in drug and/or substrate tissue distribution studies. The radioactive isotopes tritium, i.e. $^{3}H$, and carbon-14, i.e. $^{14}C$, are particularly useful for this purpose in view of their ease of incorporation and ready means of detection.

Substitution with heavier isotopes such as deuterium, i.e. $^{2}H$, may afford certain therapeutic advantages resulting from greater metabolic stability, for example, increased in vivo half-life or reduced dosage requirements, and hence may be preferred in some circumstances.

Before purification, the compounds of the present invention may exist as a mixture of enantiomers depending on the synthetic procedure used. The enantiomers can be separated by conventional techniques known in the art. Thus the invention covers individual enantiomers as well as mixtures thereof.

For some of the steps of the process of preparation of the compounds of the invention, it may be necessary to protect potential reactive functions that are not wished to react, and to cleave said protecting groups in consequence. In such a case, any compatible protecting radical can be used. In particular methods of protection and deprotection such as those described by T. W. GREENE (Protective Groups in Organic Synthesis, A. Wiley-Interscience Publication, 1981) or by P. J. Kocienski (Protecting groups, Georg Thieme Verlag, 1994), can be used. All of the above reactions and the preparations of novel starting materials used in the preceding methods are conventional and appropriate reagents and reaction conditions for their performance or preparation as well as procedures for isolating the desired products will be well-known to those skilled in the art with reference to literature precedents and the examples and preparations hereto.

Also, the compounds of the present invention as well as intermediates for the preparation thereof can be purified according to various well-known methods, such as for example crystallization or chromatography.

One or more compounds of the invention may be combined with one or more pharmaceutical agents, for example anti-viral agents, chemotherapeutics, anti-cancer agents, immune enhancers, immunosuppressants, anti-tumour vaccines, anti-viral vaccines, cytokine therapy, or tyrosine kinase inhibitors, for the treatment of conditions modulated by the inhibition of Porcn, for example cancer, sarcoma, melanoma, skin cancer, haematological tumors, lymphoma, carcinoma, leukemia, central nervous system disorders, inflammation and immunological diseases The method of treatment or the compound for use in the treatment of cancer, sarcoma, melanoma, skin cancer, haematological tumors, lymphoma, carcinoma, leukemia, central nervous system disorders, inflammation and immunological diseases as defined hereinbefore may be applied as a sole therapy or be a combination therapy with an additional active agent.

The method of treatment or the compound for use in the treatment of cancer, sarcoma, melanoma, skin cancer, haematological tumors, lymphoma, carcinoma, leukemia, and central nervous system disorders may involve, in addition to the compound of the invention, conventional surgery or radiotherapy or chemotherapy. Such chemotherapy may include one or more of the following categories of antitumor agents:

(i) antiproliferative/antineoplastic drugs and combinations thereof, such as alkylating agents (for example cis-platin, oxaliplatin, carboplatin, cyclophosphamide, nitrogen mustard, uracil mustard, bendamustin, melphalan, chlorambucil, chlormethine, busulphan, temozolamide, nitrosoureas, ifosamide, melphalan, pipobroman, triethylene-melamine, triethylenethiophoporamine, carmustine, lomustine, stroptozocin and dacarbazine); antimetabolites (for example gemcitabine and antifolates such as fluoropyrimidines like 5-fluorouracil and tegafur, raltitrexed, methotrexate, pemetrexed, cytosine arabinoside, floxuridine, cytarabine, 6-mercaptopurine, 6-thioguanine, fludarabine phosphate, pentostatine, and gemcitabine and hydroxyurea); antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere and polokinase inhibitors); proteasome inhibitors, for example carfilzomib and bortezomib; interferon therapy; and topoisomerase inhibitors (for example epipodophyllotoxins like etoposide and teniposide, amsacrine, topotecan, mitoxantrone and camptothecin); bleomcin, dactinomycin, daunorubicin, doxorubicin, epirubicin, idarubicin, ara-C, paclitaxel (Taxol™), nabpaclitaxel, docetaxel, mithramycin, deoxyco-formycin, mitomycin-C, L-asparaginase, interferons (especially IFN-a), etoposide, and teniposide;

(ii) cytostatic agents such as antiestrogens (for example tamoxifen, fulvestrant, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride; and navelbene, CPT-II, anastrazole, letrazole, capecitabine, reloxafme, cyclophosphamide, ifosamide, and droloxafine;

(iii) anti-invasion agents, for example dasatinib and bosutinib (SKI-606), and metalloproteinase inhibitors, inhibitors of urokinase plasminogen activator receptor function or antibodies to Heparanase;

(iv) inhibitors of growth factor function: for example such inhibitors include growth factor antibodies and growth factor receptor antibodies, for example the anti-erbB2 antibody trastuzumab [Herceptin™], the anti-EGFR antibody panitumumab, the anti-erbB1 antibody cetuximab, tyrosine kinase inhibitors, for example inhibitors of the epidermal growth factor family (for example EGFR family tyrosine kinase inhibitors such as gefitinib, erlotinib, 6-acrylamido-N-(3-chloro-4-fluorophenyl)-7-(3-morpholinopropoxy)-quinazolin-4-amine (CI 1033), erbB2 tyrosine kinase inhibitors such as lapatinib) and antibodies to costimulatory molecules such as CTLA-4, 4-IBB and PD-I, or antibodies to cytokines (IL-10, TGF-beta); inhibitors of the hepatocyte growth factor family; inhibitors of the insulin growth factor family; modulators of protein regulators of cell apoptosis (for example Bcl-2 inhibitors); inhibitors of the platelet-derived growth factor family such as imatinib and/or nilotinib (AMN107); inhibitors of serine/threonine kinases (for example Ras/Raf signalling inhibitors such as farnesyl transferase inhibitors, for example sorafenib, tipifarnib and lonafarnib), inhibitors of cell signalling through MEK and/or AKT kinases, c-kit inhibitors, abl kinase inhibitors, PI3 kinase inhibitors, Plt3 kinase inhibitors, CSF-1R kinase inhibitors, IGF receptor, kinase inhibitors; aurora kinase inhibitors and cyclin dependent kinase inhibitors such as CDK2 and/or CDK4 inhibitors; and CCR2, CCR4 or CCR6 modulator;

(v) antiangiogenic agents such as those which inhibit the effects of vascular endothelial growth factor, [for example the anti-vascular endothelial cell growth factor antibody bevacizumab (Avastin™); thalidomide; lenalidomide; and for example, a VEGF receptor tyrosine kinase inhibitor such as vandetanib, vatalanib, sunitinib, axitinib and pazopanib;

(vi) gene therapy approaches, including for example approaches to replace aberrant genes such as aberrant p53 or aberrant BRCA1 or BRCA2;

(vii) immunotherapy approaches, including for example antibody therapy such as alemtuzumab, rituximab, ibritumomab tiuxetan (Zevalin®) and ofatumumab; interferons such as interferon α; interleukins such as IL-2 (aldesleukin); interleukin inhibitors for example IRAK4 inhibitors; cancer vaccines including prophylactic and treatment vaccines such as HPV vaccines, for example Gardasil, Cervarix, Oncophage and Sipuleucel-T (Provenge); gp100; dendritic cell-based vaccines (such as Ad.p53 DC); and toll-like receptor modulators for example TLR-7 or TLR-9 agonists; and (viii) cytotoxic agents for example fludaribine (fludara), cladribine, pentostatin (Nipent™);

(ix) steroids such as corticosteroids, including glucocorticoids and mineralocorticoids, for example aclometasone, aclometasone dipropionate, aldosterone, amcinonide, beclomethasone, beclomethasone dipropionate, betamethasone, betamethasone dipropionate, betamethasone sodium phosphate, betamethasone valerate, budesonide, clobetasone, clobetasone butyrate, clobetasol propionate, coprednol, cortisone, cortisone acetate, cortivazol, deoxycortone, desonide, desoximetasone, dexamethasone, dexamethasone sodium phosphate, dexamethasone isonicotinate, difluorocortolone, fluclorolone, flumethasone, flunisolide, fluocinolone, fluocinolone acetonide, fluocinonide, fluocortin butyl, fluorocortisone, fluorocortolone, fluocortolone caproate, fluocortolone pivalate, fluorometholone, fluprednidene, fluprednidene acetate, flurandrenolone, fluticasone, fluticasone propionate, halcinonide, hydrocortisone, hydrocortisone acetate, hydrocortisone butyrate, hydrocortisone aceponate, hydrocortisone buteprate, hydrocortisone valerate, icomethasone, icomethasone enbutate, meprednisone, methylprednisolone, mometasone paramethasone, mometasone furoate monohydrate, prednicarbate, prednisolone, prednisone, tixocortol, tixocortol pivalate, triamcinolone, triamcinolone acetonide, triamcinolone alcohol and their respective pharmaceutically acceptable derivatives. A combination of steroids may be used, for example a combination of two or more steroids mentioned in this paragraph;

(x) targeted therapies, for example PI3Kd inhibitors, for example idelalisib and perifosine; PD-1, PD-L1, PD-L2 and CTL4-A modulators, antibodies and vaccines; IDO inhibitors (such as indoximod); anti-PD-1 monoclonal antibodies (such as MK-3475 and nivolumab); anti-PDL1 monoclonal antibodies (such as MEDI-4736 and RG-7446); anti-PDL2 monoclonal antibodies; and anti-CTLA-4 antibodies (such as ipilimumab);

(xi) anti-viral agents such as nucleotide reverse transcriptase inhibitors (for example, zidovudine, didanosine, zalcitabine, stavudine, lamivudine, abacavir, adefovir diproxoxil, lobucavir, BCH-10652, emitricitabine, beta-L-FD4 (also called 3'-dicleoxy-5-fluoro-cytidine), (−)-beta-D-2,6-diamino-purine dioxolane, and lodenasine), non-nucleoside reverse transcriptase inhibitors (for example, nevirapine, delaviradine, efavirenz, PNU-142721, AG-1549, MKC-442 (1-ethoxy-methyl)-5-(1-methylethyl)-6-(phenylmehtyl)-(2,4(1H,3H)pyrimidineone), and (+)-alanolide A and B) and protease inhibitors (for example, saquinavir, ritonavir, indinavir, nelfinavir, amprenavir, lasinavir, DMP-450, BMS-2322623, ABT-378 and AG-1 549);

(xii) chimeric antigen receptors, anticancer vaccines and arginase inhibitors.

The method of treatment or the compound for use in the treatment of inflammation and immunological diseases may involve, in addition to the compound of the invention, additional active agents. The additional active agents may be one or more active agents used to treat the condition being treated by the compound of the invention and additional active agent. The additional active agents may include one or more of the following active agents: —

(i) steroids such as corticosteroids, including glucocorticoids and mineralocorticoids, for example aclometasone, aclometasone dipropionate, aldosterone, amcinonide, beclomethasone, beclomethasone dipropionate, betamethasone, betamethasone dipropionate, betamethasone sodium phosphate, betamethasone valerate, budesonide, clobetasone, clobetasone butyrate, clobetasol propionate, cloprednol, cortisone, cortisone acetate, cortivazol, deoxycortone, desonide, desoximetasone, dexamethasone, dexamethasone sodium phosphate, dexamethasone isonicotinate, difluorocortolone, fluclorolone, flumethasone, flunisolide, fluocinolone, fluocinolone acetonide, fluocinonide, fluocortin butyl, fluorocortisone, fluorocortolone, fluocortolone caproate, fluocortolone pivalate, fluorometholone, fluprednidene, fluprednidene acetate, flurandrenolone, fluticasone, fluticasone propionate, halcinonide, hydrocortisone, hydrocortisone acetate, hydrocortisone butyrate, hydrocortisone aceponate, hydrocortisone buteprate, hydrocortisone valerate, icomethasone, icomethasone enbutate, meprednisone, methylprednisolone, mometasone paramethasone, mometasone furoate monohydrate, prednicarbate, prednisolone, prednisone, tixocortol, tixocortol pivalate, triamcinolone, triamcinolone acetonide, triamcinolone alcohol and their respective pharmaceutically acceptable derivatives. A combination of steroids may be used, for example a combination of two or more steroids mentioned in this paragraph;

(ii) TNF inhibitors for example etanercept; monoclonal antibodies (e.g. infliximab (Remicade), adalimumab (Humira), certolizumab pegol (Cimzia), golimumab (Simponi)); fusion proteins (e.g. etanercept (Enbrel)); and 5-HT$_{2A}$ agonists (e.g. 2,5-dimethoxy-4-iodoamphetamine, TCB-2, lysergic acid diethylamide (LSD), lysergic acid dimethylazetidide);

(iii) anti-inflammatory drugs, for example non-steroidal anti-inflammatory drugs;

(iv) dihydrofolate reductase inhibitors/antifolates, for example methotrexate, trimethoprim, brodimoprim, tetroxoprim, iclaprim, pemetrexed, ralitrexed and pralatrexate; and (v) immunosuppressants for example cyclosporins, tacrolimus, sirolimus pimecrolimus, angiotensin II inhibitors (e.g. Valsartan, Telmisartan, Losartan, Irbesatan, Azilsartan, Olmesartan, Candesartan, Eprosartan) and ACE inhibitors e.g. sulfhydryl-containing agents (e.g. Captopril, Zofenopril), dicarboxylate-containing agents (e.g. Enalapril, Ramipril, Quinapril, Perindopril, Lisinopril, Benazepril, Imidapril, Zofenopril, Trandolapril), phosphate-containing agents (e.g. Fosinopril), casokinins, lactokinins and lactotripeptides.

Such combination treatment may be achieved by way of the simultaneous, sequential or separate dosing of the individual components of the treatment. Such combination products employ the compounds of this invention within a therapeutically effective dosage range described hereinbefore and the other pharmaceutically-active agent within its approved dosage range.

Compounds of the invention may exist in a single crystal form or in a mixture of crystal forms or they may be amorphous. Thus, compounds of the invention intended for pharmaceutical use may be administered as crystalline or amorphous products. They may be obtained, for example, as solid plugs, powders, or films by methods such as precipitation, crystallization, freeze drying, or spray drying, or evaporative drying. Microwave or radio frequency drying may be used for this purpose.

For the above-mentioned compounds of the invention the dosage administered will, of course, vary with the compound employed, the mode of administration, the treatment desired and the disorder indicated. For example, if the compound of the invention is administered orally, then the daily dosage of the compound of the invention may be in the range from 0.01 micrograms per kilogram body weight (μg/kg) to 100 milligrams per kilogram body weight (mg/kg).

A compound of the invention, or pharmaceutically acceptable salt thereof, may be used on their own but will generally be administered in the form of a pharmaceutical composition in which the compounds of the invention, or pharmaceutically acceptable salt thereof, is in association with a pharmaceutically acceptable adjuvant, diluent or carrier. Conventional procedures for the selection and preparation of suitable pharmaceutical formulations are described in, for example, "Pharmaceuticals—The Science of Dosage Form Designs", M. E. Aulton, Churchill Livingstone, 1988.

Depending on the mode of administration of the compounds of the invention, the pharmaceutical composition which is used to administer the compounds of the invention will preferably comprise from 0.05 to 99% w (percent by weight) compounds of the invention, more preferably from 0.05 to 80% w compounds of the invention, still more preferably from 0.10 to 70% w compounds of the invention, and even more preferably from 0.10 to 50% w compounds of the invention, all percentages by weight being based on total composition.

The pharmaceutical compositions may be administered topically (e.g. to the skin) in the form, e.g., of creams, gels, lotions, solutions, suspensions, or systemically, e.g. by oral administration in the form of tablets, capsules, syrups, powders or granules; or by parenteral administration in the form of a sterile solution, suspension or emulsion for injection (including intravenous, subcutaneous, intramuscular, intravascular or infusion); by rectal administration in the form of suppositories; or by inhalation in the form of an aerosol.

For oral administration the compounds of the invention may be admixed with an adjuvant or a carrier, for example, lactose, saccharose, sorbitol, mannitol; a starch, for example, potato starch, corn starch or amylopectin; a cellulose derivative; a binder, for example, gelatine or polyvinylpyrrolidone; and/or a lubricant, for example, magnesium stearate, calcium stearate, polyethylene glycol, a wax, paraffin, and the like, and then compressed into tablets. If coated tablets are required, the cores, prepared as described above, may be coated with a concentrated sugar solution which may contain, for example, gum arabic, gelatine, talcum and titanium dioxide. Alternatively, the tablet may be coated with a suitable polymer dissolved in a readily volatile organic solvent.

For the preparation of soft gelatine capsules, the compounds of the invention may be admixed with, for example, a vegetable oil or polyethylene glycol. Hard gelatine capsules may contain granules of the compound using either the above-mentioned excipients for tablets. Also liquid or semi-solid formulations of the compound of the invention may be filled into hard gelatine capsules. Liquid preparations for oral application may be in the form of syrups or suspensions, for example, solutions containing the compound of the invention, the balance being sugar and a mixture of ethanol, water, glycerol and propylene glycol. Optionally such liquid preparations may contain colouring agents, flavouring agents, sweetening agents (such as saccharine), preservative agents and/or carboxymethylcellulose as a thickening agent or other excipients known to those skilled in art.

For intravenous (parenteral) administration the compounds of the invention may be administered as a sterile aqueous or oily solution.

The size of the dose for therapeutic purposes of compounds of the invention will naturally vary according to the nature and severity of the conditions, the age and sex of the animal or patient and the route of administration, according to well-known principles of medicine.

Dosage levels, dose frequency, and treatment durations of compounds of the invention are expected to differ depending on the formulation and clinical indication, age, and co-morbid medical conditions of the patient. The standard duration of treatment with compounds of the invention is expected to vary between one and seven days for most clinical indications. It may be necessary to extend the duration of treatment beyond seven days in instances of recurrent infections or infections associated with tissues or implanted materials to which there is poor blood supply including bones/joints, respiratory tract, endocardium, and dental tissues.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

EXAMPLES AND SYNTHESIS

Solvents, reagents and starting materials were purchased from commercial vendors and used as received unless otherwise described. All reactions were performed at room temperature unless otherwise stated. Compound identity and purity confirmations were performed by LCMS UV using a Waters Acquity SQ Detector 2 (ACQ-SQD2#LCA081). The diode array detector wavelength was 254 nM and the MS was in positive and negative electrospray mode (m/z: 150-800). A 2 µL aliquot was injected onto a guard column (0.2 µm×2 mm filters) and UPLC column (C18, 50×2.1 mm, <2 µm) in sequence maintained at 40° C. The samples were eluted at a flow rate of 0.6 mL/min with a mobile phase system composed of A (0.1% (v/v) Formic Acid in Water) and B (0.1% (v/v) Formic Acid in Acetonitrile) according to the gradients outlined in Table 1 below. Retention times RT are reported in minutes.

TABLE 1

| Time (min) | % A | % B |
| --- | --- | --- |
| Method 1 | | |
| 0 | 95 | 5 |
| 1.1 | 95 | 5 |
| 6.1 | 5 | 95 |
| 7 | 5 | 95 |
| 7.5 | 95 | 5 |
| 8 | 95 | 5 |
| Method 2 | | |
| 0 | 95 | 5 |
| 0.3 | 95 | 5 |
| 2 | 5 | 95 |
| 2.6 | 95 | 5 |
| 3 | 95 | 5 |

NMR was also used to characterise final compounds. NMR spectra were obtained on a Bruker AVIII 400 Nanobay with 5 mm BBFO probe. Optionally, compound Rf values on silica thin layer chromatography (TLC) plates were measured.

Compound purification was performed by flash column chromatography on silica or by preparative LCMS. LCMS purification was performed using a Waters 3100 Mass detector in positive and negative electrospray mode (m/z: 150-800) with a Waters 2489 UV/Vis detector. Samples were eluted at a flow rate of 20 mL/min on a XBridge™ prep C18 5 µM OBD 19×100 mm column with a mobile phase system composed of A (0.1% (v/v) Formic Acid in Water) and B (0.1% (v/v) Formic Acid in Acetonitrile) according to the gradient outlined in Table 2 below.

TABLE 2

| Time (min) | % A | % B |
| --- | --- | --- |
| 0 | 90 | 10 |
| 1.5 | 90 | 10 |
| 11.7 | 5 | 95 |
| 13.7 | 5 | 95 |
| 14 | 90 | 90 |
| 15 | 90 | 90 |

Chemical names in this document were generated using Elemental Structure to Name Conversion by Dotmatics Scientific Software. Starting materials were purchased from commercial sources or synthesised according to literature procedures.

The compounds of the invention may be synthesised by analogy with the following reaction routes:

General Scheme 1

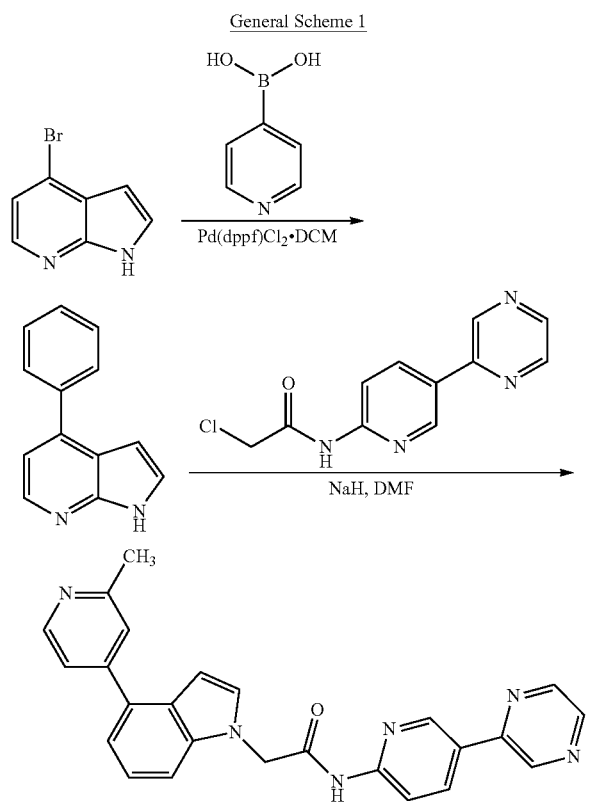

Compounds of the invention could be prepared by analogy with the following route Biaryl Alpha-Chloroacetamide: Synthesis A

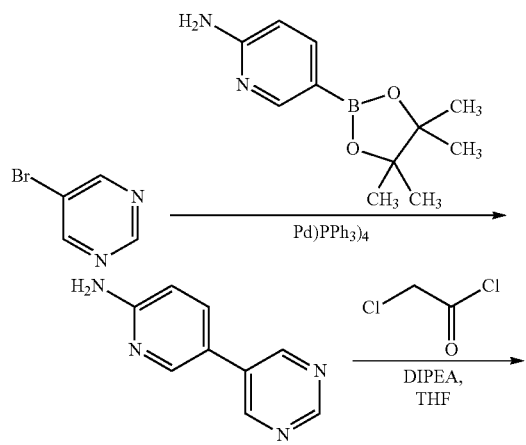

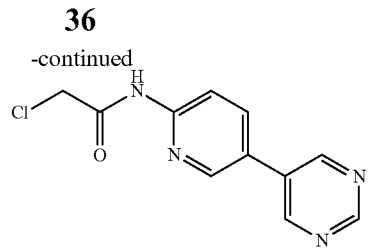

Intermediate 1: 4-(2-methyl-4-pyridyl)-1H-pyrrolo[2,3-b]pyridine

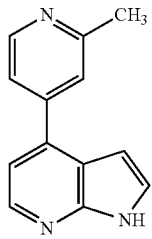 [SMILES: Cc1cc(-c2ccnc3[nH]ccc23)ccn1]

4-Bromo-7-azaindole (247 mg, 1.25 mmol) and sodium carbonate (352 mg, 3.32 mmol) were dissolved in a mixture of ethyl acetate (8 mL) and water (2 mL). Nitrogen was bubbled through the solution for 10 mins, after which (2-methyl-4-pyridinyl)boronic acid (235 mg, 1.72 mmol) and [1,1'-bis(diphenylphosphino)ferrocene]Palladium(II) chloride dichloromethane complex (102.38 mg, 0.13 mmol) were added and the. The reaction was heated in the MW at 100° C. for 2 hrs. LCMS shows incomplete reaction. A further 30 mg of Catalyst and 100 mg of boronic acid were added and the reaction was heated at 100° C. for 30 mins. The reaction was filtered through a celite plug washing with EtOAc. The mixture was diluted with sat NH$_4$Cl solution, the layers separated and the aqueous phase extracted twice with EtOAc. The combined organic extracts were dried over Na$_2$SO$_4$ and reduced in vacuo. The crude material was loaded onto a 10 g SCX cartridge and eluted with MeOH and then 1M NH$_3$ in MeOH. The ammonia layer was reduced in vacuo to afford 4-(2-methyl-4-pyridyl)-1H-pyrrolo[2,3-b]pyridine (280 mg, 1.34 mmol, 106.74% yield) as a brown solid.

MS Method 2: RT: 0.79 min, ES$^+$ m/z 210.1 [M+H]$^+$ $^1$H NMR (400 MHz, CDCl$_3$) δ/ppm: 10.39-10.50 (bs, 1H), 8.96-8.71 (1H, d, J=5.1 Hz, 1H), 8.44-8.47 (d, J=4.9 Hz, 1H), 7.43-7.55 (m, 3H), 7.21-7.25 (1H, d, J=4.9 Hz, 1H), 6.71-6.74 (d, J=3.2 Hz, 1H), 2.79 (s, 3H)

Biaryl Alpha-Chloroacetamide: Synthesis A—Step 1

Intermediate 2: 5-pyrazin-2-ylpyridin-2-amine

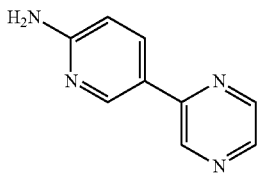 [SMILES: Nc1ccc(-c2cnccn2)cn1]

A microwave vial with stirrer bar was charged with 2-aminopyridine-5-boronic acid pinacol ester (0.95 g, 4.3 mmol) iodopyrazine (777 mg, 3.77 mmol), sodium carbonate (1.20 g, 11.32 mmol) Toluene (5 mL) Water (5 mL) Ethanol (5 mL) and degassed for 10 mins.

Tetrakis(triphenylphosphine)palladium(0) (436 mg, 0.38 mmol) was then added and the vial sealed then irradiated at 100° C. for 1 hr. Analysis showed completion so the reaction mixture was concentrated to dryness, then the residue was suspended in DCM and 1M aqueous HCl was then added. The phases were separated and the aqueous phase was basified with 10% aqueous NaOH until pH-12, The aqueous layer was re-extracted with EtOAc several times, dried over sodium sulphate, filtered and concentrated. The resulting solid was triturated with diethyl ether and then filtered giving 5-pyrazin-2-ylpyridin-2-amine (355 mg, 1.65 mmol, 43.702% yield) as a pink powder.

MS Method 2: RT 0.45 min, ES+ m/z 172.9 [M+H]+

$^1$H NMR (400 MHz, DMSO) δ/ppm: 9.08 (s, 1H), 8.71-8.73 (d, J=1.9 Hz, 1H), 8.58-8.6 (m, 1H), 8.45-8.47 (d, J=2.5 Hz, 1H), 8.10-8.14 (dd, J=8.7, 2.5 Hz, 1H), 6.54-6.57 (d, J=8.7 Hz, 1H), 6.41-6.47 (bs, 2H)

Biaryl Alpha-Chloroacetamide: Synthesis
A—Step 2
Intermediate 3:
2-chloro-N-(5-pyrazin-2-yl-2-pyridyl)acetamide

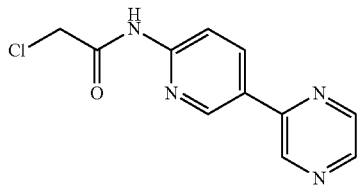 [SMILES: O=C(CCl)Nc1ccc(-c2cnccn2)cn1]

To a pink suspension of 5-pyrazin-2-ylpyridin-2-amine (355 mg, 2.06 mmol), THF (1.5 mL) and N,N-diisopropylethylamine (0.72 mL, 4.12 mmol) was added drop-wise chloroacetyl chloride (0.16 mL, 2.06 mmol) at room temperature. The suspension turned black and a large exotherm was given off. Analysis of the reaction after 30 mins showed that it was complete. The reaction was diluted with methanol and then concentrated. The resulting residue was purified by flash column chromatography (12 g SiO$_2$, 30-100% EtOAc in heptane, then 0-20% MeOH in EtOAc) affording an off white/brown solid 2-chloro-N-(5-pyrazin-2-yl-2-pyridyl)acetamide (194 mg, 0.78 mmol, 37.84% yield).

MS Method 2: RT 1.10 min, ES+ m/z 249 [M+H]+

$^1$H NMR (400 MHz, CDCl$_3$) δ/ppm: 8.96-8.99 (d, J=1.5 Hz, 1H), 8.91-8.93 (m, 1H), 8.85-8.89 (bs, 1H), 8.58-8.61 (m, 1H), 8.48-8.50 (d, J=2.5 Hz, 1H), 8.27-8.35 (m, 2H), 4.17 (s, 2H)

Example 1: 2-[4-(2-methyl-4-pyridyl)pyrrolo[2,3-b]pyridin-1-yl]-N-(5-pyrazin-2-yl-2-pyridyl)acetamide

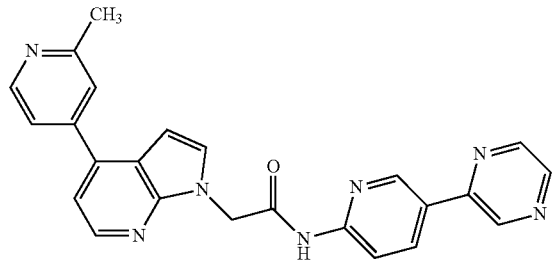 [SMILES: Cc1cc(-c2ccnc3c2ccn3CC(=O)Nc2ccc(-c3cnccn3)cn2)ccn1]

To a solution of 4-(2-methyl-4-pyridyl)-1H-pyrrolo[2,3-b]pyridine (230 mg, 1.1 mmol) in DMF (6 mL) at 0° C. was added sodium hydride, (60% dispersed in mineral oil) (61 mg, 1.54 mmol). The reaction was stirred at 0° C. for 1 hour, after which 2-chloro-N-(5-pyrazin-2-yl-2-pyridyl)acetamide (475 mg, 1.91 mmol) was added in one portion. The reaction was warmed to room temperature and left to stir overnight. LCMS indicates incomplete reaction. The reaction was again cooled to 0° C., and NaH (50 mg) was added. After stirring for 1 hour, chloroacetamide (75 mg) was added and the reaction was warmed to room temperature and stirred over the weekend. The reaction was diluted with water and the aqueous phase extracted three times with EtOAc. The combined organic extracts were dried over Na$_2$SO$_4$ and reduced in vacuo. The crude material purified by flash column chromatography (40 g SiO$_2$ 0 to 100% EtOAc in heptane, followed by 0 to 10% MeOH in EtOAc), however the material was still not The semi-pure material was dry loaded onto silica and purified again by flash column chromatography (12 g SiO$_2$, 50% to 100% EtOAc in heptane, followed by 0 to 5% MeOH in EtOAc) to afford 2-[4-(2-methyl-4-pyridyl)pyrrolo[2,3-b]pyridin-1-yl]-N-(5-pyrazin-2-yl-2-pyridyl)acetamide (58 mg, 0.14 mmol, 12.52% yield) as a tan solid.

MS Method 1: RT: 2.43 min, ES+ m/z 422.1 [M+H]+

$^1$H NMR (400 MHz, DMSO) δ/ppm: 12.27 (s, 1H), 9.31-9.33 (d, J=1.5 Hz, 1H), 9.14-9.16 (d, J=1.9 Hz, 1H), 8.72-8.74 (m, 1H), 8.61-8.65 (m, 2H), 8.51-8.55 (dd, J=8.7, 2.6 Hz, 1H), 8.35-8.37 (d, J=4.9 Hz, 1H), 8.12-8.17 (d, J=8.7 Hz, 1H), 7.73-7.76 (d, J=3.7 Hz, 1H), 7.66 (s, 1H), 7.58-7.61 (d, J=5.0 Hz, 1H), 7.34-7.37 (d, J=5.0 Hz, 1H), 6.75-6.77 (d, J=3.5 Hz, 1H), 5.35 (s, 2H), 2.61 (s, 3H).

Example 2

The following compound was prepared by analogy with General Scheme 1 substituting 4-Bromo-7-azaindole with the appropriate 5,6-fused bromo-heteroaryl.

| STRUCTURE | STRUCTURE NAME | LCMS RT (min) | m/z MIM |
|---|---|---|---|
| 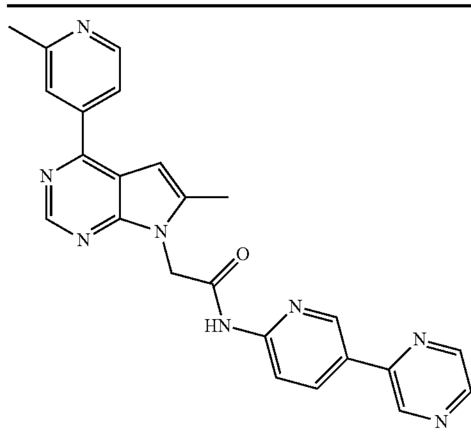 | 2-[6-methyl-4-(2-methyl-4-pyridyl)pyrrolo[2,3-d]pyrimidin-7-yl]-N-(5-pyrazin-2-yl-2-pyridyl)acetamide | 2.41 (Method 1) | 436.47 |

General Scheme 2

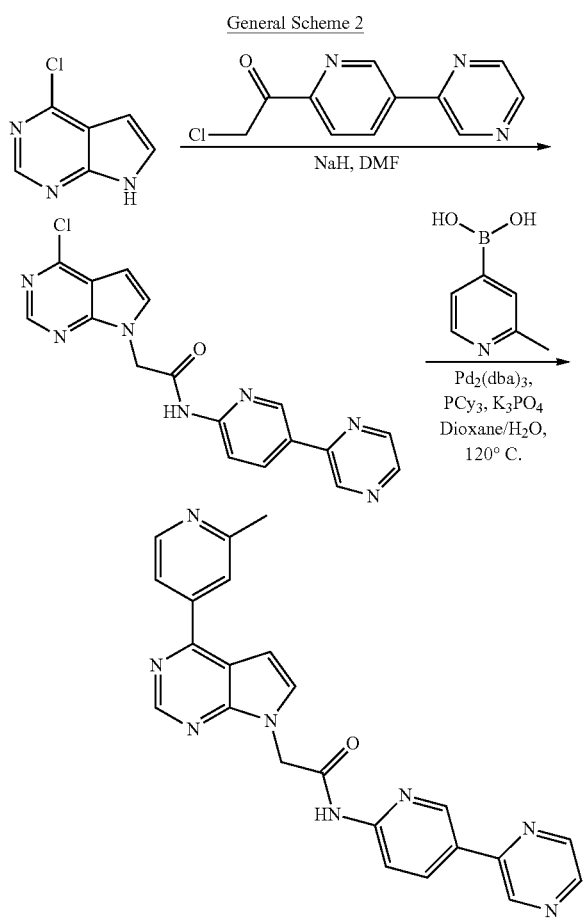

Further compounds of the invention could be prepared by analogy with the following route Intermediate 4: 2-(4-chloropyrrolo[2,3-d]pyrimidin-7-yl)-N-(5-pyrazin-2-yl-2-pyridyl)acetamide

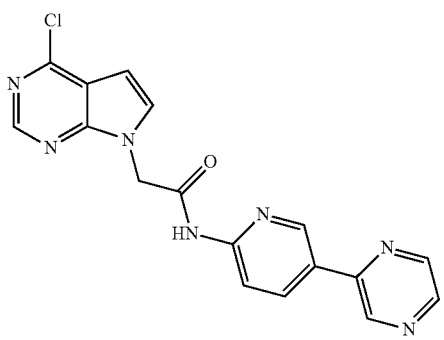 [SMILES: O=C(Cn1ccc2c(Cl)ncnc21)Nc1ccc(-c2cnccn2)cn1]

6-Chloro-7-deazapurine (139 mg, 0.91 mmol) was dissolved in DMF (2.5 mL) and the solution was cooled to 0° C. NaH (60% dispersed in mineral oil) (54.3 mg, 1.36 mmol) was added and the reaction was stirred at 0° C. for 45 mins. The reaction was warmed to room temperature and left to stir for 15 mins, after which the reaction was again cooled to 0° C. and 2-chloro-N-(5-pyrazin-2-yl-2-pyridyl)acetamide (337 mg, 1.36 mmol) was added. The reaction was warmed to room temperature and left to stir for 16 hours. LCMS showed completion of reaction. The reaction was quenched by the addition of water and extracted three times with EtOAc. Combined organic extracts were dried over $Na_2SO_4$ and reduced in vacuo. The product was deposited on silica and purified by flash column chromatography (12 g column, 0 to 100% EtOAc in Heptane then 0 to 10% MeOH in EtOAc) to furnish the product 2-(4-chloropyrrolo[2,3-d]pyrimidin-7-yl)-N-(5-pyrazin-2-yl-2-pyridyl)acetamide (240 mg, 0.60 mmol, 66% yield) as a tan solid.

MS Method 2: RT 3.11 min, $ES^+$ m/z 366 $[M+H]^+$ $^1$H NMR (400 MHz, $d^6$-DMSO) δ/ppm: 11.3 (s, 1H), 9.32 (d, 1H, J=1.6 Hz), 9.14 (dd, 1H, J=2.5, 0.8 Hz), 8.71 (dd, 1H, J=2.5, 1.6 Hz), 8.64 (dd, 1H, J=2.5 Hz), 8.52 (dd, 1H, J=8.8, 2.5 Hz), 8.11 (d, 1H, J=8.8 Hz), 7.96 (s, 1H), 7.81 (d, 1H, J=3.6 Hz), 6.71 (d, 1H, J=3.6 Hz), 5.34 (s, 2H).

Example 3: 2-[4-(2-methyl-4-pyridyl)pyrrolo[2,3-d]pyrimidin-7-yl]-N-(5-pyrazin-2-yl-2-pyridyl)acetamide

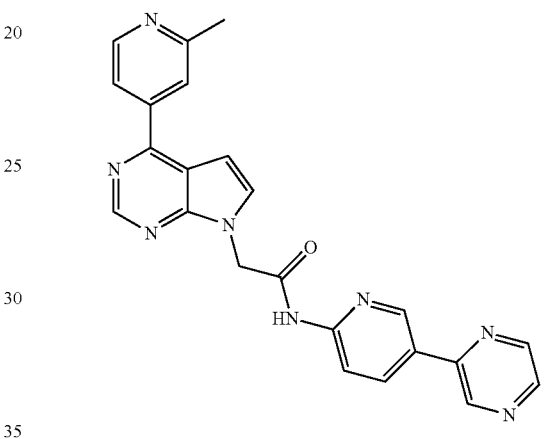

In a 2.0-5.0 mL microwave vial 2-(4-chloropyrrolo[2,3-d]pyrimidin-7-yl)-N-(5-pyrazin-2-yl-2-pyridyl)acetamide (110 mg, 0.27 mmol) and sodium carbonate (58 mg, 0.55 mmol) were suspended in 1,4-dioxane (2.5 mL) and water (0.5 mL). Nitrogen was bubbled through the solution for 10 mins, after which (2-methyl-4-pyridinyl)boronic acid (49 mg, 0.36 mmol) and tetrakis(triphenylphosphine)palladium (0) (32 mg, 0.02 mmol) were added. The vial was capped and the reaction was heated by microwave irradiation at 120° C. for 1 hour. The reaction was observed to be complete by LCMS. The reaction was diluted with sat. $NaHCO_3$ and extracted three times with EtOAc. Combined organic extracts were dried over $Na_2SO_4$ and reduced in vacuo. The product was dry loaded onto silica and purified by flash column chromatography to afford 2-[4-(2-methyl-4-pyridyl)pyrrolo[2,3-d]pyrimidin-7-yl]-N-(5-pyrazin-2-yl-2-pyridyl)acetamide (29 mg, 0.07 mmol, 25% yield) as a grey solid.

MS Method 1: RT 2.30 min, $ES^+$ m/z 423 $[M+H]^+$ $^1$H NMR (400 MHz, $d^6$-DMSO) δ/ppm: 11.3 (s, 1H), 9.32 (d, 1H, J=1.5 Hz), 9.15 (dd, 1H, J=2.4, 0.6 Hz), 8.93 (s, 1H), 8.73 (dd, 1H, J=2.5, 1.5 Hz), 8.69 (d, 1H, J=5.2 Hz), 8.64 (d, 1H, J=2.5 Hz), 8.53 (dd, 1H, J=8.8, 2.5 Hz), 8.13 (d, 1H, J=8.8 Hz), 8.00 (bs, 1H), 7.94 (dd, 1H, J=5.2, 1.5 Hz), 7.85 (d, 1H, J=3.8 Hz), 7.08 (s, 1H, J=3.8 Hz), 5.38 (s, 2H), 2.64 (s, 3H).

Example 4

The following compounds were prepared by analogy with General Scheme 2 substituting 6-Chloro-7-deazapurine with the appropriate 5,6-fused chloro heteroaryl and (2-methyl-4-pyridinyl)boronic acid with the appropriate heteroaryl boronic acid.

| Structure | STRUCTURE NAME | LCMS RT (min) | m/z MIM |
|---|---|---|---|
| 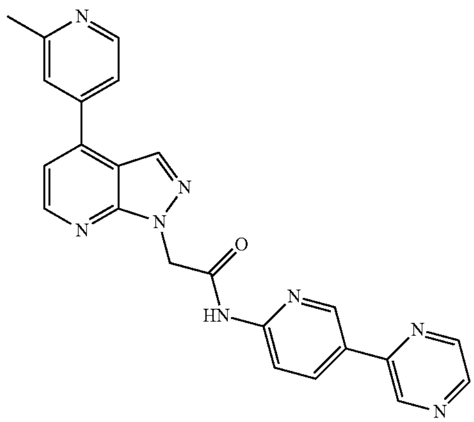 [SMILES: Cc1cc(-c2ccnc3c2cnn3CC(=O)Nc2ccc(-c3cnccn3)cn2)ccn1] | 2-[4-(2-methyl-4-pyridyl)pyrazolo[3,4-b]pyridin-1-yl]-N-(5-pyrazin-2-yl-2-pyridyl)acetamide | 2.31 (Method 1) | 422.44 |
| 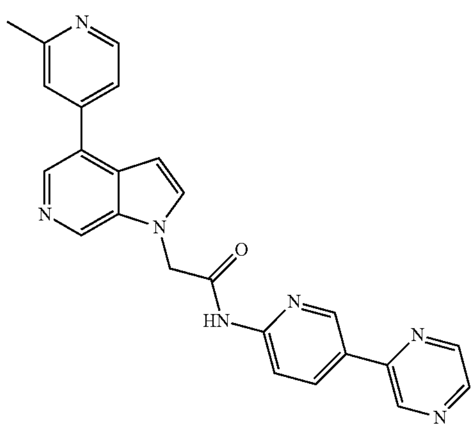 [SMILES: Cc1cc(-c2cncc3c2ccn3CC(=O)Nc2ccc(-c3cnccn3)cn2)ccn1] | 2-[4-(2-methyl-4-pyridyl)pyrrolo[2,3-c]pyridin-1-yl]-N-(5-pyrazin-2-yl-2-pyridyl)acetamide | 1.92 (Method 1) | 421.45 |
| 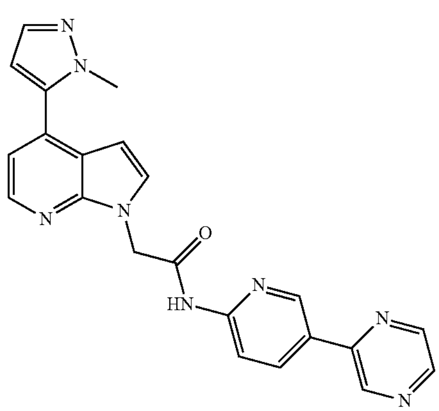 [SMILES: Cn1nccc1-c1ccnc2c1ccn2CC(=O)Nc1ccc(-c2cnccn2)cn1] | 2-[4-(2-methylpyrazol-3-yl)pyrazolo[3,4-b]pyridin-1-yl]-N-(5-pyrazin-2-yl-2-pyridyl)acetamide | 2.85 (Method 1) | 411.42 |

| Structure | STRUCTURE NAME | LCMS RT (min) | m/z MIM |
|---|---|---|---|
| 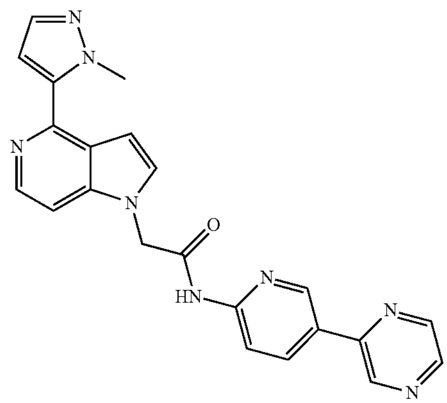 [SMILES: Cn1nccc1-c1nccc2c1ccn2CC(=O)Nc1ccc(-c2cnccn2)cn1] | 2-[4-(2-methylpyrazol-3-yl)pyrrolo[3,2-c]pyridin-1-yl]-N-(5-pyrazin-2-yl-2-pyridyl)acetamide | 0.99 (Method 2) | 410.43 |
| 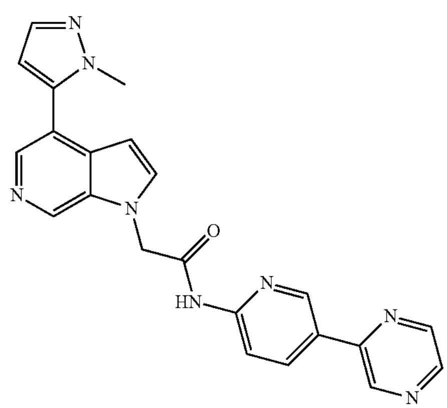 [SMILES: Cn1nccc1-c1cncc2c1ccn2CC(=O)Nc1ccc(-c2cnccn2)cn1] | 2-[4-(2-methylpyrazol-3-yl)pyrrolo[2,3-c]pyridin-1-yl]-N-(5-pyrazin-2-yl-2-pyridyl)acetamide | 2.32 (Method 1) | 410.43 |
| 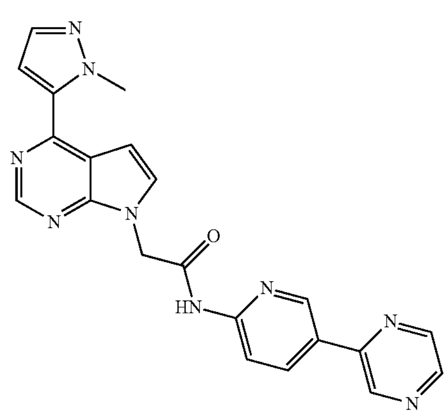 [SMILES: Cn1nccc1-c1ncnc2c1ccn2CC(=O)Nc1ccc(-c2cnccn2)cn1] | 2-[4-(2-methylpyrazol-3-yl)pyrrolo[2,3-d]pyrimidin-7-yl]-N-(5-pyrazin-2-yl-2-pyridyl)acetamide | 2.88 (Method 1) | 411.42 |

| Structure | STRUCTURE NAME | LCMS RT (min) | m/z MIM |
|---|---|---|---|
| 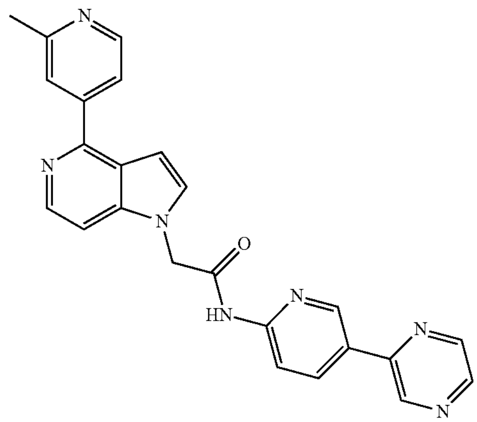 [SMILES: Cc1cc(-c2nccc3c2ccn3CC(=O)Nc2ccc(-c3cnccn3)cn2)ccn1] | 2-[4-(2-methyl-4-pyridyl)pyrrolo[3,2-c]pyridin-1-yl]-N-(5-pyrazin-2-yl-2-pyridyl)acetamide | 2.21 (Method 1) | 421.45 |
| 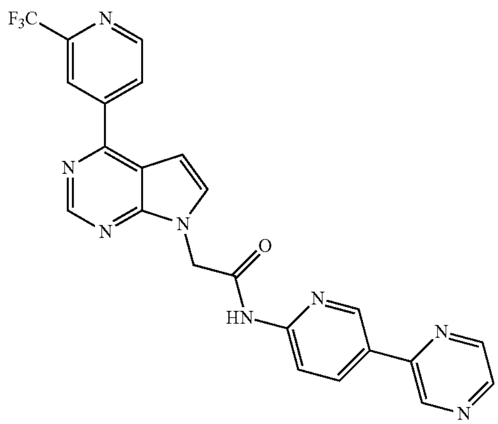 [SMILES: O=C(Cn1ccc2c(-c3ccnc(C(F)(F)F)c3)ncnc21)Nc1ccc(-c2cnccn2)cn1] | N-(5-pyrazin-2-yl-2-pyridyl)-2-[4-[2-(trifluoromethyl)-4-pyridyl]pyrrolo[2,3-d]pyrimidin-7-yl]acetamide | 3.56 (Method 1) | 476.41 |
| 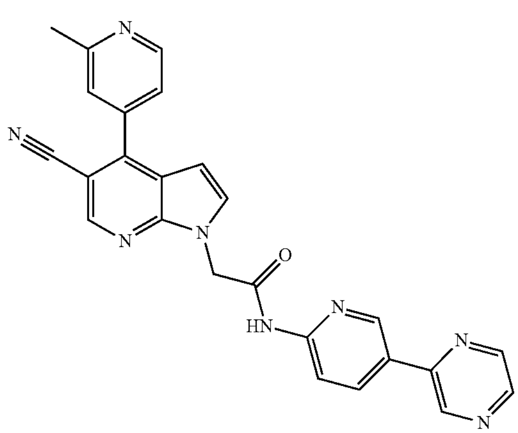 [SMILES: Cc1cc(-c2c(C#N)cnc3c2ccn3CC(=O)Nc2ccc(-c3cnccn3)cn2)ccn1] | 2-[5-cyano-4-(2-methyl-4-pyridyl)pyrrolo[2,3-b]pyridin-1-yl]-N-(5-pyrazin-2-yl-2-pyridyl)acetamide | 2.60 (Method 1) | 446.46 |

| Structure | STRUCTURE NAME | LCMS RT (min) | m/z MIM |
|---|---|---|---|
| 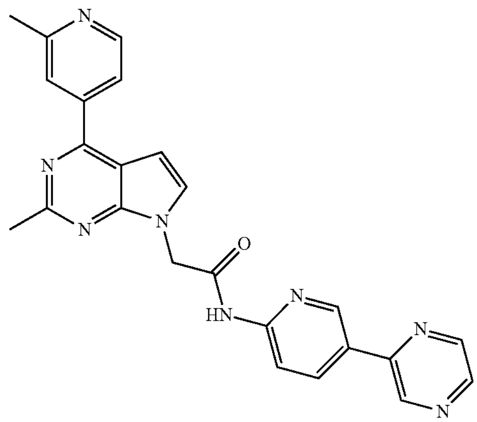 [SMILES: Cc1cc(-c2nc(C)nc3c2ccn3CC(=O)Nc2ccc(-c3cnccn3)cn2)ccn1] | 2-[2-methyl-4-(2-methyl-4-pyridyl)pyrrolo[2,3-d]pyrimidin-7-yl]-N-(5-pyrazin-2-yl-2-pyridyl)acetamide | 2.41 (Method 1) | 436.47 |
| 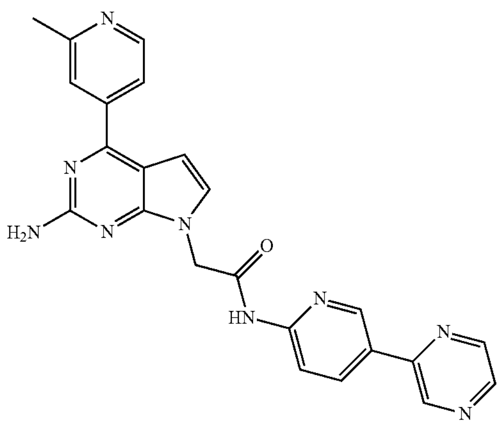 [SMILES: Cc1cc(-c2nc(N)nc3c2ccn3CC(=O)Nc2ccc(-c3cnccn3)cn2)ccn1] | 2-[2-amino-4-(2-methyl-4-pyridyl)pyrrolo[2,3-d]pyrimidin-7-yl]-N-(5-pyrazin-2-yl-2-pyridyl)acetamide | 2.24 (Method 1) | 437.46 |
| 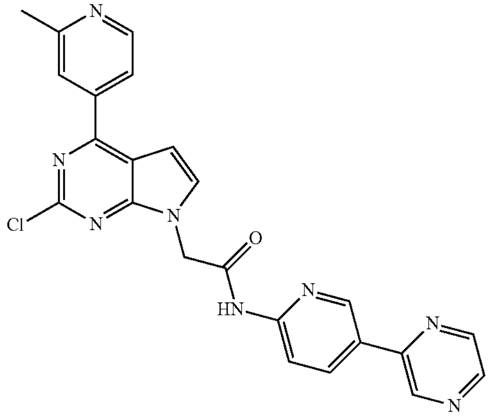 [SMILES: Cc1cc(-c2nc(Cl)nc3c2ccn3CC(=O)Nc2ccc(-c3cnccn3)cn2)ccn1] | 2-[2-chloro-4-(2-methyl-4-pyridyl)pyrrolo[2,3-d]pyrimidin-7-yl]-N-(5-pyrazin-2-yl-2-pyridyl)acetamide | 1.20 (Method 2) | 456.89 |

| Structure | STRUCTURE NAME | LCMS RT (min) | m/z MIM |
|---|---|---|---|
| 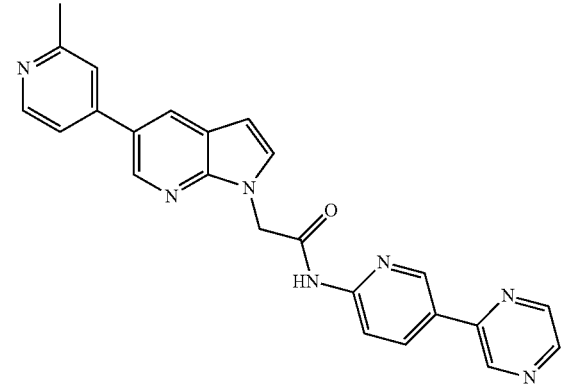 [SMILES: Cc1cc(-c2cnc3c(ccn3CC(=O)Nc3ccc(-c4cnccn4)cn3)c2)ccn1] | 2-[5-(2-methyl-4-pyridyl)pyrrolo[2,3-b]pyridin-1-yl]-N-(5-pyrazin-2-yl-2-pyridyl)acetamide | 2.41 (Method 1) | 421.45 |
| 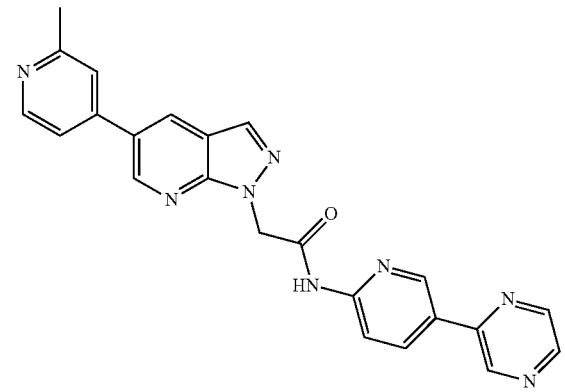 [SMILES: Cc1cc(-c2cnc3c(cnn3CC(=O)Nc3ccc(-c4cnccn4)cn3)c2)ccn1] | 2-[5-(2-methyl-4-pyridyl)pyrazolo[3,4-b]pyridin-1-yl]-N-(5-pyrazin-2-yl-2-pyridyl)acetamide | 2.25 (Method 1) | 422.44 |
| 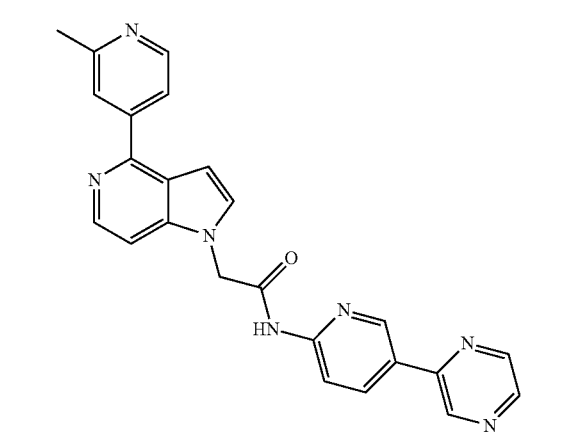 [SMILES: Cc1cc(-c2nccc3c2ccn3CC(=O)Nc2ccc(-c3cnccn3)cn2)ccn1] | 2-[4-(2-methyl-4-pyridyl)imidazo[4,5-c]pyridin-1-yl]-N-(5-pyrazin-2-yl-2-pyridyl)acetamide | 2.24 (Method 1) | 422.44 |

General Scheme 3

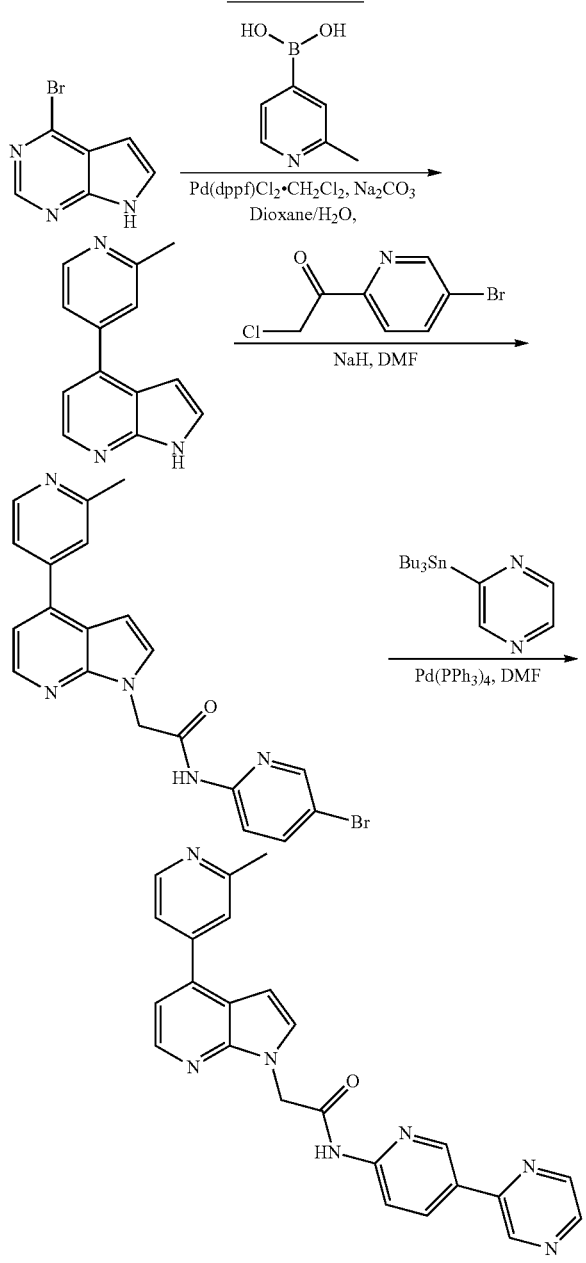

Further compounds of the invention could be prepared by analogy with the following route Intermediate 5:
N-(6-bromo-3-pyridyl)-2-chloro-acetamide

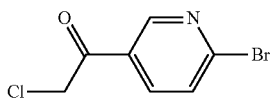 [SMILES: O=C(CCl)c1ccc(Br)nc1]

5-amino-2-bromopyridine (1.44 g, 8.32 mmol) and DIPEA (2.23 mL, 12.5 mmol) were dissolved in DMF (40 mL). Chloroacetyl chloride (0.7 mL, 8.74 mmol) was added dropwise and the reaction was left to stir at room temperature for 16 hours. LCMS showed that the reaction had completed. The reaction was quenched by the addition of water and extracted three times with EtOAc. Combined organic extracts were dried over Na2SO4 and reduced in vacuo. The crude product was deposited onto silica and purified by flash column chromatography (80 g column, 0 to 100% EtOAc in Heptane) to furnish N-(6-bromo-3-pyridyl)-2-chloro-acetamide (1.52 g, 6.09 mmol, 73% yield) as a yellow solid.

MS Method 2: RT 1.25 min, ES$^+$ m/z 250 [M+H]$^+$ $^1$H NMR (400 MHz, CDCl$_3$) δ/ppm: 8.45 (d, 1H, J=2.8 Hz), 8.40 (bs, 1H), 8.05 (dd, 1H, J=8.6, 2.8 Hz), 7.48 (d, 1H, J=8.6 Hz), 4.22 (s, 2H).

Intermediate 6: N-(6-bromo-3-pyridyl)-2-[4-(2-methyl-4-pyridyl)pyrrolo[2,3-b]pyridine-1-yl]acetamide 4-(2-methyl-4-pyridyl)-1H-pyrrolo[2,3-b]pyridine (163 mg, 0.78 mmol) was dissolved in DMF (5 mL) and cooled to 0° C. NaH (60% dispersed in mineral oil) (38 mg, 0.93 mmol) was added and the reaction was stirred at 0° C. for 45 mins. The reaction was warmed to room temperature and stirred for 15 mins, after which the reaction was cooled to 0° C. and N-(6-bromo-3-pyridyl)-2-chloro-acetamide (243 mg, 0.97 mmol) was added. The reaction was warmed to room temperature and left to stir for 16 hours. LCMS indicates a small amount of starting material remaining but mainly formation of desired product. The reaction was quenched by the addition of water and extracted three times with EtOAc. Combined organic extracts were reduced in vacuo. The crude product was deposited onto silica and the purified by flash column chromatography (12 g column, 0 to 100% EtOAc in Heptane then 0 to 10% MeOH in EtOAc) to afford N-(6-bromo-3-pyridyl)-2-[4-(2-methyl-4-pyridyl)pyrrolo[2,3-b]pyridine-1-yl]acetamide (230 mg, 0.54 mmol, 70% yield).

MS Method 2: RT 1.13 min, ES$^+$ m/z 423 [M+H]$^+$ $^1$H NMR (400 MHz, d$^6$-DMSO) δ/ppm: 10.83 (s, 1H), 8.63-8.61 (m, 2H), 8.35 (d, 1H, J=5.0 Hz), 7.98 (dd, 1H, J=8.7, 2.8 Hz), 7.72 (d, 1H, J=3.6 Hz), 7.52 (bs, 1H), 7.62 (dd, 1H, J=8.7, 0.4 Hz), 7.58 (dd, 1H, J=5.0, 1.5 Hz), 7.35 (d, 1H, J=4.9 Hz), 6.75 (d, 1H, J=3.6 Hz), 5.26 (s, 2H), 2.60 (s, 3H).

Example 5: 2-[4-(2-methyl-4-pyridyl)pyrrolo[2,3-b]pyridin-1-yl]-N-(6-pyrazin-2-yl-3-pyridyl)acetamide

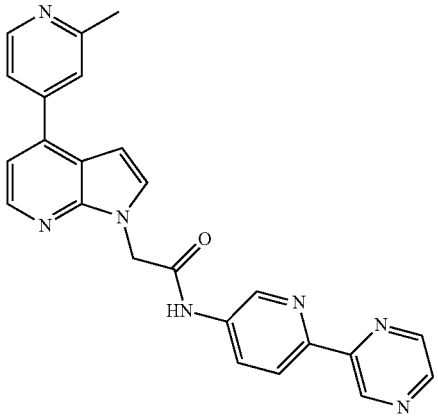 [SMILES: Cc1cc(-c2ccnc3c2ccn3CC(=O)Nc2ccc(-c3cnccn3)nc2)ccn1]

In a 2.0-5.0 mL microwave vial N-(6-bromo-3-pyridyl)-2-[4-(2-methyl-4-pyridyl)pyrrolo[2,3-b]pyridine-1-yl]acetamide (75 mg, 0.18 mmol) and (tributylstannyl)pyrazine (78 mg, 0.21 mmol) were dissolved in DMF (2.5 mL). Nitrogen was bubbled though the solution for 10 mins, after which tetrakis(triphenylphosphine)palladium (0) (21 mg, 0.02 mmol) was added, the vial was capped and the reaction mixture was heated by microwave irradiation at 120° C. for 7 hours. LCMS indicated formation of desired product with a small amount of starting material remaining. The reaction was diluted with sat. NaHCO$_3$ solution and extracted three times with EtOAc. Combined organic extracts were reduced in vacuo. The crude product was deposited onto silica and purified by flash column chromatography (12 g column, 0 to 100% EtOAc in Heptane then 0 to 10% MeOH in EtOAc) to give 2-[4-(2-methyl-4-pyridyl)pyrrolo[2,3-b]pyridin-1-yl]-N-(6-pyrazin-2-yl-3-pyridyl)acetamide (7.0 mg, 0.02 mmol, 10% yield) as a white solid.

MS Method 1: RT 2.36 min, ES$^+$ m/z 422 [M+H]$^+$ $^1$H NMR (400 MHz, d$^6$-DMSO) δ/ppm: 10.94 (s, 1H), 9.49 (d, 1H, J=1.4 Hz), 8.93 (d, 1H, J=2.4 Hz), 8.71 (dd, 1H, J=2.4, 1.5 Hz), 8.67 (d, 1H, J=2.5 Hz), 8.63 (d, 1H, J=5.1 Hz), 8.37 (d, 1H, J=5.1 Hz), 8.34 (d, 1H, J=8.6 Hz), 8.25 (dd, 1H, J=8.6, 2.5 Hz), 7.76 (d, 1H, J=3.7 Hz), 7.66 (bs, 1H), 7.59 (d, 1H, J=5.2 Hz), 7.36 (d, 1H, J=4.9 Hz), 6.77 (d, 1H, J=3.7 Hz), 5.32 (s, 2H), 2.60 (s, 3H).

Example 6

The following compounds were prepared by analogy with General Scheme 3 using the appropriate 5,6-fused chloro heteroaryl and heteroaryl boronic acid.

| Structure | STRUCTURE NAME | LCMS RT (min) | m/z MIM |
|---|---|---|---|
| 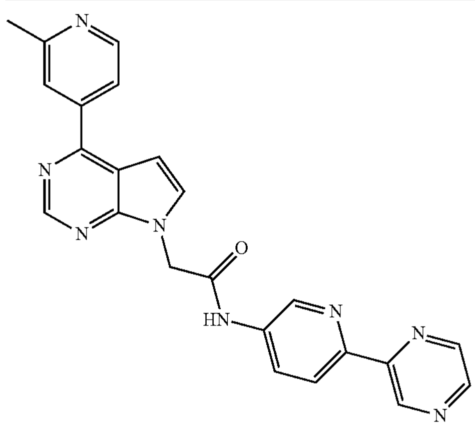 [SMILES: Cc1cc(-c2ncnc3c2ccn3CC(=O)Nc2ccc(-c3cnccn3)nc2)ccn1] | 2-[4-(2-methyl-4-pyridyl)pyrrolo[2,3-d]pyrimidin-7-yl]-N-(6-pyrazin-2-yl-3-pyridyl)acetamide | 2.28 (Method 1) | 422.44 |
| 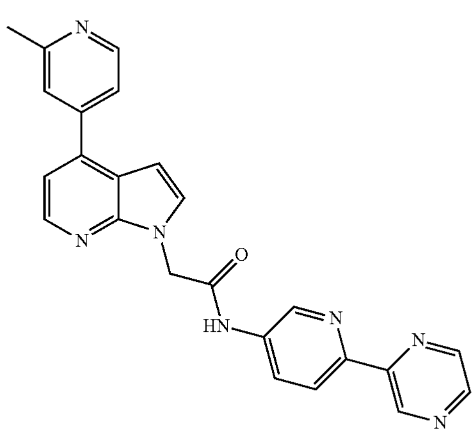 [SMILES: Cc1cc(-c2ccnc3c2ccn3CC(=O)Nc2ccc(-c3cnccn3)nc2)ccn1] | 2-[4-(2-methyl-4-pyridyl)pyrazolo[3,4-b]pyridin-1-yl]-N-(6-pyrazin-2-yl-3-pyridyl)acetamide | 2.28 (Method 1) | 422.44 |

| Structure | STRUCTURE NAME | LCMS RT (min) | m/z MIM |
|---|---|---|---|
| 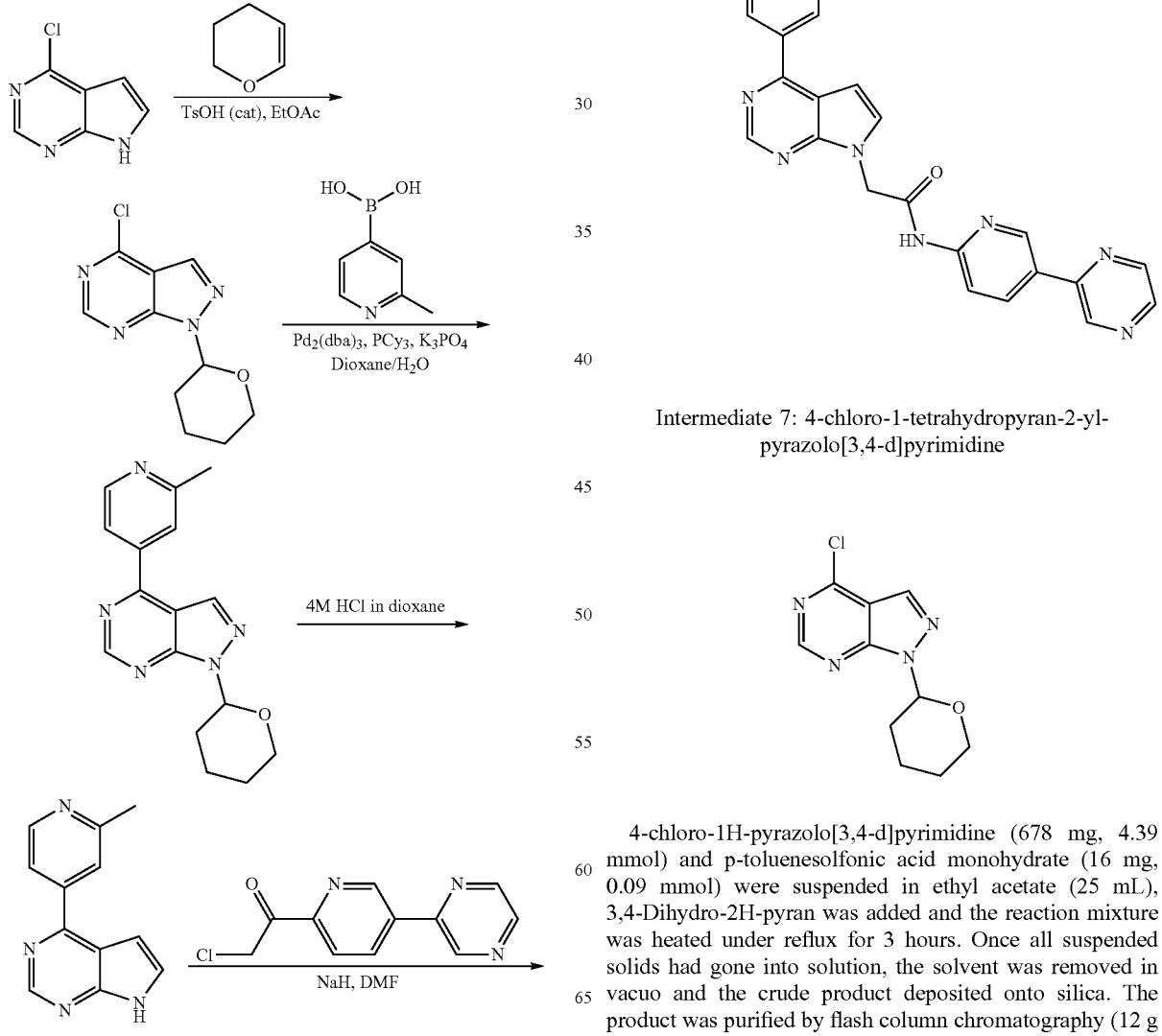 | 2-[4-(2-methyl-4-pyridyl)pyrazolo[3,4-d]pyrimidin-1-yl]-N-(6-pyrazin-2-yl-3-pyridyl)acetamide | 2.34 (Method 1) | 423.43 |

Intermediate 7: 4-chloro-1-tetrahydropyran-2-yl-pyrazolo[3,4-d]pyrimidine 4-chloro-1H-pyrazolo[3,4-d]pyrimidine (678 mg, 4.39 mmol) and p-toluenesolfonic acid monohydrate (16 mg, 0.09 mmol) were suspended in ethyl acetate (25 mL), 3,4-Dihydro-2H-pyran was added and the reaction mixture was heated under reflux for 3 hours. Once all suspended solids had gone into solution, the solvent was removed in vacuo and the crude product deposited onto silica. The product was purified by flash column chromatography (12 g column, 0 to 100% EtOAc in Heptane) to furnish 4-chloro- 1-tetrahydropyran-2-yl-pyrazolo[3,4-d]pyrimidine (840 mg, 3.52 mmol, 80% yield) as a pink solid.

¹H NMR (400 MHz, CDCl₃) δ/ppm: 8.80 (s, 1H), 8.22 (s, 1H), 6.05 (dd, 1H, J=10.4, 2.5 Hz), 4.15-4.10 (m, 1H), 3.85-3.77 (m, 1H), 2.68-2.57 (m, 1H), 2.21-2.12 (m, 1H), 2.03-1.95 (m, 1H), 1.95-1.77 (m, 2H), 1.69-1.63 (m, 1H).

Intermediate 8: 4-(2-methyl-4-pyridyl)-1-tetrahydropyran-2-yl-pyrazolo[3,4-d]pyrimidine

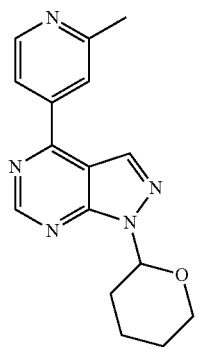 [SMILES: Cc1cc(-c2ncnc3c2cnn3C2CCCCO2)ccn1]

In a 10-20 mL microwave vial 4-chloro-1-tetrahydropyran-2-yl-pyrazolo[3,4-d]pyrimidine (153 mg, 0.64 mmol) and sodium carbonate (135 mg, 1.28 mmol) were suspended in 1,4-dioxane (4 mL) and water (1 mL). Nitrogen was bubbled through the solution for 5 mins, after which (2-methyl-4-pyridinyl)boronic acid (105 mg, 0.77 mmol) and [1,1'-bis(diphenylphosphino)ferrocene]dichloropalladium (11). CH₂Cl₂ (52 mg, 0.06 mmol) were added the vial was capped and the reaction was heated under microwave irradiation at 120° C. for 1 hour. LCMS showed that the reaction had completed. The reaction was quenched by the addition of sat. NaHCO₃ and extracted three times with EtOAc. Combined organic extracts were reduced in vacuo and deposited onto silica. The crude product was purified by flash column chromatography (12 g column, 0 to 100% EtOAc in Heptane then 0 to 5% MeOH in EtOAc) to furnish 4-(2-methyl-4-pyridyl)-1-tetrahydropyran-2-yl-pyrazolo[3,4-d]pyrimidine (130 mg, 0.44 mmol, 69% yield) as an orange oil.

MS Method 2: RT 1.16 min, ES⁺ m/z 296 [M+H]⁺

¹H NMR (400 MHz, CDCl₃) δ/ppm: 9.16 (s, 1H), 8.78 (dd, 1H, J=5.2, 0.6 Hz), 8.43 (s, 1H), 7.92 (bs, 1H), 7.81 (ddd, 1H, J=5.2, 1.7, 0.6 Hz), 6.17 (dd, 1H, J=10.4, 2.6 Hz), 4.20-4.14 (m, 1H), 3.90-3.82 (m, 1H), 2.74 (s, 3H), 2.72-2.63 (m, 1H), 2.24-2.15 (m, 1H), 2.07-2.00 (m, 1H), 1.87-1.65 (m, 3H).

Intermediate 9: 4-(2-methyl-4-pyridyl)-1H-pyrazolo[3,4-d]pyrimidine

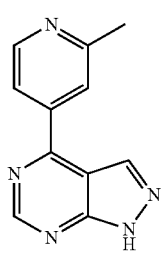 [SMILES: Cc1cc(-c2ncnc3[nH]ncc23)ccn1]

4-(2-methyl-4-pyridyl)-1-tetrahydropyran-2-yl-pyrazolo[3,4-d]pyrimidine (320 mg, 1.08 mmol) was suspended in 4M HCl in 1,4-dioxane solution (10 mL, 40 mmol). The reaction was stirred at room temperature for 16 hours. LCMS showed that the reaction had completed. The reaction was quenched by addition of sat. NaHCO₃ and extracted three times with EtOAc. Combined organic extracts were reduced in vacuo and deposited onto silica. The product was purified on by flash column chromatography (12 g column, 0 to 100% EtOAc in Heptane) to afford 4-(2-methyl-4-pyridyl)-1H-pyrazolo[3,4-d]pyrimidine (55 mg, 0.26 mmol, 24% yield) as a yellow solid.

MS Method 2: RT 0.74 min, ES⁺ m/z 210 [M+H]⁺

¹H NMR (400 MHz, d⁶-DMSO) δ/ppm: 14.35 (bs, 1H), 9.13 (s, 1H), 8.84 (s, 1H), 8.72 (d, 1H, J=5.3 Hz), 8.10 (bs, 1H), 8.04 (d, 1H, J=5.3), 2.66 (s, 3H).

Example 7: 2-[4-(2-methyl-4-pyridyl)pyrazolo[3,4-d]pyrimidin-1-yl]-N-(5-pyrazin-2-yl-2-pyridyl)acetamide

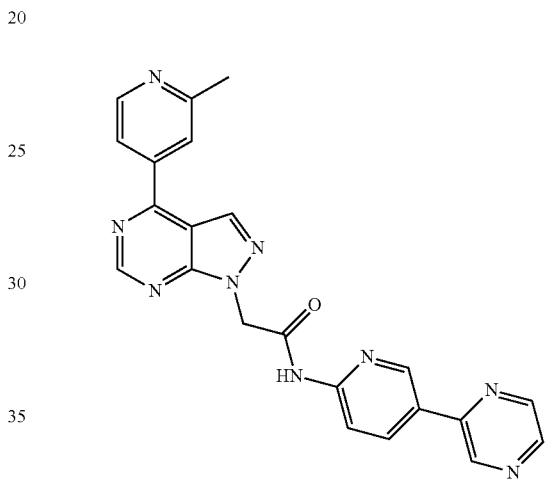

4-(2-methyl-4-pyridyl)-1H-pyrazolo[3,4-d]pyrimidine (122 mg, 0.58 mmol) was dissolved in DMF (5 mL) and cooled to 0° C. NaH (60% dispersed in mineral oil) (28 mg, 0.69 mmol) was added and the reaction was stirred at 0° C. for 45 mins. The reaction was warmed to room temperature and left to stir for 15 mins. The reaction was cooled to 0° C. and 2-chloro-N-(5-pyrazin-2-yl-2-pyridyl)acetamide (186 mg, 0.75 mmol) was added. The reaction was warmed to room temperature and stirred for 3 days. LCMS showed the reaction had completed. The reaction was quenched by the addition of water and extracted three times with EtOAc. Combined organic extracts were reduced in vacuo and deposited onto silica. The product was purified by flash column chromatography (25 g column, 0 to 100% EtOAc in Heptane then 0 to 10% MeOH in EtOAc) to furnish 2-[4-(2-methyl-4-pyridyl)pyrazolo[3,4-d]pyrimidin-1-yl]-N-(5-pyrazin-2-yl-2-pyridyl)acetamide (15 mg, 0.04 mmol, 6% yield) as a white solid.

MS Method 2: RT 1.08 min, ES⁺ m/z 424 [M+H]⁺

¹H NMR (400 MHz, d⁶-DMSO) δ/ppm: 11.4 (s, 1H), 9.32 (d, 1H, J=1.5 Hz), 9.18 (s, 1H), 9.15 (d, 1H, J=2.6 Hz), 8.94 (s, 1H), 8.75-8.72 (m, 2H), 8.64 (d, 1H, J=2.5 Hz), 8.53 (dd, 1H, J=8.8, 2.5 Hz), 8.12 (s, 1H), 8.11 (d, 1H, J=5.8 Hz), 8.08 (d, 1H, J=5.2 Hz), 5.58 (s, 2H), 2.67 (s, 3H).

Example 8

The following compounds were prepared by analogy with General Scheme 4 using the appropriate 5,6-fused chloro heteroaryl and heteroaryl boronic acid.

| Structure | STRUCTURE NAME | LCMS RT (min) | m/z MIM |
|---|---|---|---|
| 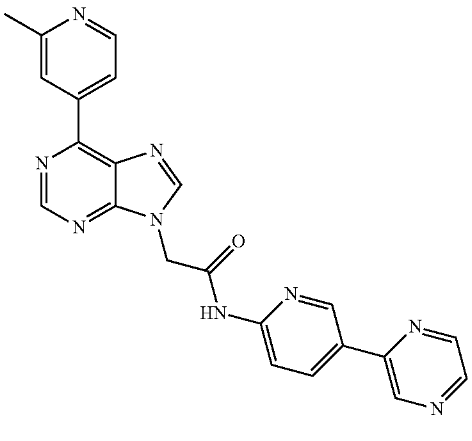 [SMILES: Cc1cc(-c2ncnc3c2ncn3CC(=O)Nc2ccc(-c3cnccn3)cn2)ccn1] | 2-[6-(2-methyl-4-pyridyl)purin-9-yl]-N-(5-pyrazin-2-yl-2-pyridyl-acetamide | 2.27 (Method 1) | 423.43 |
| 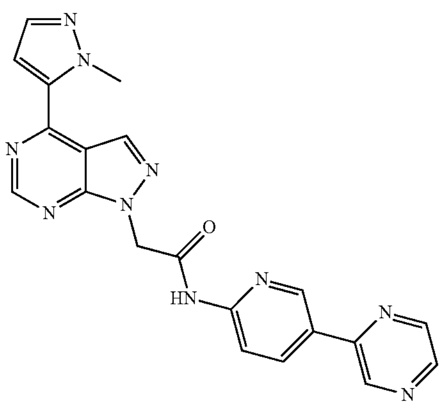 [SMILES: Cn1nccc1-c1ncnc2c1cnn2CC(=O)Nc1ccc(-c2cnccn2)cn1] | 2-[4-(2-methylpyrazol-3-yl)pyrazolo[3,4-d]pyrimidin-1-yl]-N-(5-pyrazin-2-yl-2-pyridyl)acetamide | 2.90 (Method 1) | 412.41 |
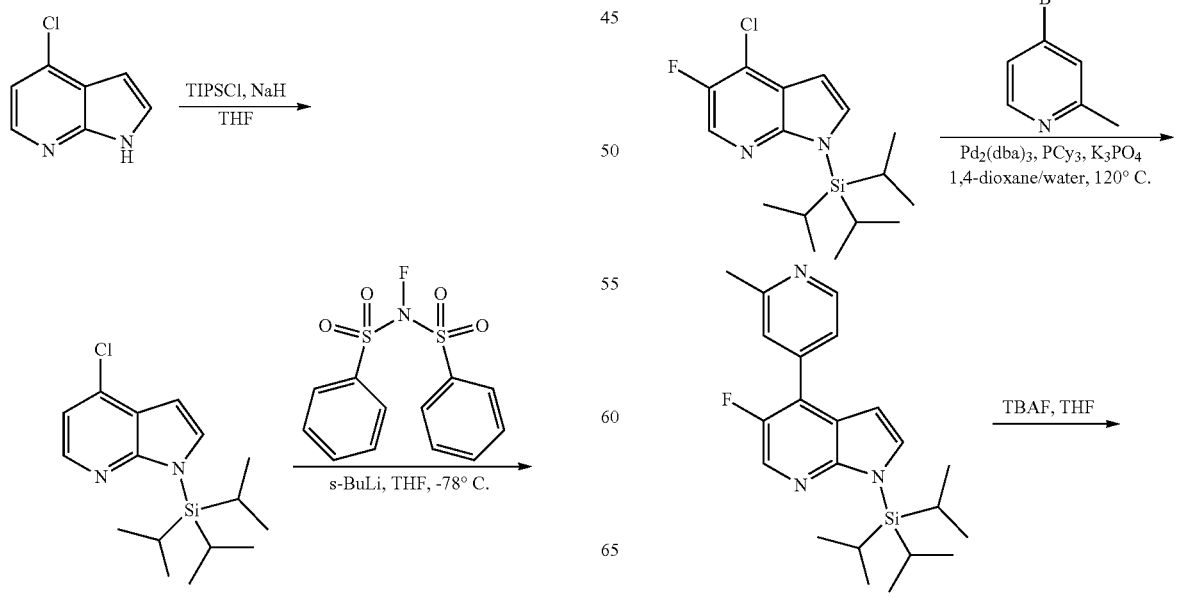
General Scheme 5

-continued

Further compounds of the invention could be prepared by analogy with the following route Intermediate 9: 4-chloropyrrolo[2,3-b]pyridine-1-yl)-triisopropylsilane 4-Chloro-1H-pyrrolo[2,3-b]pyridine (1.05 g, 6.88 mmol) was dissolved in THF (50 mL) and cooled to 0° C. NaH (60% dispersed in mineral oil) (1.5 g, 10.3 mmol) was added and the reaction was stirred at 0° C. for 1 hour. Triisopropylsilyl chloride (2.38 g, 12.4 mmol) was added and the reaction was heated under reflux overnight. TLC (8:2 Heptane/EtOAc) showed consumption of SM (Rf 0.4) and formation of new product spot (0.9). The reaction was quenched with water and extracted three times with EtOAc. Combined organic extracts were reduced in vacuo and deposited onto silica. The product was purified by flash column chromatography (40 g column, 0 to 20% EtOAc in Heptane) to give (4-chloropyrrolo[2,3-b]pyridine-1-yl)-triisopropylsilane (2.1 g, 6.88 mmol, 100% yield).

$^1$H NMR (400 MHz, CDCl$_3$) δ/ppm: 8.21 (d, 1H, J=5.4 Hz, 7.39 (d, 1H, J=3.5 Hz), 7.12 (d, 1H, J=5.4 Hz), 6.74 (dd, 1H, J=3.5 Hz), 1.93 (hept, 3H, J=7.2 Hz), 1.19 (d, 18H, J=7.2 Hz).

Intermediate 10: (4-chloro-5-fluoro-pyrrolo[2,3-b]pyridine-1-yl)-triisopropylsilane 4-chloropyrrolo[2,3-b]pyridine-1-yl)-triisopropylsilane (290 mg, 0.94 mmol) was dissolved in THF (8 mL) and cooled to −78° C. A solution of s-BuLi was added dropwise and the reaction was stirred at −78° C. for 30 mins. A solution of N-fluorobenzenesulfonimide (830 mg, 2.63 mmol) in THF (3 mL) was added and the reaction was stirred at −78° C. for 1 hour. LCMS was inconclusive as neither starting material nor product can be observed. The reaction was quenched at −78° C. by addition of sat. NH$_4$Cl solution and then slowly warmed to room temperature. The reaction mixture was extracted three times with EtOAc and the combined organic extracts were dried over Na$_2$SO$_4$ and reduced in vacuo. The crude product was deposited onto silica and the product purified by flash column chromatography (12 g column, 0 to 20% EtOAc in Heptane) to give (4-chloro-5-fluoro-pyrrolo[2,3-b]pyridine-1-yl)-triisopropylsilane (180 mg, 0.55 mmol, 59% yield) as a white solid.

$^1$H NMR (400 MHz, CDCl$_3$) δ/ppm: 8.18 (d, 1H, J=2.0 Hz), 7.41 (d, 1H, J=3.5 Hz), 6.68 (d, 1H, J=3.5 Hz), 1.86 (hept, 3H, J=7.6 Hz), 1.14 (d, 18H, J=7.6 Hz).

Intermediate 11: [5-fluoro-4-(2-methyl-4-pyridyl)pyrrolo[2,3-b]pyridine-1-yl-triisopropylsilane In a 2.0-5.0 mL microwave vial (4-chloro-5-fluoro-pyrrolo[2,3-b]pyridine-1-yl)-triisopropylsilane (180 mg, 0.55 mmol) and potassium phosphate tribasic (233 mg, 1.10 mmol) were suspended in 1,4-dioxane (4 mL) and water (1 mL). Nitrogen was bubbled through the solution for 10 mins, after which 2-methylpyridine-4-boronic acid (180 mg, 1.31 mmol), tricyclohexylphosphine (15 mg, 0.06 mmol) and tris(dibenzylideneacetone)dipalladium (0) (34 mg, 0.04 mmol) were added. The vial was capped and reaction was heated by microwave irradiation at 120° C. for 1 hour. LCMS indicated completion of reaction. The reaction was diluted with sat. NaHCO$_3$ and extracted three times with EtOAc. Combined organic extracts were reduced in vacuo and deposited onto silica. The crude product was purified by flash column chromatography (12 g, 0 to 50% EtOAc in Heptane) to furnish [5-fluoro-4-(2-methyl-4-pyridyl)pyrrolo[2,3-b]pyridine-1-yl-triisopropylsilane (136 mg, 0.35 mmol, 64% yield) as a colourless oil.

MS Method 2: RT 2.48 min, ES$^+$ m/z 384 [M+H]$^+$ $^1$H NMR (400 MHz, CDCl$_3$) δ/ppm: 8.66 (d, 1H, J=5.2 Hz), 8.24 (d, 1H, J=2.9 Hz), 7.50 (bs, 1H), 7.44-7.41 (m, 2H), 6.59 (d, 1H, J=3.6 Hz), 2.68 (s, 3H), 1.87 (hept, 3H, J=7.7 Hz), 1.16 (d, 18H, J 15=7.7 Hz).

Intermediate 12: 5-fluoro-4-(2-methyl-4-pyridyl)-1H-pyrrolo[2,3-b]pyridine

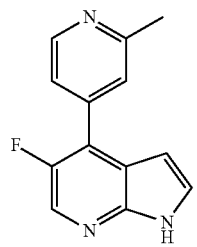

[5-fluoro-4-(2-methyl-4-pyridyl)pyrrolo[2,3-b]pyridine-1-yl-triisopropylsilane (136 mg, 0.35 mmol) was dissolved in THF (3.5 mL) and a 1M solution of tetrabutylammonium fluoride in THF (0.43 mL, 0.43 mmol) was added. The reaction was stirred at room temperature for 2 hours, after which the reaction was observed to be complete by LCMS. The reaction was diluted with water and extracted three times with EtOAc. Combined organic extracts were dried over Na$_2$SO$_4$ and reduced in vacuo to yield 5-fluoro-4-(2-methyl-4-pyridyl)-1H-pyrrolo[2,3-b]pyridine (80 mg, 0.35 mmol, 80% yield) as a yellow solid.

MS Method 2: RT 0.90 min, ES$^+$ m/z 228 [M+H]$^+$ $^1$H NMR (400 MHz, CDCl$_3$) δ/ppm: 9.41 (bs, 1H), 8.69 (d, 1H, J=5.2 Hz), 8.32 (d, 1H, J=3.1 Hz), 7.50 (bs, 1H), 7.47 (dd, 1H, J=3.5, 2.5 Hz), 7.44 (d, 1H, J=3.1 Hz), 6.56 (dd, 1H, J=3.5, 2.0 Hz), 2.69 (s, 3H).

Example 9: 2-[5-fluoro-4-(2-methyl-4-pyridyl)pyrrolo[2,3-b]pyridin-1-yl]-N-(5-pyrazin-2-yl-2-pyridyl)acetamide

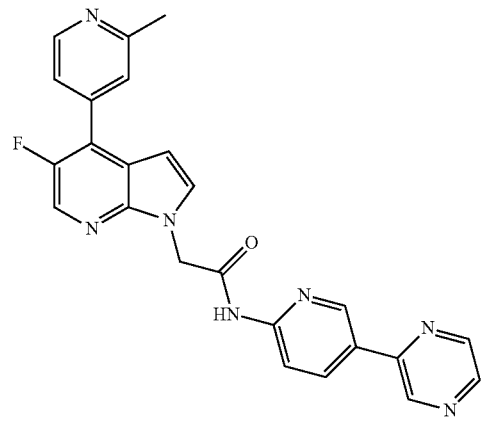 [SMILES: Cc1cc(-c2c(F)cnc3c2ccn3CC(=O)Nc2ccc(-c3cnccn3)cn2)ccn1]

5-fluoro-4-(2-methyl-4-pyridyl)-1H-pyrrolo[2,3-b]pyridine (80 mg, 0.35 mmol) was dissolved in DMF (4 mL) and cooled to 0° C. NaH (60% dispersed in mineral oil) (17 mg, 0.42 mmol) was added and the reaction was stirred at 0° C. for 45 mins, after which the reaction was warmed to room temperature and stirred for 15 mins. The reaction was cooled to 0° C. and 2-chloro-N-(5-pyrazin-2-yl-2-pyridyl)acetamide (114 mg, 0.46 mmol) was added. The reaction was warmed to room temperature and left to stir for 16 hours. LCMS showed a small amount of starting material remaining and also formation of desired product. The reaction was quenched by the addition of water and extracted three times with EtOAc. Combined organic extracts were reduced in vacuo and deposited onto silica. The product was purified by flash column chromatography (12 g column, 0 to 100% EtOAc in Heptane then 0-10% MeOH in EtOAc). The purified product was then purified by prep HPLC to give the purified product 2-[5-fluoro-4-(2-methyl-4-pyridyl)pyrrolo[2,3-b]pyridin-1-yl]-N-(5-pyrazin-2-yl-2-pyridyl)acetamide (10 mg, 0.03 mmol, 6% yield).

MS Method 1: RT 2.58 min, ES$^+$ m/z 440 [M+H]$^+$ $^1$H NMR (400 MHz, d$^6$-DMSO) δ/ppm: 11.28 (s, 1H), 9.32 (d, 1H, J=1.5 Hz), 9.15 (dd, 1H, J=2.5, 0.7 Hz), 8.73 (dd, 1H, J=2.5, 1.5 Hz), 8.66 (d, 1H, J=5.2 Hz), 8.64 (d, 1H, J=2.5 Hz), 8.53 (dd, 1H, J=8.8, 2.5 Hz), 8.38 (d, 1H, J=2.9 Hz), 8.14 (d, 1H, J=8.8 Hz), 7.79 (d, 1H, J=3.5 Hz), 7.56 (s, 1H), 7.49 (d, 1H, J=5.2 Hz), 6.56 (d, 1H, J=3.5 Hz), 5.34 (s, 2H), 2.60 (s, 3H).

Example 10

The following compound was prepared by analogy with General Scheme 5 using the appropriate 5,6-fused chloro heteroaryl.

| Structure | STRUCTURE NAME | LCMS RT (min) | m/z MIM |
|---|---|---|---|
| 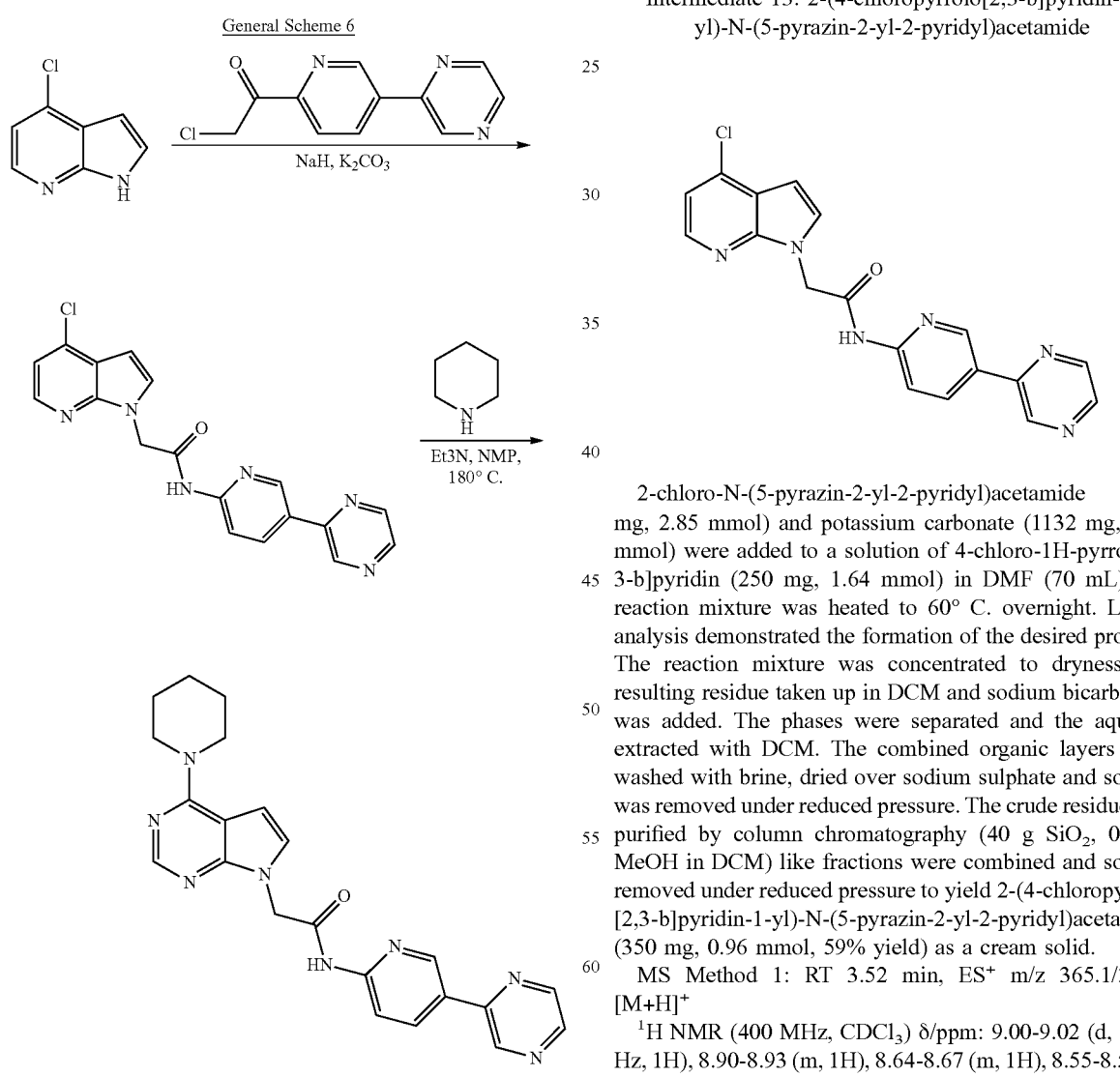 | 2-[5-methyl-4-(2-methyl-4-pyridyl)pyrrolo[2,3-b]pyridin-1-yl]-N-(5-pyrazin-2-yl-2-pyridyl)acetamide | 2.50 (Method 1) | 435.45 |

Further compounds of the invention could be prepared by analogy with the following route Intermediate 13: 2-(4-chloropyrrolo[2,3-b]pyridin-1-yl)-N-(5-pyrazin-2-yl-2-pyridyl)acetamide 2-chloro-N-(5-pyrazin-2-yl-2-pyridyl)acetamide (708 mg, 2.85 mmol) and potassium carbonate (1132 mg, 8.19 mmol) were added to a solution of 4-chloro-1H-pyrrolo[2,3-b]pyridin (250 mg, 1.64 mmol) in DMF (70 mL), the reaction mixture was heated to 60° C. overnight. LCMS analysis demonstrated the formation of the desired product. The reaction mixture was concentrated to dryness, the resulting residue taken up in DCM and sodium bicarbonate was added. The phases were separated and the aqueous extracted with DCM. The combined organic layers were washed with brine, dried over sodium sulphate and solvent was removed under reduced pressure. The crude residue was purified by column chromatography (40 g SiO$_2$, 0-10% MeOH in DCM) like fractions were combined and solvent removed under reduced pressure to yield 2-(4-chloropyrrolo[2,3-b]pyridin-1-yl)-N-(5-pyrazin-2-yl-2-pyridyl)acetamide (350 mg, 0.96 mmol, 59% yield) as a cream solid.

MS Method 1: RT 3.52 min, ES$^+$ m/z 365.1/367.0 [M+H]$^+$ $^1$H NMR (400 MHz, CDCl$_3$) δ/ppm: 9.00-9.02 (d, J=1.5 Hz, 1H), 8.90-8.93 (m, 1H), 8.64-8.67 (m, 1H), 8.55-8.57 (d, J=2.4 Hz, 1H), 8.30-8.39 (m, 3H), 7.40-7.43 (d, J=3.6 Hz, 1H), 7.23-7.25 (d, J=5.3 Hz, 1H), 6.74-6.76 (d, J=3.6 Hz, 1H), 5.23 (s, 2H).

Example 11: 2-[4-(1-piperidyl)pyrrolo[2,3-b]pyridin-1-yl]-N-(5-pyrazin-2-yl-2-pyridyl)acetamide

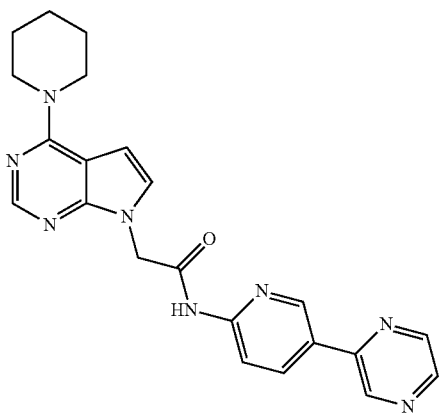 [SMILES: O=C(Cn1ccc2c(N3CCCCC3)ncnc21)Nc1ccc(-c2cnccn2)cn1]

Triethylamine (0.19 mL, 1.37 mmol) and piperidine (0.14 mL, 1.37 mmol) were added to a solution of 2-(4-chloropyrrolo[2,3-b]pyridin-1-yl)-N-(5-pyrazin-2-yl-2-pyridyl)acetamide (100 mg, 0.27 mmol) in NMP (2 mL). The reaction was subjected to microwave radiation at 180° C. for 4 hrs. LCMS analysis demonstrated the reaction had formed the desired product ion. Brine and DCM were added to the reaction mixture, and the layers separated. The aqueous was extracted with DCM (×3), the combined organic layers were dried over sodium sulphate and solvent removed under reduced pressure. The crude residue was purified by column chromatography (0-10% MeOH in DCM) like fractions were combined and solvent removed under reduced pressure. The crude residue was taken up in DMSO:MeCN:H2O (8:1:1) and purified by reverse phase preparative HPLC (eluting with $H_2O$ and MeCN plus 0.1% formic acid). Like fraction were combined and passed through an SCX cartridge, the cartridge was eluted with MeOH and then $NH_3$/MeOH. The $NH_3$/MeOH fractions were combined and solvent removed under reduced pressure to yield 2-[4-(1-piperidyl)pyrrolo[2,3-b]pyridin-1-yl]-N-(5-pyrazin-2-yl-2-pyridyl)acetamide (3 mg, 0.0073 mmol, 2.6% yield) as a colourless solid.

MS Method 1: RT 2.81 min, $ES^+$ m/z 414.1$[M+H]^+$ $^1$H NMR (400 MHz, D6-DMSO) δ/ppm: 11.13 (bs, 1H), 9.30-9.32 (d, J=1.5 Hz, 1H), 9.12-9.14 (m, 1H), 8.71-8.74 (m, 1H), 8.63-8.64 (d, J=2.6 Hz, 1H), 8.50-8.54 (dd, J=2.6, 8.9 Hz, 1H), 8.11-8.16 (d, J=8.7 Hz, 1H), 7.91-7.94 (d, J=5.5 Hz, 1H), 7.33-7.35 (d, J=3.5 Hz, 1H), 6.48-6.50 (d, J=3.7 Hz, 1H), 6.44-6.47 (d, J=5.5 Hz, 1H), 5.19 (s, 2H), 3.40-3.46 (m, 4H), 1.62-1.71 (m, 6H).

Example 12

The following compounds were prepared using the method described in general scheme 6, replacing piperidine with the appropriate saturated amine.

| Structure | STRUCTURE NAME | LCMS RT (min) | m/z MIM |
|---|---|---|---|
| 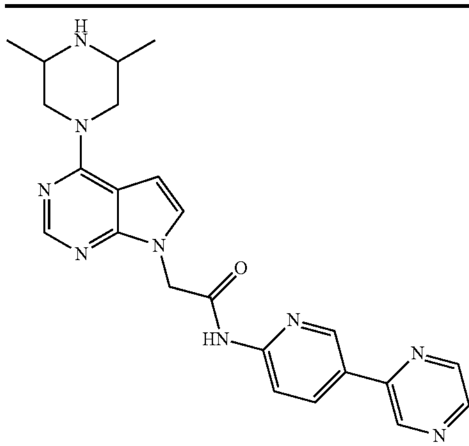 | 2-[4-(3,5-dimethylpiperazin-1-yl)pyrrolo[2,3-b]pyridin-1-yl]-N-(5-pyrazin-2-yl-2-pyridyl)acetamide | 1.83 (Method 1) | 443.1 |
| 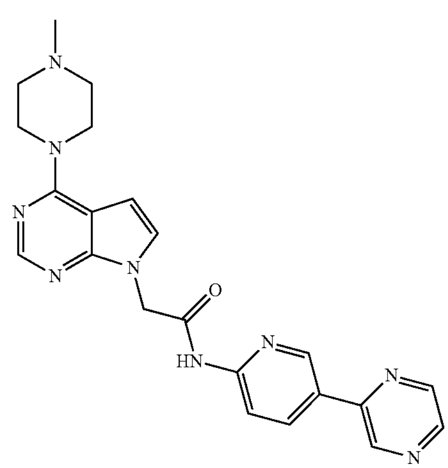 [SMILES: CN1CCN(c2ncnc3c2ccn3CC(=O)Nc2ccc(-c3cnccn3)cn2)CC1] | 2-[4-(4-methylpiperazin-1-yl)pyrrolo[2,3-b]pyridin-1-yl]-N-(5-pyrazin-2-yl-2-pyridyl)acetamide | 1.64 (Method 1) | 429.1 |

Dual-Cell β-Catenin Reporter Assay

Mouse L cells transfected to constitutively produce biologically active murine Wnt-3a, referred to as L-Wnt cells, were purchased from the American Type Culture Collection, ATCC, Manassas, Va. (ATCC). These cells were cultured in DMEM supplemented with 10% FCS (Gibco/Invitrogen, Carlsbad, Calif.), 1% geneticin and 1% sodium pyruvate (Sigma) at 37° C. with 5% $CO_2$. The cells were seeded into 96 well plates and treated with serial dilutions of compound diluted to 0.1% DMSO concentration. After 24 hours, cell supernatants were transferred to a 96 well plate previously seeded with Leading Light® Wnt Reporter Cells, stably transfected with a luciferase gene under control of Wnt pathway response elements. After a further 24 hours, cells are treated with One-glo luciferase assay system (Promega, Madison, Wis.) and the luminescent signal read by envision. The $IC_{50}$ of the compound is determined as the concentration that reduces the induced luciferase signal to 50% of the DMSO control.

The results of the in vitro biological data for certain compounds of the invention are given in the table below. The table shows a group for each compound based on the IC50 value of each compound as "+", "++" and "+++". The category "+" refers to compounds with an IC50 of >5 nM. The category "++" refers to compounds with an IC50 of 1 nM to 5 nM. The category "+++" refers to compounds with an IC50 of <1 nM.

| ID No. | Compound Name | IC50 (nM) |
|---|---|---|
| 1 | 2-[5-methyl-4-(2-methyl-4-pyridyl)pyrrolo[2,3-b]pyridin-1-yl]-N-(5-pyrazin-2-yl-2-pyridyl)acetamide | *** |
| 2 | 2-[5-fluoro-4-(2-methyl-4-pyridyl)pyrrolo[2,3-b]pyridin-1-yl]-N-(5-pyrazin-2-yl-2-pyridyl)acetamide | *** |
| 3 | 2-[5-(2-methyl-4-pyridyl)pyrazolo[3,4-b]pyridin-1-yl]-N-(5-pyrazin-2-yl-2-pyridyl)acetamide | *** |
| 4 | 2-[4-(2-methylpyrazol-3-yl)pyrrolo[3,2-c]pyridin-1-yl]-N-(5-pyrazin-2-yl-2-pyridyl)acetamide | ** |
| 5 | 2-[5-(2-methyl-4-pyridyl)pyrrolo[2,3-b]pyridin-1-yl]-N-(5-pyrazin-2-yl-2-pyridyl)acetamide | *** |
| 6 | 2-[4-(2-methylpyrazol-3-yl)pyrazolo[3,4-b]pyridin-1-yl]-N-(5-pyrazin-2-yl-2-pyridyl)acetamide | * |
| 7 | 2-[4-(2-methylpyrazol-3-yl)pyrrolo[2,3-c]pyridin-1-yl]-N-(5-pyrazin-2-yl-2-pyridyl)acetamide | ** |
| 8 | 2-[2-amino-4-(2-methyl-4-pyridyl)pyrrolo[2,3-d]pyrimidin-7-yl]-N-(5-pyrazin-2-yl-2-pyridyl)acetamide | *** |
| 9 | 2-[5-cyano-4-(2-methyl-4-pyridyl)pyrrolo[2,3-b]pyridin-1-yl]-N-(5-pyrazin-2-yl-2-pyridyl)acetamide | *** |
| 10 | 2-[2-methyl-4-(2-methyl-4-pyridyl)pyrrolo[2,3-d]pyrimidin-7-yl]-N-(5-pyrazin-2-yl-2-pyridyl)acetamide | *** |
| 11 | 2-[4-(2-methylpyrazol-3-yl)pyrazolo[3,4-d]pyrimidin-1-yl]-N-(5-pyrazin-2-yl-2-pyridyl)acetamide | *** |
| 12 | 2-[2-chloro-4-(2-methyl-4-pyridyl)pyrrolo[2,3-d]pyrimidin-7-yl]-N-(5-pyrazin-2-yl-2-pyridyl)acetamide | *** |
| 13 | 2-[6-methyl-4-(2-methyl-4-pyridyl)pyrrolo[2,3-d]pyrimidin-7-yl]-N-(5-pyrazin-2-yl-2-pyridyl)acetamide | * |
| 14 | 2-[4-(2-methyl-4-pyridyl)pyrazolo[3,4-d]pyrimidin-1-yl]-N-(6-pyrazin-2-yl-3-pyridyl)acetamide | ** |
| 15 | 2-[4-(2-methyl-4-pyridyl)pyrazolo[3,4-b]pyridin-1-yl]-N-(6-pyrazin-2-yl-3-pyridyl)acetamide | ** |
| 16 | 2-[4-(2-methyl-4-pyridyl)pyrrolo[2,3-d]pyrimidin-7-yl]-N-(6-pyrazin-2-yl-3-pyridyl)acetamide | * |
| 17 | 2-[4-(2-methyl-4-pyridyl)pyrrolo[2,3-b]pyridin-1-yl]-N-(6-pyrazin-2-yl-3-pyridyl)acetamide | ** |
| 18 | 2-[4-(2-methylpyrazol-3-yl)pyrrolo[2,3-d]pyrimidin-7-yl]-N-(5-pyrazin-2-yl-2-pyridyl)acetamide | ** |
| 19 | 2-[6-(2-methyl-4-pyridyl)purin-9-yl]-N-(5-pyrazin-2-yl-2-pyridyl)acetamide | * |
| 20 | 2-[4-(2-methyl-4-pyridyl)imidazo[4,5-c]pyridin-1-yl]-N-(5-pyrazin-2-yl-2-pyridyl)acetamide | ** |
| 21 | N-(5-pyrazin-2-yl-2-pyridyl)-2-[4-[2-(trifluoromethyl)-4-pyridyl]pyrrolo[2,3-d]pyrimidin-7-yl]acetamide | *** |
| 22 | 2-[4-(2-methyl-4-pyridyl)pyrazolo[3,4-d]pyrimidin-1-yl]-N-(5-pyrazin-2-yl-2-pyridyl)acetamide | *** |
| 23 | 2-[4-(2-methyl-4-pyridyl)pyrrolo[3,2-c]pyridin-1-yl]-N-(5-pyrazin-2-yl-2-pyridyl)acetamide | *** |
| 24 | 2-[4-(2-methyl-4-pyridyl)pyrrolo[2,3-c]pyridin-1-yl]-N-(5-pyrazin-2-yl-2-pyridyl)acetamide | *** |
| 25 | 2-[4-(2-methyl-4-pyridyl)pyrazolo[3,4-b]pyridin-1-yl]-N-(5-pyrazin-2-yl-2-pyridyl)acetamide | *** |
| 26 | 2-[4-(2-methyl-4-pyridyl)pyrrolo[2,3-d]pyrimidin-7-yl]-N-(5-pyrazin-2-yl-2-pyridyl)acetamide | *** |
| 27 | 2-[4-(2-methyl-4-pyridyl)pyrrolo[2,3-b]pyridin-1-yl]-N-(5-pyrazin-2-yl-2-pyridyl)acetamide | *** |
| 28 | 2-[4-(4-methylpiperazin-1-yl)pyrrolo[2,3-b]pyridin-1-yl]-N-(5-pyrazin-2-yl-2-pyridyl)acetamide | * |
| 29 | 2-[4-(3,5-dimethylpiperazin-1-yl)pyrrolo[2,3-b]pyridin-1-yl]-N-(5-pyrazin-2-yl-2-pyridyl)acetamide | * |
| 30 | 2-[4-(1-piperidyl)pyrrolo[2,3-b]pyridin-1-yl]-N-(5-pyrazin-2-yl-2-pyridyl)acetamide | nv |

-continued

| ID No. | Compound Name | IC50 (nM) |
|---|---|---|
| 31 | 2-[4-(2-methylpyrazol-3-yl)pyrrolo[2,3-b]pyridin-1-yl]-N-(5-pyrazin-2-yl-2-pyridyl)acetamide | *** |

Specific $IC_{50}$ values for a selection of compounds of the invention are given below.

| ID no. | Compound | IC50 (nM) |
|---|---|---|
| 27 | 2-[4-(2-methyl-4-pyridyl)pyrrolo[2,3-b]pyridin-1-yl]-N-(5-pyrazin-2-yl-2-pyridyl)acetamide | 0.67 |
| 3 | 2-[5-(2-methyl-4-pyridyl)pyrazolo[3,4-b]pyridin-1-yl]-N-(5-pyrazin-2-yl-2-pyridyl)acetamide | 0.36 |
| 10 | 2-[2-methyl-4-(2-methyl-4-pyridyl)pyrrolo[2,3-d]pyrimidin-7-yl]-N-(5-pyrazin-2-yl-2-pyridyl)acetamide | 0.32 |
| 23 | 2-[4-(2-methyl-4-pyridyl)pyrrolo[3,2-c]pyridin-1-yl]-N-(5-pyrazin-2-yl-2-pyridyl)acetamide | 0.43 |
| 31 | 2-[4-(2-methylpyrazol-3-yl)pyrrolo[2,3-b]pyridin-1-yl]-N-(5-pyrazin-2-yl-2-pyridyl)acetamide | 0.89 |

Specificity Immunoprecipitation

L-Wnt cells can be assessed by treatment with alkanyl-palmitate and several concentrations of compound. After 24 hours cell lysates could be washed in PBS (SOURCE) and collected in ice cold lysis buffer (LYSIS BUFFER). Dynabeads (SOURCE) can be incubated with anti-wnt-3a antibody (Abcam) for 20 minutes and incubated with lysates for an hour. Beads can be isolated by magnet and the unbound faction retained. Click chemistry can be performed on samples using Click-iT® protein buffer kit (Life technologies), following the protocol provided, to conjugate biotin to alkanyl palmitate. Elutes can be separated from the samples by magnet and the resulting samples boiled for 20 minutes to dissociate the conjugates. Beads can be removed and the elutes and unbound fraction can be run by polyacrylamide gel electrophoresis, transferred to a membrane and stained for biotin using streptavidin-horseradish peroxidase and for total Wnt by specific antibody.

Cell Death Assay

Cells in growth media (DMEM, 10% FCS) can be treated with a serial dilution of compound diluted to 0.1% DMSO for 72 hours. Viable cell number was measured by the ability to reduce resazurin to resorufin which was detected by fluorescence emission at 590 nm.

Foci Formation Assay

Capan-2 cells can be seeded onto 6 well plates in standard growth media and treated with serial dilutions of compound. Cell media was changed every four days with fresh compound added. After ten days' growth, cells can be fixed on methanol and treated with crystal violet to visualize. Area covered by cell colonies was detected by Operetta and analysed using Columbus software.

The invention claimed is:

1. A compound of formula (VIa):

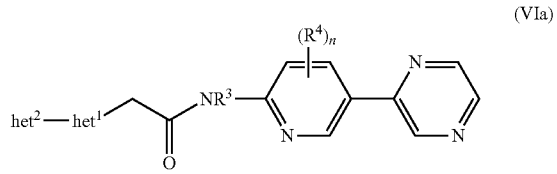

(VIa)

wherein
  $het^1$ represents a substituted or unsubstituted 9 membered bicyclic heteroaryl group comprising a 5 membered ring, wherein the 5 membered ring comprises 1 or 2 nitrogen atoms, and a 6 membered ring, wherein the 6 membered ring comprises 1 or 2 nitrogen atoms, and when substituted the ring system is substituted with 1, 2, or 3 groups independently selected at each occurrence from the group consisting of halo, $C_{1-4}$ alkyl, $C_{1-4}$ haloalkyl, $-OR^{A2}$, $-NR^{A2}R^{B2}$, $-CN$, $-SO_2R^{A2}$, and $C_{3-6}$ cycloalkyl;
  $het^2$ is a 5 or 6 membered heterocyclic ring which may be unsubstituted or substituted, and when substituted the ring is substituted with 1, 2 or 3 groups independently selected at each occurrence from the group consisting of halo, $C_{1-4}$ alkyl, $C_{1-4}$ haloalkyl, $-OR^{A1}$, $-NR^{A1}R^{B1}$, $-CN$, $-NO_2$, $-NR^{A1}C(O)R^{B1}$, $-C(O)NR^{A1}R^{B1}$, $-NR^{A1}SO_2R^{B1}$, $-SO_2NR^{A1}R^{B1}$, $-SO_2R^{A1}$, $-C(O)R^{A1}$, $-C(O)OR^{A1}$ and $C_{3-6}$ cycloalkyl;
  $R^3$ is selected from the group consisting of H, $C_{1-4}$ alkyl, $C_{1-4}$ haloalkyl, and $C_{3-6}$ cycloalkyl;
  $R^4$ is independently selected at each occurrence from the group consisting of halo, $C_{1-4}$ alkyl, $C_{1-4}$ haloalkyl, $-CN$, $-OR^{A4}$, $-NR^{A4}R^{B4}$, $-SO_2R^{A4}$, $C_{3-6}$ cycloalkyl and $C_{3-6}$ halocycloalkyl;
  n is 0, 1 or 2; and
  $R^{A1}$, $R^{B1}$, $R^{A2}$, $R^{B2}$, $R^{A4}$ and $R^{B4}$ are at each occurrence independently selected from the group consisting of H, $C_{1-4}$ alkyl, and $C_{1-4}$ haloalkyl.

2. The compound of claim 1, wherein $het^2$ represents a ring selected from the group consisting of unsubstituted or substituted: pyrazole, imidazole, pyridine, pyrazine, pyrimidine, pyridazine, pyran, tetrahydropyran, dihydropyran, piperidine, piperazine, morpholine, thiomorpholine, oxazine, dioxine, dioxane, thiazine, oxathiane and dithiane.

3. The compound of claim 1, wherein $het^1$ represents a group selected from the group consisting of unsubstituted or substituted: indolizine, purine, pyrrolopyrimidine, pyrazolopyrimidine, azaindole, and azaisoindole.

4. The compound of claim 1, wherein $R^3$ is H or methyl.

5. The compound of claim 1, wherein $R^4$ is independently selected at each occurrence from the group consisting of H, chloro, fluoro, methyl, ethyl, trifluoromethyl, trifluoroethyl, $-OCF_3$, $-OH$, $-OMe$, $-OEt$, $-NH_2$, $-NHMe$, and $-NMe_2$.

6. The compound of claim 1, wherein n is 0.

7. The compound of claim 1, wherein the compound is selected from the group consisting of:

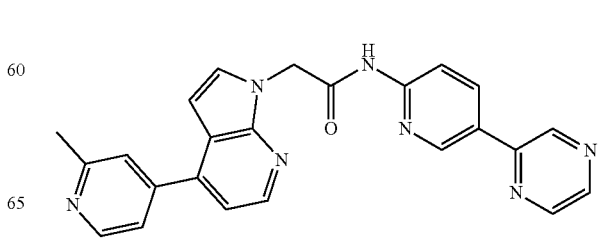

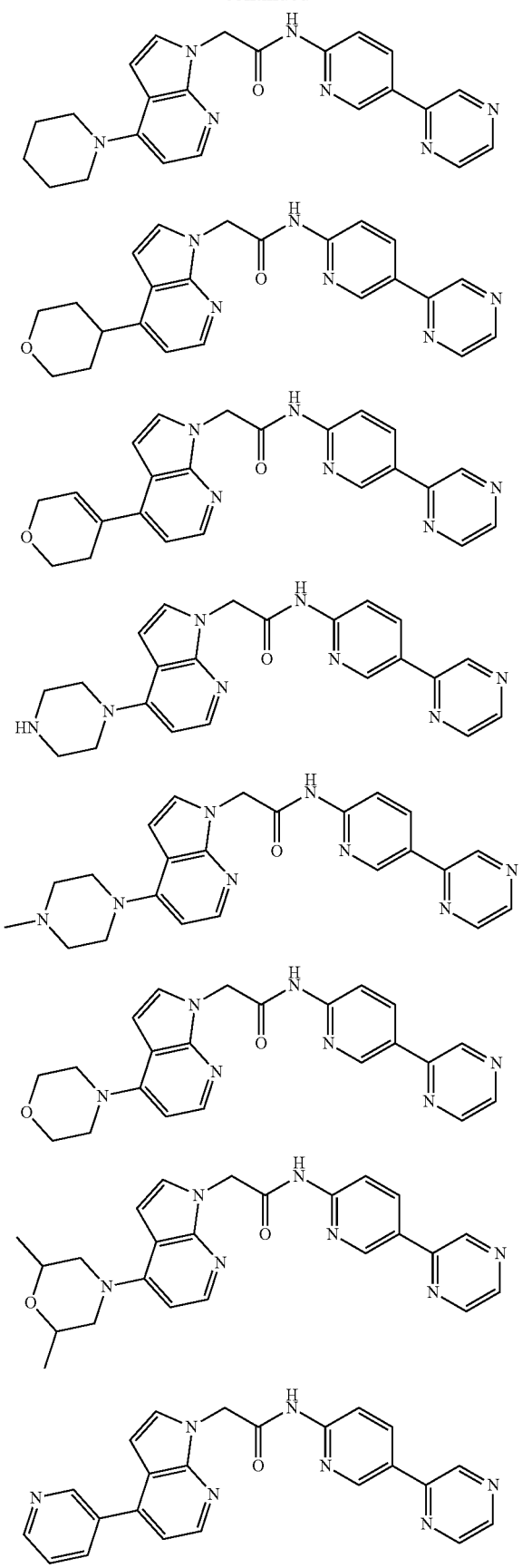
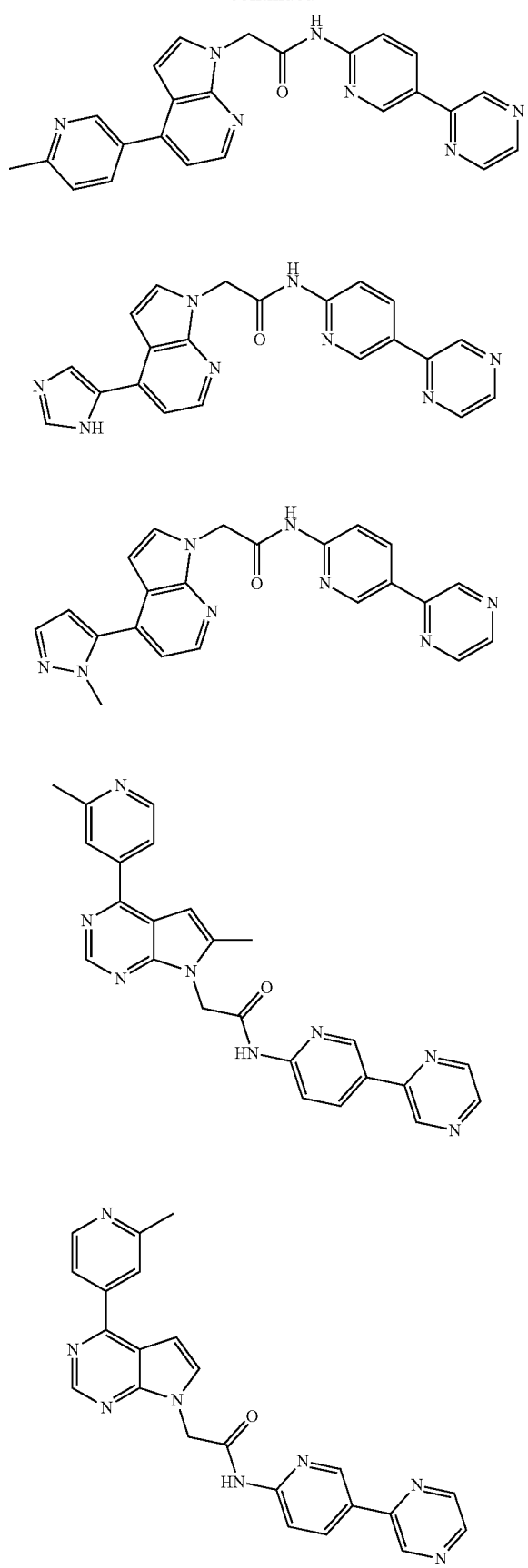

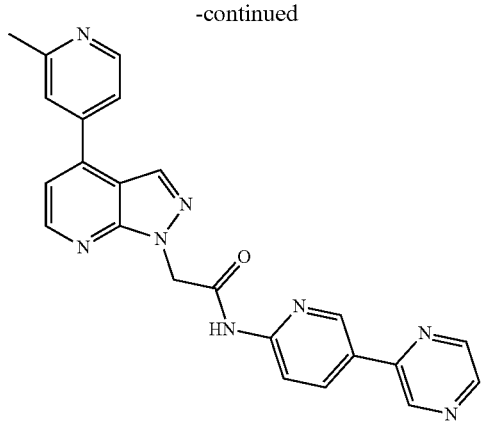
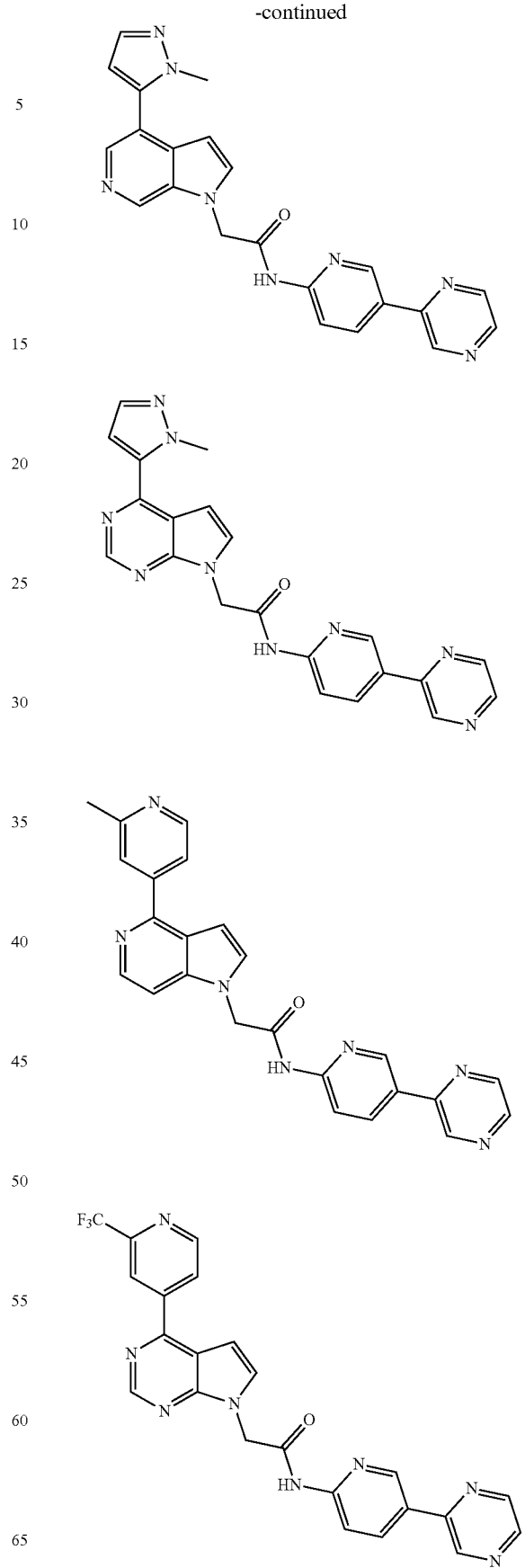

-continued
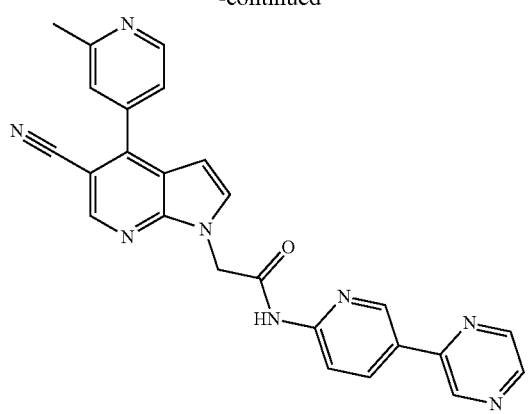
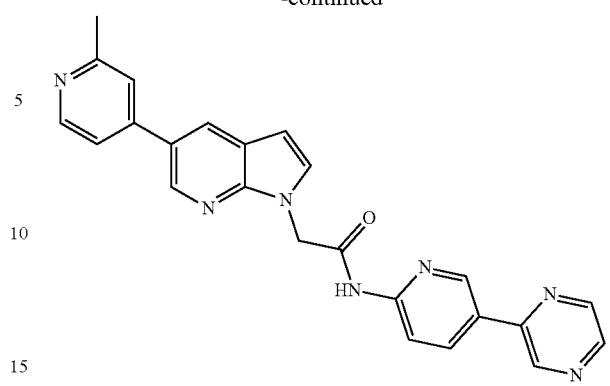
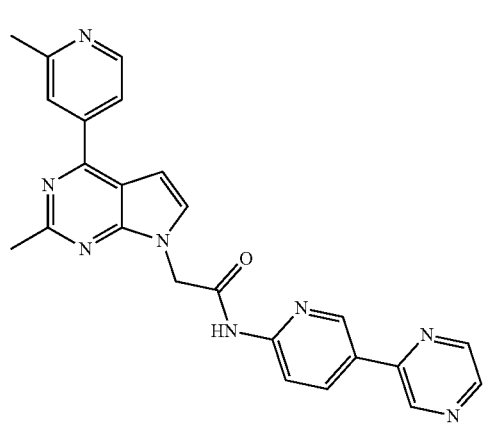
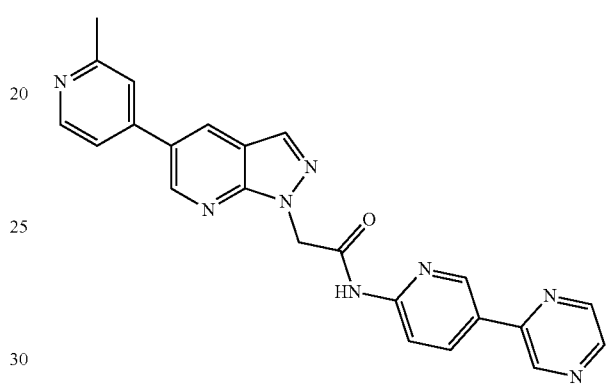
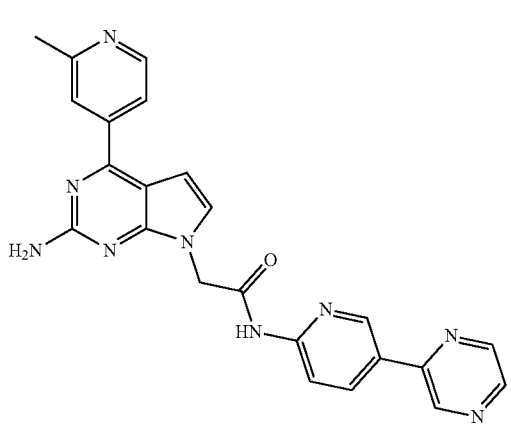
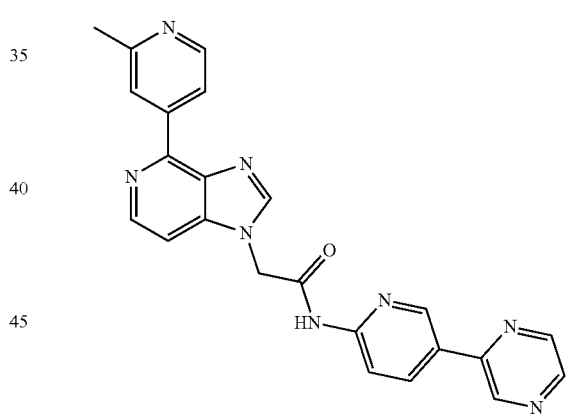
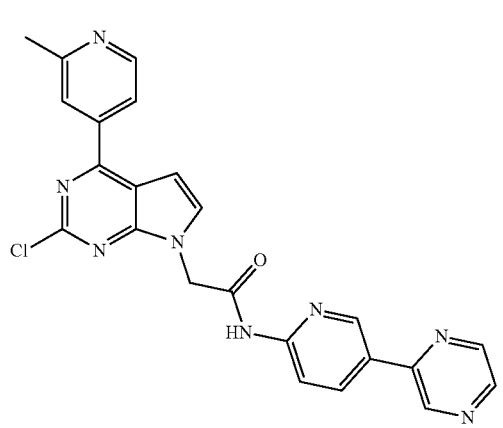
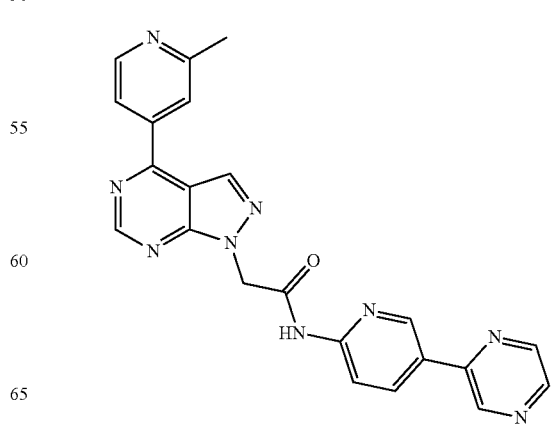

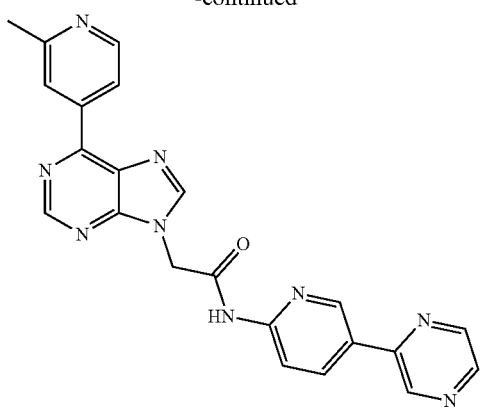

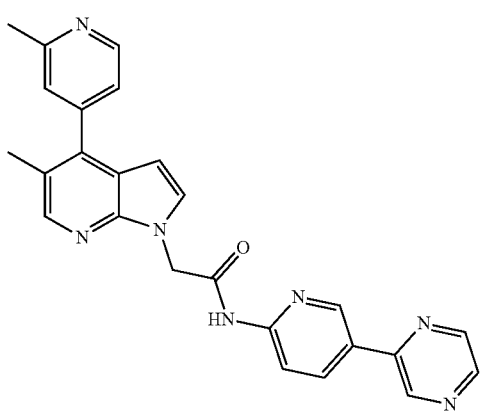

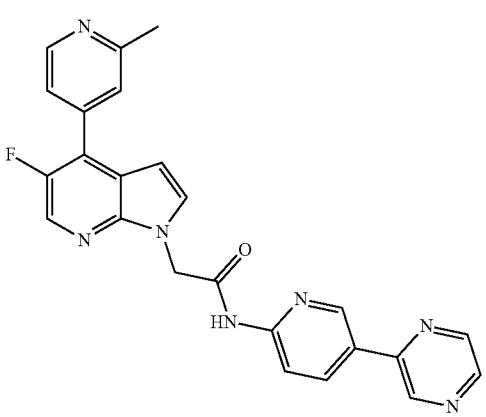

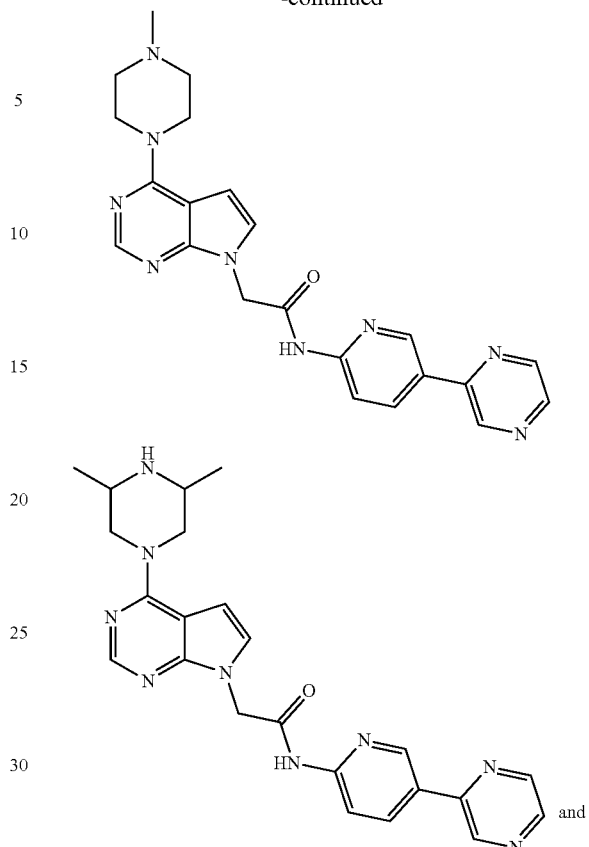

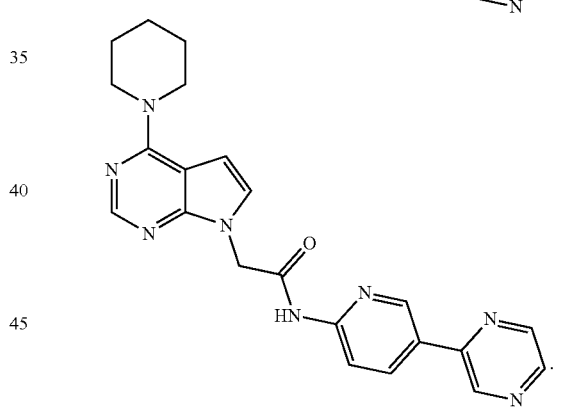

and

8. A method of treatment of a condition modulated by Wnt signalling or the inhibition of porcupine (Porcn), which is selected from the group consisting of sarcoma, melanoma, skin cancer, haematological tumors, lymphoma, carcinoma, and leukemia, wherein the method comprises administering to a patient in need thereof a therapeutic amount of a compound of claim 1.

9. A method of treatment of a condition modulated by Wnt signalling or the inhibition of Porcn, which is selected from the group consisting of esophageal squamous cell carcinoma, gastric cancer, glioblastomas, astrocytomas, retinoblastoma, osteosarcoma, chondosarcoma, Ewing's sarcoma, rabdomysarcoma, Wilm's tumor, basal cell carcinoma, non-small cell lung cancer, brain tumour, prostate cancer, breast cancer, pancreatic cancer, colorectal cancer, cervical cancer, and cancer of the head and neck, wherein the method comprises administering to a patient in need thereof a therapeutic amount of a compound of claim 1.

10. A method of treatment of a condition modulated by Wnt signalling or the inhibition of Porcn, which is selected from the group consisting of skin fibrosis, idiopathic pulmonary fibrosis, renal interstitial fibrosis, liver fibrosis, proteinuria, kidney graft rejection, osteoarthritis, Parkinson's disease, cystoid macular edema, uveitis associated cystoid macular edema, and retinopathy, wherein the method comprises administering to a patient in need thereof a therapeutic amount of a compound of claim 1.

11. A pharmaceutical formulation comprising a compound of claim 1; and a pharmaceutically acceptable excipient.

12. The pharmaceutical composition of claim 11, further comprising an additional pharmaceutically active agent.

13. A compound of formula (VIb):

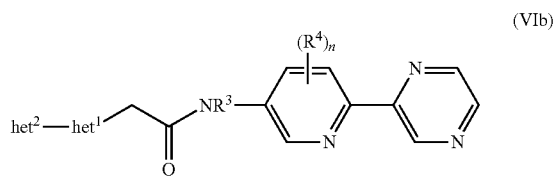

(VIb)

wherein
$het^1$ represents a substituted or unsubstituted 9 membered bicyclic heteroaryl group comprising a 5 membered ring, wherein the 5 membered ring comprises 1 or 2 nitrogen atoms, and a 6 membered ring, wherein the 6 membered ring comprises 1 or 2 nitrogen atoms, and when substituted the ring system is substituted with 1, 2, or 3 groups independently selected at each occurrence from the group consisting of halo, $C_{1-4}$ alkyl, $C_{1-4}$ haloalkyl, —$OR^{A2}$, —$NR^{A2}R^{B2}$, —CN, —$SO_2R^{A2}$, and $C_{3-6}$ cycloalkyl;
$het^2$ is a 5 or 6 membered heterocyclic ring which may be unsubstituted or substituted, and when substituted the ring is substituted with 1, 2 or 3 groups independently selected at each occurrence from the group consisting of halo, $C_{1-4}$ alkyl, $C_{1-4}$ haloalkyl, —$OR^{A1}$, —$NR^{A1}R^{B1}$, —CN, —$NO_2$, —$NR^{A1}C(O)R^{B1}$, —$C(O)NR^{A1}R^{B1}$, —$NR^{A1}SO_2R^{B1}$, —$SO_2NR^{A1}R^{B1}$, —$SO_2R^{A1}$, —$C(O)R^{A1}$, —$C(O)OR^{A1}$ and $C_{3-6}$ cycloalkyl;
$R^3$ is selected from the group consisting of H, $C_{1-4}$ alkyl, $C_{1-4}$ haloalkyl, and $C_{3-6}$ cycloalkyl;
$R^4$ is independently selected at each occurrence from the group consisting of halo, $C_{1-4}$ alkyl, $C_{1-4}$ haloalkyl, —CN, —$OR^{A4}$, —$NR^{A4}R^{B4}$, —$SO_2R^{A4}$, $C_{3-6}$ cycloalkyl and $C_{3-6}$ halocycloalkyl;
n is 0, 1 or 2; and
$R^{A1}$, $R^{B1}$, $R^{A2}$, $R^{B2}$, $R^{A4}$ and $R^{B4}$ are at each occurrence independently selected from the group consisting of H, $C_{1-4}$ alkyl, and $C_{1-4}$ haloalkyl.

14. The compound of claim 13, wherein $het^2$ represents a ring selected from the group consisting of unsubstituted or substituted: pyrazole, imidazole, pyridine, pyrazine, pyrimidine, pyridazine, pyran, tetrahydropyran, dihydropyran, piperidine, piperazine, morpholine, thiomorpholine, oxazine, dioxine, dioxane, thiazine, oxathiane and dithiane.

15. The compound of claim 13, wherein $het^1$ represents a group selected from the group consisting of unsubstituted or substituted: indolizine, purine, pyrrolopyrimidine, pyrazolopyrimidine, azaindole, and azaisoindole.

16. The compound of claim 13, wherein $R^3$ is H or methyl.

17. The compound of claim 13, wherein $R^4$ is independently selected at each occurrence from the group consisting of H, chloro, fluoro, methyl, ethyl, trifluoromethyl, trifluoroethyl, —$OCF_3$, —OH, —OMe, —OEt, —$NH_2$, —NHMe, and —$NMe_2$.

18. The compound of claim 13, wherein n is 0.

19. The compound of claim 13, wherein the compound is selected from the group consisting of:

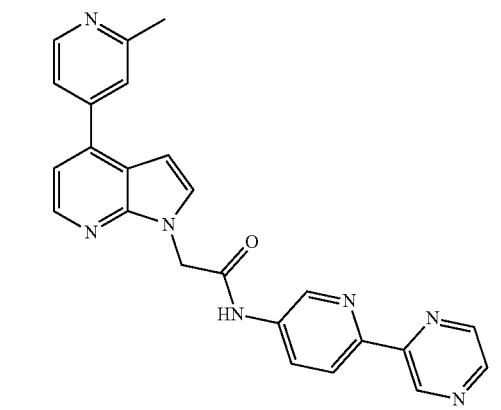

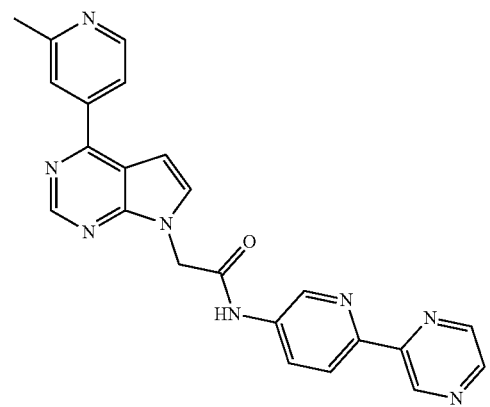

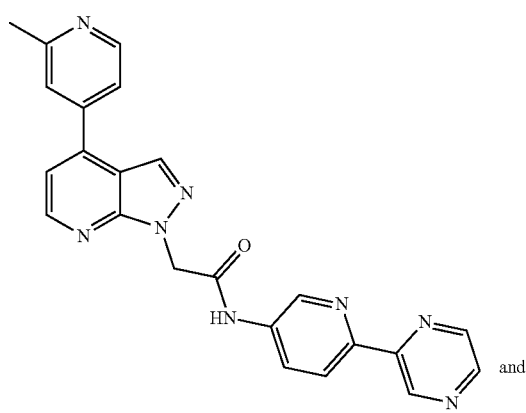

and

-continued

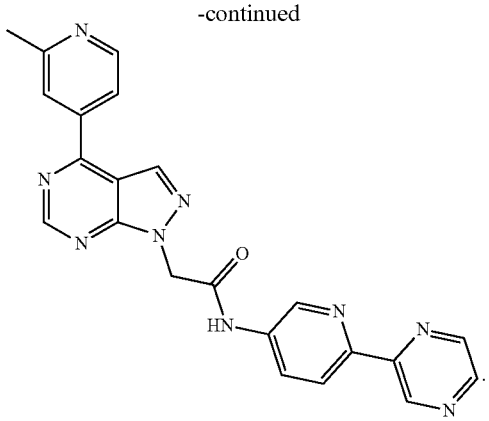

20. A method of treatment of a condition modulated by Wnt signalling or the inhibition of Porcn, which is selected from the group consisting of sarcoma, melanoma, skin cancer, haematological tumors, lymphoma, carcinoma, and leukemia, wherein the method comprises administering to a patient in need thereof a therapeutic amount of a compound of claim 13.

21. A method of treatment of a condition modulated by Wnt signalling or the inhibition of porcupine (Porcn), which is cancer, wherein the method comprises administering to a patient in need thereof a therapeutic amount of a compound of claim 1.

22. A method of treatment of a condition modulated by Wnt signalling or the inhibition of porcupine (Porcn), which is cancer, wherein the method comprises administering to a patient in need thereof a therapeutic amount of a compound of claim 13.

23. A method of treatment of a condition modulated by Wnt signalling or the inhibition of Porcn, which is selected from the group consisting of hormone refractory prostate cancer, metastatic breast cancer, metastatic pancreatic cancer, and head and neck squamous cell carcinoma wherein the method comprises administering to a patient in need thereof a therapeutic amount of a compound of claim 1.

24. A method of treatment of a condition modulated by Wnt signalling or the inhibition of Porcn, which is selected from diabetic retinopathy and retinopathy of prematurity wherein the method comprises administering to a patient in need thereof a therapeutic amount of a compound of claim 1.

* * * * *